(12) United States Patent
Baarman et al.

(10) Patent No.: US 12,274,802 B2
(45) Date of Patent: Apr. 15, 2025

(54) UV DISINFECTION PLATFORM

(71) Applicant: UV Partners, Inc., Grand Haven, MI (US)

(72) Inventors: David W Baarman, Fennville, MI (US); Paul Byrne, Washington, DC (US); Luke Platz, Austin, TX (US); Ryan D. Schamper, Grand Haven, MI (US); Colin J. Moore, Grand Rapids, MI (US)

(73) Assignee: UV Partners, Inc., Grand Haven, MI (US)

( * ) Notice: Subject to any disclaimer, the term of this patent is extended or adjusted under 35 U.S.C. 154(b) by 0 days.

(21) Appl. No.: 17/952,948

(22) Filed: Sep. 26, 2022

(65) Prior Publication Data

US 2023/0014466 A1    Jan. 19, 2023

Related U.S. Application Data

(63) Continuation of application No. 17/751,973, filed on May 24, 2022, now Pat. No. 11,918,698, which is a
(Continued)

(51) Int. Cl.
*A61L 2/10* (2006.01)
(52) U.S. Cl.
CPC ............. *A61L 2/10* (2013.01); *A61L 2202/11* (2013.01); *A61L 2202/14* (2013.01)
(58) Field of Classification Search
None
See application file for complete search history.

(56) References Cited

U.S. PATENT DOCUMENTS

D133,214 S    7/1942    Ohm
D148,191 S    12/1947   Schuler
(Continued)

FOREIGN PATENT DOCUMENTS

AU    2015266601 A1 *  1/2017    ........... A61L 2/0047
CN    103446604 A      12/2013
(Continued)

OTHER PUBLICATIONS

International Seach Report and the Written Opinion of the International Searching Authority for International Application No. PCT/US2021/021056 mailed Aug. 3, 2021, pp. 1-19.
(Continued)

*Primary Examiner* — Andrew Smyth
(74) *Attorney, Agent, or Firm* — Warner Norcross + Judd LLP

(57) ABSTRACT

A disinfection platform for at least partially disinfecting a proximal surface is provided. A disinfection apparatus includes a housing defining an aperture, a UV light source enclosed in the housing configured to project a UV illumination pattern toward a target disinfection area where the disinfection apparatus is disposed above one end and oriented at a downward angle. The illumination pattern output from the disinfection apparatus at least partially defined by louvers and an occlusion nose with reflective fins positioned at the aperture such that the illumination pattern at the target disinfection surface has improved intensity distribution. Multiple sensors cooperate with a control circuit operating the UV light source to provide intelligent and automated control with pattern detection, event based disinfection, and validation. Dual passive infrared sensors enable improved pattern detection for presence detection, accelerometer improves touch detection, and gyroscope provides attitude installation configuration.

30 Claims, 24 Drawing Sheets

Related U.S. Application Data continuation of application No. PCT/US2021/021056, filed on Mar. 5, 2021.

(60) Provisional application No. 62/985,976, filed on Mar. 6, 2020.

(56) References Cited

U.S. PATENT DOCUMENTS

| | | |
|---|---|---|
| 3,314,746 A | 4/1967 | Millar |
| 3,698,780 A | 10/1972 | Collins et al. |
| 4,710,634 A | 12/1987 | Brookes |
| 4,896,042 A | 1/1990 | Humphreys |
| 4,899,057 A | 2/1990 | Koji |
| 4,907,316 A | 3/1990 | Kurz |
| 4,952,369 A | 8/1990 | Belilos |
| 5,008,933 A | 4/1991 | Kao et al. |
| 5,124,131 A | 6/1992 | Wekhof |
| 5,126,572 A | 6/1992 | Chu |
| 5,379,201 A | 1/1995 | Friedman |
| 5,422,487 A | 6/1995 | Sauska et al. |
| 5,459,944 A | 10/1995 | Tatsutani et al. |
| 5,744,094 A | 4/1998 | Castberg et al. |
| 5,866,076 A | 2/1999 | Fenci et al. |
| 5,894,130 A | 4/1999 | Bach |
| 5,920,075 A | 7/1999 | Whitehead |
| D425,273 S | 5/2000 | Stephens et al. |
| RE36,896 E | 10/2000 | Maarschalkerweerd |
| 6,132,784 A | 10/2000 | Brandt et al. |
| 6,221,314 B1 | 4/2001 | Bigelow |
| 6,239,442 B1 | 5/2001 | Iimura |
| 6,242,753 B1 | 6/2001 | Sakurai |
| 6,258,736 B1 | 7/2001 | Massholder |
| 6,278,122 B1 | 8/2001 | Gagnon |
| 6,301,359 B1 | 10/2001 | Roberts |
| 6,371,424 B1 | 4/2002 | Shaw |
| D457,667 S | 5/2002 | Piepgras et al. |
| 6,403,030 B1 | 6/2002 | Horton, III |
| 6,433,344 B1 | 8/2002 | Salisbury et al. |
| 6,447,720 B1 | 9/2002 | Horton et al. |
| 6,447,721 B1 | 9/2002 | Horton, III et al. |
| 6,458,331 B1 | 10/2002 | Roberts |
| 6,490,351 B1 | 12/2002 | Roberts |
| 6,524,529 B1 | 2/2003 | Horton, III |
| D475,154 S | 5/2003 | Binsukor |
| 6,566,659 B1 | 5/2003 | Clark et al. |
| 6,579,495 B1 | 6/2003 | Maiden |
| 6,592,816 B1 | 7/2003 | Ebel et al. |
| 6,614,039 B2 | 9/2003 | Hollander |
| D483,511 S | 12/2003 | Lay et al. |
| 6,656,424 B1 | 12/2003 | Deal |
| 6,670,626 B2 | 12/2003 | Witham et al. |
| 6,680,844 B2 | 1/2004 | Kim |
| 6,692,694 B1 | 2/2004 | Curry et al. |
| D487,527 S | 3/2004 | Sieczkowski |
| 6,720,950 B2 | 4/2004 | Cheng |
| 6,752,627 B2 | 6/2004 | Lin |
| 6,797,966 B2 | 9/2004 | Summers et al. |
| D500,884 S | 1/2005 | O'Rourke |
| 6,838,057 B2 | 1/2005 | Russell et al. |
| D506,279 S | 6/2005 | Sirichai et al. |
| 6,906,337 B2 | 6/2005 | Wedekamp |
| 6,939,397 B2 | 9/2005 | Nelson et al. |
| 6,953,940 B2 | 10/2005 | Leighley et al. |
| D524,956 S | 7/2006 | Chan |
| 7,077,372 B2 | 7/2006 | Moran |
| 7,175,807 B1 | 2/2007 | Jones |
| 7,202,484 B1 | 4/2007 | Tantillo |
| D544,627 S | 6/2007 | Quintal |
| 7,227,534 B2 | 6/2007 | Lin et al. |
| 7,250,615 B1 | 7/2007 | Soong et al. |
| 7,261,264 B2 | 8/2007 | Moran |
| 7,332,124 B2 | 2/2008 | Trifu et al. |
| 7,372,044 B2 | 5/2008 | Ross |
| 7,407,624 B2 | 8/2008 | Cumberland et al. |
| 7,424,314 B2 | 9/2008 | Park |
| 7,427,763 B2 | 9/2008 | Rudkowski |
| 7,462,849 B2 | 12/2008 | Ferres et al. |
| 7,547,893 B1 | 6/2009 | Tantillo |
| 7,598,501 B2 | 10/2009 | Jones |
| 7,612,492 B2 | 11/2009 | Lestician |
| 7,692,159 B2 | 4/2010 | Lane et al. |
| 7,692,172 B2 | 4/2010 | Leben |
| 7,759,873 B2 | 7/2010 | Mastenbroek et al. |
| 7,801,334 B2 | 9/2010 | Shin et al. |
| 7,834,335 B2 | 11/2010 | Harmon et al. |
| D630,364 S | 1/2011 | Schmitt et al. |
| 7,888,657 B1 | 2/2011 | Zadro |
| 7,960,706 B2 | 6/2011 | Ullman |
| 7,969,505 B2 | 6/2011 | Saito |
| 7,989,779 B1 | 8/2011 | Ray et al. |
| 8,084,752 B2 | 12/2011 | Ranta et al. |
| 8,087,737 B2 | 1/2012 | Shoenfeld |
| 8,105,532 B2 | 1/2012 | Harmon et al. |
| 8,110,819 B2 | 2/2012 | Boyarsky et al. |
| 8,114,346 B2 | 2/2012 | Hyde et al. |
| 8,161,596 B2 | 4/2012 | Cheung et al. |
| 8,168,903 B2 | 5/2012 | Chen |
| 8,168,963 B2 | 5/2012 | Ratcliffe |
| D662,250 S | 6/2012 | Wauters |
| 8,226,255 B2 | 7/2012 | Fan |
| 8,226,887 B2 | 7/2012 | Harmon et al. |
| 8,242,466 B2 | 8/2012 | Uber |
| D669,204 S | 10/2012 | Snell et al. |
| 8,277,724 B2 | 10/2012 | Jung et al. |
| 8,283,639 B2 | 10/2012 | Lane et al. |
| 8,297,435 B2 | 10/2012 | Lathen |
| 8,299,445 B2 | 10/2012 | Yamada et al. |
| D671,254 S | 11/2012 | Miyatake et al. |
| 8,330,121 B2 | 12/2012 | Douglas |
| 8,378,324 B2 | 2/2013 | Gardner, III |
| 8,399,854 B1 | 3/2013 | Crawford |
| 8,431,910 B1 | 4/2013 | Perry |
| 8,458,954 B2 | 6/2013 | Yamada et al. |
| D686,772 S | 7/2013 | Waltz et al. |
| 8,479,900 B2 | 7/2013 | Scicluna |
| 8,481,970 B2 | 7/2013 | Cooper et al. |
| 8,519,361 B2 | 8/2013 | Leben |
| 8,536,541 B2 | 9/2013 | Taylor et al. |
| 8,569,715 B1 | 10/2013 | Tantillo |
| D694,448 S | 11/2013 | Li |
| 8,575,567 B2 | 11/2013 | Lyslo et al. |
| 8,581,522 B2 | 11/2013 | Inskeep |
| 8,597,569 B2 | 12/2013 | Gruen et al. |
| 8,598,539 B2 | 12/2013 | Chuang |
| 8,606,981 B2 | 12/2013 | Engelhardt et al. |
| 8,624,203 B2 | 1/2014 | Tullo et al. |
| 8,680,496 B2 | 3/2014 | Leben |
| 8,696,985 B2 | 4/2014 | Gil et al. |
| 8,758,679 B2 | 6/2014 | Hyde et al. |
| D712,104 S | 8/2014 | Stickney et al. |
| 8,841,634 B2 | 9/2014 | Statham et al. |
| 8,884,258 B1 | 11/2014 | Liao et al. |
| 8,895,939 B2 | 11/2014 | Lyslo et al. |
| D720,876 S | 1/2015 | Haverfield |
| 9,125,957 B2 | 9/2015 | Freue et al. |
| 9,242,018 B2 | 1/2016 | Cole et al. |
| D750,310 S | 2/2016 | Cole et al. |
| 9,901,652 B2 | 2/2018 | Cole et al. |
| 9,974,873 B2 | 5/2018 | Cole |
| 10,413,624 B2 | 9/2019 | Cole et al. |
| 10,835,628 B2 | 11/2020 | Cole |
| 10,918,750 B2 | 2/2021 | Cole et al. |
| 11,097,026 B2 | 8/2021 | Baarman |
| 11,173,222 B2 | 11/2021 | Baarman |
| 11,219,699 B2 | 1/2022 | Cole et al. |
| 2001/0042842 A1 | 11/2001 | Leighley |
| 2002/0005834 A1 | 1/2002 | Oh |
| 2002/0074559 A1 | 6/2002 | Dowling et al. |
| 2002/0085947 A1 | 7/2002 | Deal |
| 2002/0190171 A1 | 12/2002 | Stock |
| 2005/0236013 A1 | 10/2005 | Huston et al. |
| 2006/0097189 A1 | 5/2006 | Lim |
| 2006/0120915 A1 | 6/2006 | Lewandowski |
| 2006/0158353 A1 | 7/2006 | Tseng |

(56) References Cited

U.S. PATENT DOCUMENTS

| | | |
|---|---|---|
| 2006/0188389 A1 | 8/2006 | Levy |
| 2006/0213792 A1 | 9/2006 | Nguyen et al. |
| 2006/0216193 A1 | 9/2006 | Johnson et al. |
| 2007/0023710 A1 | 2/2007 | Tom et al. |
| 2007/0071636 A1 | 3/2007 | Bovino et al. |
| 2007/0195550 A1 | 8/2007 | Tsai |
| 2007/0231192 A1 | 10/2007 | Jung et al. |
| 2007/0231193 A1 | 10/2007 | Jung et al. |
| 2007/0251812 A1 | 11/2007 | Hayman, Jr. |
| 2007/0258852 A1 | 11/2007 | Hootsmans et al. |
| 2008/0002049 A1 | 1/2008 | Saito |
| 2008/0008620 A1 | 1/2008 | Alexiadis |
| 2008/0067418 A1 | 3/2008 | Ross |
| 2008/0187190 A1 | 8/2008 | Shin et al. |
| 2008/0199353 A1 | 8/2008 | Mlodzinski et al. |
| 2008/0199354 A1 | 8/2008 | Gordon |
| 2008/0253941 A1 | 10/2008 | Wichers et al. |
| 2008/0256741 A1 | 10/2008 | Garcia et al. |
| 2008/0267831 A1 | 10/2008 | Lee |
| 2009/0117001 A1 | 5/2009 | Hyde et al. |
| 2009/0123331 A1 | 5/2009 | Ross |
| 2009/0140891 A1 | 6/2009 | Ragusa et al. |
| 2009/0180934 A1 | 7/2009 | Khoshbin |
| 2009/0191100 A1 | 7/2009 | Deal |
| 2009/0212234 A1 | 8/2009 | Vestal |
| 2009/0218512 A1 | 9/2009 | Ranta et al. |
| 2009/0246073 A1 | 10/2009 | Murphy |
| 2009/0252646 A1 | 10/2009 | Holden et al. |
| 2009/0314308 A1 | 12/2009 | Kim et al. |
| 2009/0317436 A1 | 12/2009 | Wilson et al. |
| 2010/0097013 A1 | 4/2010 | Inskeep |
| 2010/0104471 A1 | 4/2010 | Harmon et al. |
| 2010/0111775 A1 | 5/2010 | Hyde |
| 2010/0127189 A1 | 5/2010 | Boyarsky et al. |
| 2010/0127984 A1 | 5/2010 | Chen |
| 2011/0054574 A1 | 3/2011 | Felix |
| 2011/0158862 A1 | 6/2011 | Kim et al. |
| 2011/0174992 A1 | 7/2011 | Sakita |
| 2011/0214686 A1 | 9/2011 | Chavana, Jr. et al. |
| 2011/0215261 A1 | 9/2011 | Lyslo et al. |
| 2011/0256019 A1 | 10/2011 | Gruen |
| 2011/0291995 A1 | 12/2011 | Shr et al. |
| 2012/0112100 A1 | 5/2012 | Lo |
| 2012/0121457 A1 | 5/2012 | Farren |
| 2012/0141322 A1 | 6/2012 | Fogg |
| 2012/0141323 A1 | 6/2012 | Fogg |
| 2012/0176241 A1 | 7/2012 | Pasch et al. |
| 2012/0187313 A1 | 7/2012 | Clark et al. |
| 2012/0227211 A1 | 9/2012 | Hwang et al. |
| 2012/0282135 A1 | 11/2012 | Trapani |
| 2012/0286038 A1 | 11/2012 | Wu |
| 2012/0305787 A1 | 12/2012 | Henson |
| 2012/0305804 A1 | 12/2012 | Goldman |
| 2013/0017122 A1 | 1/2013 | Jung et al. |
| 2013/0045132 A1 | 2/2013 | Tuanov |
| 2013/0062534 A1 | 3/2013 | Cole |
| 2013/0129567 A1 | 5/2013 | Gray |
| 2013/0240756 A1 | 9/2013 | Segal |
| 2013/0270445 A1 | 10/2013 | Gaska et al. |
| 2013/0330235 A1 | 12/2013 | Stibich et al. |
| 2014/0048724 A1 | 2/2014 | Marshall |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0091236 A1 | 4/2014 | Jhawar et al. |
| 2014/0131595 A1 | 5/2014 | Nathan et al. |
| 2014/0140888 A1 | 5/2014 | Neister |
| 2014/0161663 A1 | 6/2014 | Farren et al. |
| 2014/0175280 A1 | 6/2014 | Tantillo |
| 2014/0183377 A1 | 7/2014 | Bettles et al. |
| 2014/0227132 A1 | 8/2014 | Neister |
| 2014/0250778 A1 | 9/2014 | Suntych |
| 2014/0284499 A1 | 9/2014 | Schumacher |
| 2014/0299793 A1 | 10/2014 | Deng |
| 2014/0301893 A1 | 10/2014 | Stroup et al. |
| 2014/0322073 A1 | 10/2014 | Link et al. |
| 2014/0336495 A1 | 11/2014 | Bittner |
| 2015/0028228 A1 | 1/2015 | Almasy et al. |
| 2015/0090903 A1 | 4/2015 | Cole |
| 2015/0090904 A1 | 4/2015 | Cole |
| 2015/0182647 A1 | 7/2015 | Ranta et al. |
| 2016/0210436 A1 | 7/2016 | Ambrose et al. |
| 2016/0375165 A1 | 12/2016 | Cole et al. |
| 2017/0246329 A1 | 8/2017 | Lloyd |
| 2017/0296686 A1* | 10/2017 | Cole ................... A61L 2/26 |
| 2018/0117201 A1 | 5/2018 | Bettles et al. |
| 2018/0296711 A1 | 10/2018 | Brais et al. |
| 2018/0311388 A1 | 11/2018 | Cole et al. |
| 2019/0022260 A1 | 1/2019 | Cole |
| 2019/0030195 A1 | 1/2019 | Hatti et al. |
| 2019/0282718 A1 | 9/2019 | Cole |
| 2019/0388572 A1 | 12/2019 | Cole et al. |
| 2021/0316025 A1 | 10/2021 | Cole |

FOREIGN PATENT DOCUMENTS

| | | |
|---|---|---|
| EP | 2 257 791 | 12/2010 |
| GB | 2 375 504 | 11/2002 |
| GB | 2 421 220 | 3/2008 |
| KR | 2007-0057715 | 6/2007 |
| WO | 92/18170 | 10/1992 |
| WO | 94/13331 | 6/1994 |
| WO | 95/28181 | 10/1995 |
| WO | 97/33631 | 9/1997 |
| WO | 99/19002 | 4/1999 |
| WO | 00/41733 | 7/2000 |
| WO | 00/41734 | 7/2000 |
| WO | 02/43782 | 6/2002 |
| WO | 02/45756 | 6/2002 |
| WO | 02/058744 | 8/2002 |
| WO | 2004/035095 | 4/2004 |
| WO | 2004/080495 | 9/2004 |
| WO | 2005/011755 | 2/2005 |
| WO | 2005/030371 | 4/2005 |
| WO | 2006/060689 | 6/2006 |
| WO | 2006/091364 | 8/2006 |
| WO | 2006/092111 | 9/2006 |
| WO | 2007/008879 | 1/2007 |
| WO | 2007/059609 | 5/2007 |
| WO | 2007/071981 | 6/2007 |
| WO | 2007/090876 | 8/2007 |
| WO | 2007/103704 | 9/2007 |
| WO | 2007/126883 | 11/2007 |
| WO | 2007/127006 | 11/2007 |
| WO | 2007/149585 | 12/2007 |
| WO | 2008/040316 | 4/2008 |
| WO | 2008/096123 | 8/2008 |
| WO | 2009/056765 | 5/2009 |
| WO | 2009/123813 | 10/2009 |
| WO | 2009/147628 | 12/2009 |
| WO | 2010/026416 | 3/2010 |
| WO | 2010/051808 | 5/2010 |
| WO | 2010/060079 | 5/2010 |
| WO | 2010/090601 | 8/2010 |
| WO | 2010/147282 | 12/2010 |
| WO | 2011/033263 | 3/2011 |
| WO | 2011/055140 | 5/2011 |
| WO | 2011/107540 | 9/2011 |
| WO | 2011/143265 | 11/2011 |
| WO | WO-2011143265 A2 * | 11/2011 ............... A61L 2/10 |
| WO | 2012/096896 | 7/2012 |
| WO | 2013/025894 | 2/2013 |
| WO | 2013/074481 | 5/2013 |
| WO | 2013/106076 | 7/2013 |
| WO | 2013/106077 | 7/2013 |
| WO | 2014/013385 | 1/2014 |
| WO | 2014/022717 | 2/2014 |
| WO | 2014/036080 | 3/2014 |
| WO | 2014/036089 | 3/2014 |
| WO | 2014/044008 | 3/2014 |
| WO | 2014/078324 | 5/2014 |
| WO | 2014/101994 | 7/2014 |

(56) References Cited

FOREIGN PATENT DOCUMENTS

| WO | 2014/106196 | | 7/2014 | | |
|---|---|---|---|---|---|
| WO | 2014/169808 | | 10/2014 | | |
| WO | 2015/013312 | | 1/2015 | | |
| WO | 2015/051024 | | 4/2015 | | |
| WO | WO-2015184428 | A1 * | 12/2015 | ........... | A61L 2/0047 |
| WO | 2016/105347 | | 6/2016 | | |
| WO | 2019/241453 | A1 | 12/2019 | | |
| WO | WO-2019241112 | A1 * | 12/2019 | ............... | A61L 2/10 |

OTHER PUBLICATIONS

Coxworth, B., "Germ Genie shown to kill 99 percent of germs on keyboards", New Atlas, Oct. 5, 2010, pp. 1-3.
University of Hertfordshire, "Launch of Germ Genie to kill keyboard germs", Science Daily, Oct. 4, 2010, pp. 1-3.
Hosein, I.K, et al., "In-use evaluation of an automated ultraviolet lamp for bio-decontamination of hospital computer keyboards", North Middlesex University Hospital, Apr. 1, 2012, p. 1.
Renesas, "Introduction to Proximity Sensing", AN1436, Rev 0.00, Mar. 26, 2019, pp. 1-11.

* cited by examiner

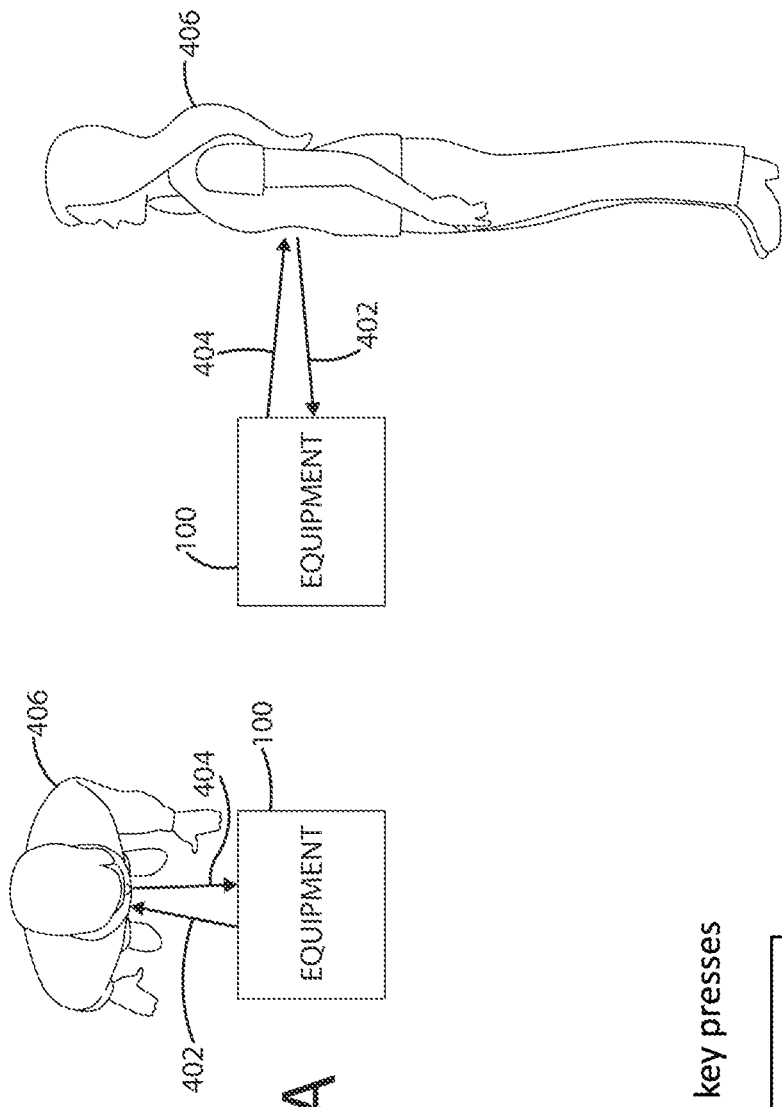
Fig. 18A
Fig. 18B
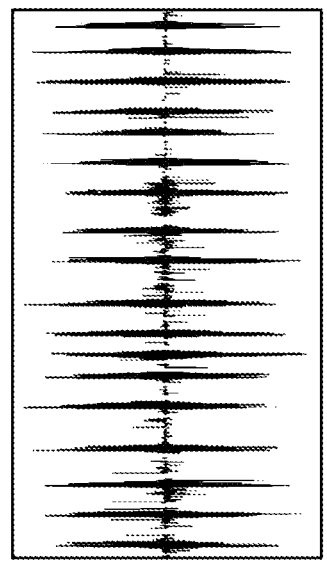
Fig. 19

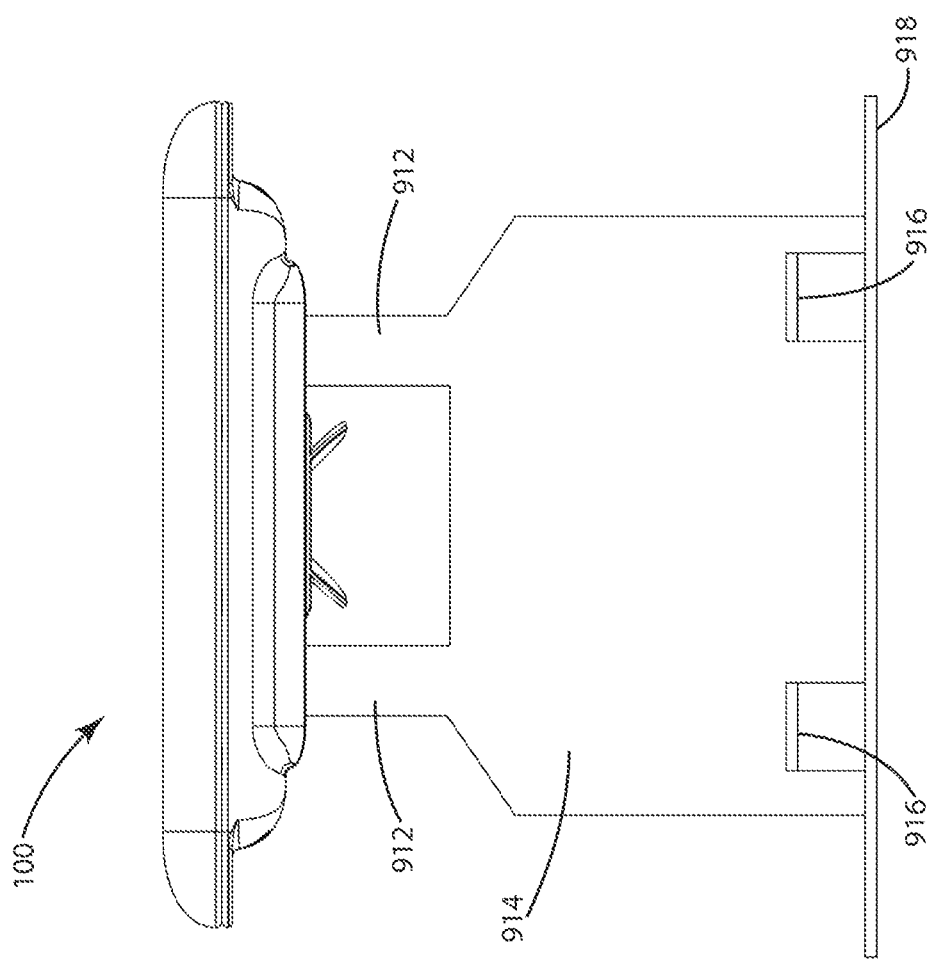
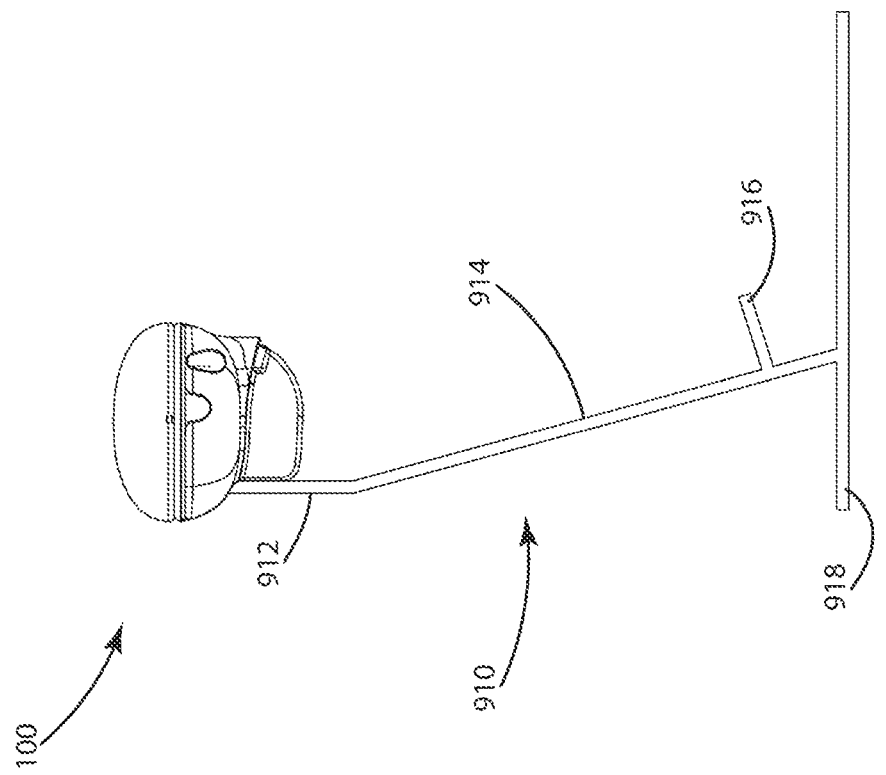
Fig. 27A
Fig. 27B

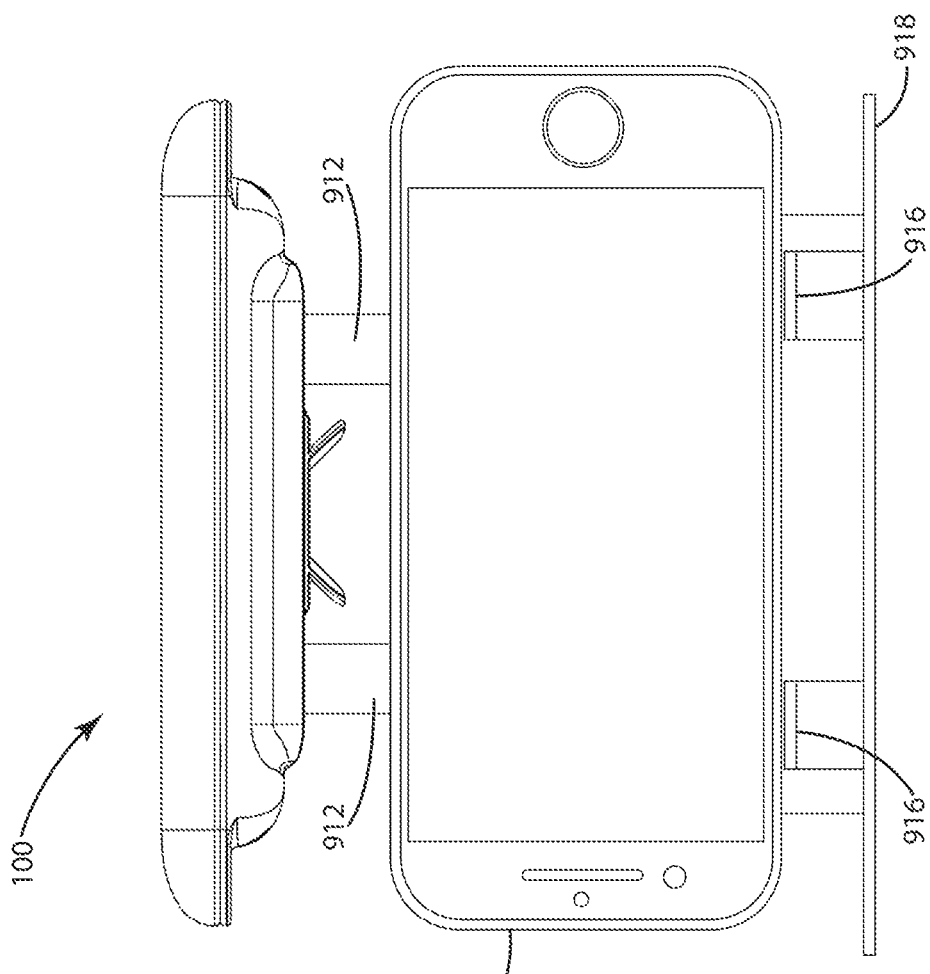
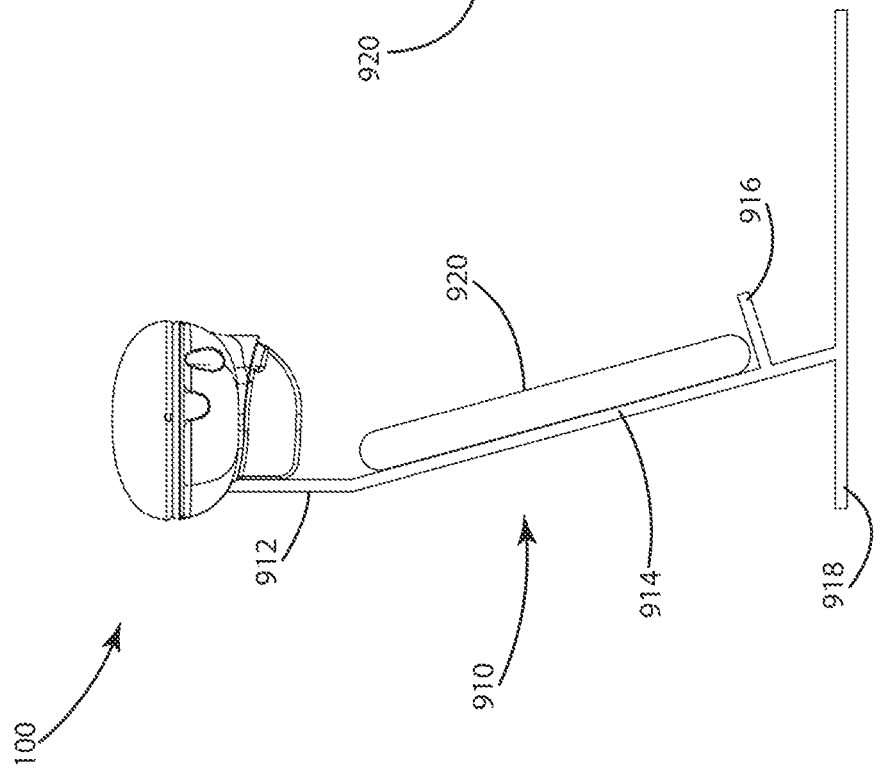
Fig. 28B
Fig. 28A

UV DISINFECTION PLATFORM

FIELD OF THE INVENTION

The present invention relates to disinfection, and more particularly to systems and methods associated with disinfection.

BACKGROUND OF THE INVENTION

A healthcare associated infection or hospital acquired infection ("HAI") is an infection that develops as a result of medical care. HAIs affect millions of people across the world and add billions of dollars to healthcare costs annually. It is well known that HAIs continue to present a significant health risk. A variety of efforts have been made to reduce the risks presented by HAIs. For example, there is increasing interest in performing germicidal activities in a hospital environment. This includes the growing use of UV disinfection systems to perform repeated disinfection of a wide range of objects. There are currently a number of different types of UV disinfection products available on the commercial market. Many conventional UV disinfection products suffer from a variety of shortcomings. For example, UV energy has a tendency to degrade plastics and other materials. As a result, conventional UV disinfection treatment regimens may have the unintended consequence of causing excessive undesirable damage to objects in and around the treatment ranges.

There has been dramatic growth in the use of networks to collect data relating to a range of activities in and around hospitals and other medical environments. Although some of these systems are already gathering data relating to personnel, asset tracking, electronic medical records and patient health, the data is not being leveraged in a cost-efficient, reliable, and effective manner.

Other issues continue to persist with known systems such as lack of coordination from multiple workflows, understanding how to handle high touch areas and their infection impact, and the lack of robust engineered disinfection solutions. Some of these issues are exacerbated by healthcare environmental services cleaning and disinfection practices that are stretched.

Hospital cleaning and environmental sanitation is a core function of every hospital because it is improves patient safety and is a necessary baseline for providing high quality of care. Conventional standard cleaning of an occupied patient room according to proper procedures can take 30 minutes or more, while terminal cleaning can take more than 45 minutes. However, often times there is pressure to complete these tasks in much less time with fewer resources, which can lead to poor outcomes. Furthermore, the amount of time to properly clean various hospital rooms can vary from hospital to hospital depending on a wide range of factors, such as traffic level and training.

Accordingly, existing patient-care, electronic medical records, and device workflow create vectors for nosocomial transmissions. Specific HAI challenges include:
Cross contamination that pits patient care versus HAI transmission;
Specific infections, such as *Clostridium difficile* ("C. Diff"), methicillin-resistant *Staphylococcus aureus* ("MRSA"), vancomycin-resistant *Staphylococcus aureus* ("VRSA"), vancomycin-resistant enterococci ("VRE"), and *Klebsiella pneumoniae* carbapenemase ("KPC");
Bioburden due to lack of device disinfection effectiveness;
Accumulation of pathogens on devices and equipment;
Lack of effective and sufficient hand sanitization in workflow; and
Human error and intervention in workflow.

Many prior art disinfection systems rely on enclosing an area to be disinfected and flooding the enclosed area with high intensity UV light to ensure disinfection. These high intensity solutions require a large amount of human intervention due to the safety issues associated with high intensity UV light. For small scale high intensity solutions a user may be required to open an enclosure, place a device in the enclosure, activate the disinfection system, and then remember to retrieve the device when the disinfection is complete. Even where these disinfection systems are integrated into a storage solution, they still require user intervention to pick and place the device being disinfected, a step that often can be forgotten or ignored. Larger scale high intensity solutions may not require a user to rearrange the devices being disinfected, but may require movement of a mobile UV transmitter into the space to be disinfected that floods the entire room with high intensity UV light. Even where the large scale disinfection system is incorporated into the room permanently, such systems require evacuation and active participation by humans in the safety procedures in order to ensure that no humans are in the vicinity during the disinfection process.

In addition to the inconvenience created by these solutions that require significant human interaction, the high intensity UV light is prone to create UV hot spots that can cause damage to the items being disinfected or the surroundings. Some known issues of prior UV treatment technologies relate to a lack of understanding of the impact of UV energy on the target being disinfected and the UV treatment device itself. Many UV treatment systems prescribe the "more is better" mantra, which has negative ramifications, especially for materials that are not intended for intense UV exposure. Other issues with prior UV disinfection systems relate to safely and consistently automating the disinfection process.

Some attempts have been made to provide engineered disinfection solutions that significantly reduce human interaction in the disinfection process. For example, U.S. Pub. 2015/0297766 to Cole, filed on Oct. 2, 2013, discloses a portable light fastening assembly for use with a human interface of an electronic device, which is hereby incorporated by reference in its entirety. The assembly includes a lamp housing and an ultra-violet ("UV") light source partially enclosed in the housing for automatically disinfecting a touch surface of a human interface device with UV-C light. For example, the assembly can utilize a passive infrared motion sensor to detect human presence to control activation of the UV light source. As another example, the disclosure describes detecting quick movement of the UV light assembly with an accelerometer and shutting off the UV light in response. While this and other UV disinfection systems have advanced the area of engineered disinfection solutions, there are opportunities for further improvement.

SUMMARY OF THE INVENTION

The present disclosure is generally directed to a UV disinfection platform that provides an intelligent, automated UV-C light disinfection system that can perform continuous monitoring to detect when a surface warrants disinfection and automatically disinfect without assistance from a user.

One aspect of the present disclosure is generally directed to a disinfection device and method for UV pattern shaping, intensity limiting, or both. A disinfection device can include an occlusion nose that has a plate and fins to limit intensity of UV light and shape the UV light pattern. A hole can also be included in the plate to ensure sufficient UV light reaches an otherwise completely occluded area. The nose can be replaceable, providing the ability to swap in and out different noses for different situations, such as different orientations/positions and different disinfection environments. The disinfection device can include reflective fins that shape the UV light pattern to reach otherwise unreachable areas. A louver and eyebrow configuration can limit include optics for limiting line of sight and light intensity.

Another aspect of the present disclosure generally relates to disinfection control. The disinfection apparatus and method can include pattern recognition, which allows detection of events based on patterns in sensor output. Specific events can be detected in response to detecting specific combination of sensor output from different sensors. Event or flag based disinfection can be provided that can set "ready to clean" and "dirty" flags based on sensor output patterns and initiate disinfection when both are set. The disinfection control can include detection of specific events based on a specific. A progressive delay mode can automatically increase delay time based on disinfection cycle interruptions. Delay time refers to the time the control system waits before initiating a disinfection cycle after detecting a lack of human presence as part of the disinfection control loop. An overdose prevention mode can automatically lower dosage in response to dosage per time thresholds and other triggers. Detection methodology can be improved with redundant event detection based on different sensor output.

Another aspect of the present disclosure generally relates to specific sensor functionality and control system event detection. Dual passive infrared sensors can detect lateral human movement. Covers can protect the sensors from environmental noise. Combination with other sensors for various event detection. Improved presence detection can be provided with a time of flight sensor or camera, providing redundancy and speed. Touch detection with accelerometer output, such as cleaning, typing, and mouse clicks. Gyroscope can be calibrated at installation and configured to detect a change in attitude past a guard-band and in response deactivate the UV source and flag tampering.

In general, one innovative aspect of the subject matter described in this specification can be embodied in a UV disinfection device. The UV disinfection device includes a housing with a UV-C light source installed within that is configured to emit UV-C light toward an opening in the housing. A lens covers a portion of the opening and is configured to direct UV-C light from the UV-C light source through the opening. A UV-C reflector can be positioned in the housing and configured reflect UV-C light toward the opening of the housing. A UV-C illumination pattern shaping system extends, at least partially, from the opening. The UV-C illumination pattern shaping system receives UV-C light from the opening in a first UV-C illumination pattern and is configured to shape the first UV-C light illumination pattern into a second, different, UV-C illumination pattern.

The foregoing and other embodiments can each optionally include one or more of the following features, alone or in combination. In particular, one embodiment includes all the following features in combination.

In some embodiments, the UV-C illumination pattern shaping system includes a louver frame joined to the housing. Directional louvers extend from the louver frame within the opening such that UV-C light incident with the louvers and louver frame changes from the first UV-C illumination pattern to the second UV-C illumination pattern. The louvers and louver frame are configured to increase uniformity of intensity of a third UV-C illumination pattern cast on a target disinfection surface by the second UV-C illumination pattern relative to a hypothetical fourth UV-C illumination pattern cast on the target disinfection surface by the first UV-C illumination pattern. The UV-C illumination pattern shaping system can include an eyebrow that cooperates with the louvers to increase uniformity of the third UV-C illumination pattern cast on the target disinfection surface. The housing is oriented such that the opening points at a downward angle with respect to the target disinfection surface such that the eyebrow limits line of sight for a user positioned at about eye level with the UV disinfection device.

In some embodiments, the housing is oriented such that the opening points at a downward angle with respect to the target disinfection surface, wherein a dynamic progression of spacing between the plurality of louvers limits direct line of sight to the UV source for a user positioned at about eye level with the UV disinfection device.

In some embodiments, the UV-C illumination pattern shaping system includes an occlusion nose positioned at the opening, wherein a portion of the UV-C light passing through the opening is blocked by the occlusion nose such that the first UV-C illumination pattern is split into two disparate UV-C illumination patterns, one passing through the opening to one side of the occlusion nose and another passing through the opening to another side of the occlusion nose, wherein the occlusion nose increases uniformity of intensity of the third UV-C illumination pattern cast on the target disinfection surface. The occlusion nose can include an aperture, or two apertures one larger than the other, that allows a portion of UV-C light to pass through such that the intensity of the third UV-C illumination pattern cast on the target disinfection surface is above a threshold level across the entire target disinfection surface.

In some embodiments, the UV-C illumination pattern shaping system includes a pair of fins extending outwardly from the occlusion nose positioned at the opening. The inner surface of each fin can be UV reflective and the angle of the fin can be configured to shape the second UV-C illumination pattern such that it reaches the corners of the target disinfection area, such as the corners of a keyboard.

In general, another group of embodiments of a disinfection device can include a housing with an opening, a UV light source, a lens, and an optical an optical occlusion positioned within or proximate the opening. The optical occlusion can be configured to occlude a portion of the UV light through the opening to limit UV light intensity of a uniform UV illumination pattern cast on an expected target disinfection area.

The foregoing and other embodiments can each optionally include one or more of the following features, alone or in combination. In particular, one embodiment includes all the following features in combination.

In some embodiments, the optical occlusion includes louvers extending laterally across the opening that have a dynamic progression of spacing between the louvers to limit UV light intensity of the uniform UV illumination pattern cast on the expected target disinfection area.

In some embodiments, the optical occlusion includes an eyebrow positioned to limit UV light intensity of the uniform UV illumination pattern cast on the expected target disinfection area or line of sight for a user positioned at about eye level with the UV disinfection device.

In some embodiments, the optical occlusion positioned within the opening includes an occlusion nose configured to split an unoccluded portion of the UV light into two UV illumination patterns, one passing through the opening to one side of the occlusion nose and another passing through the opening to another side of the occlusion nose. The two UV illumination patterns contribute to the uniform UV illumination pattern cast on the expected target disinfection area.

In some embodiments, the occlusion nose includes an aperture that allows a portion of the occluded UV light to instead pass through the occlusion nose and contribute to the uniform UV illumination pattern cast on the expected target disinfection area.

In some embodiments, the occlusion nose includes an occlusion plate having a first aperture and a second, larger, aperture that each allow a portion of the occluded UV light to instead pass through the occlusion plate and contribute to the uniform UV illumination pattern cast on the expected target disinfection area.

In some embodiments, the occlusion nose includes a pair of fins extending outwardly from the occlusion plate. The inner surface, facing the opening, of each fin is UV reflective. Further, the surface area and orientation of each relative to the opening are configured to reflect a portion of the UV light from the opening toward the expected target disinfection area such that the reflected UV light contributes to the uniform UV illumination pattern cast on the expected target disinfection area.

In some embodiments, the target disinfection area includes top rear corners of a keyboard and the housing is disposed near a perimeter of the keyboard at a height above the keyboard oriented at a downward angle such that the opening points toward the keyboard. The keyboard substantially corresponds with the target disinfection area and the reflected UV light contributes to the uniform UV illumination pattern cast on the expected target disinfection area at the top rear corners of the keyboard.

In general, another innovative aspect of the subject matter described in this specification can be embodied in a UV disinfection device having a sensor system. The UV disinfection device includes a housing and a UV-C light source disposed within the housing configured to emit UV-C light. A lens is configured to direct UV-C light from the UV light source through a major opening in the housing toward a target disinfection area. The device also includes a sensor system with multiple sensors electrically coupled to a control circuit. The sensors dual passive infrared motion sensors disposed in the housing and configured to receive infrared energy through minor openings in the housing disposed on opposite lateral sides of the main opening; an accelerometer; a gyroscope; and a time of flight sensor.

The foregoing and other embodiments can each optionally include one or more of the following features, alone or in combination. In particular, one embodiment includes all the following features in combination.

In some embodiments, the control circuit is configured to set a ready to clean flag in response to detecting a combination of different sensor output patterns from two or more of the accelerometer, the gyroscope, the dual passive infrared motion sensors, and the time of flight sensor. The sensor output patterns may be indicative of a plurality of discrete events, such as an errant event, a touch event, a wiping event, a non-disinfection-related event, a walk by event, a key touch event, a mouse click event, a mouse movement event, a cleaning event, an occupancy event, a presence event, and a proximity event.

In some embodiments, the control circuit is configured to detect a key touch pattern from output of the accelerometer. In some embodiments, the control circuit is configured to detect a sequence of key touches based on a combination of accelerometer output and output from the dual passive infrared motion sensors. In some embodiments, the control circuit is configured to detect a key press of a key of a keyboard having a plurality of keys based on output from the accelerometer without detecting which of the plurality of keys was pressed.

In some embodiments, the control circuit is configured to detect a mouse click based on a sensor output pattern from the accelerometer. In some embodiments, the control circuit is configured to detect a mouse movement and clicks based on sensor output patterns from the dual passive infrared motion sensors and the accelerometer.

In some embodiments, the control circuit is configured to detect a wiping motion for cleaning based on a combination of sensor output patterns from the dual passive infrared motion sensors and the accelerometer.

In some embodiments, the control circuit is configured to interrupt a disinfection cycle in response to detecting presence with any of the plurality of sensors by deactivating the UV source.

In some embodiments, the control circuit is configured to detect a walk by pattern based on a sensor output from the dual passive infrared motion sensors.

In some embodiments, the control circuit is configured to detect events based on detecting different patterns in the sensor output from two or more of the plurality of sensors of the sensor system and configured to track a number of interruptions of disinfection cycles of the UV-C source by source of interruption.

In some embodiments, the control circuit is configured with a progressive delay mode that increases a delay time before initiating a disinfection cycle after a lack of human presence is detected, wherein progressive delay mode is activated in response to disinfection cycle interruptions exceeding a threshold. While progressive delay mode is activated, the control circuit can be configured to increase the delay time exponentially based on a disinfection cycle interruption counter. The progressive delay mode can be deactivated in response to completion of two full disinfection cycles without interruption.

The control circuit is configured to track dosage over unit of time and in response to dosage over unit of time exceeding a threshold, lower UV disinfection dosage.

In some embodiments, the control circuit includes a UV driver to control operation of the UV-C source, wherein the control circuit is configured to correct UV-C source intensity over the life of the UV-C source by increasing the voltage supplied to the UV-C source to compensate for loss of intensity over the life of the UV-C source.

In some embodiments, the control circuit is configured to monitor the gyroscope sensor output and deactivate the UV-C source in response to detecting an attitude parameter change past a guard band limit from an attitude parameter calibrated during installation.

In some embodiments, the control circuit is configured to detect lack of presence based on sensor output from a first sensor of the plurality of sensors and configured to detect lack of presence based on sensor output from a second sensor of the plurality of sensors, wherein the control circuit is configured to initiate a delay timer in response to detecting lack of presence from the first sensor without detecting lack of presence from the second sensor.

In some embodiments, the control circuit is configured to confirm the lack of presence with the second sensor after initiating the delay timer and before the delay time completes, whereby the lack of presence is detected quickly and confirmed by the second sensor before activation of the UV-C source.

In general, another innovative aspect of the subject matter described in this specification can be embodied in a UV disinfection device having a control circuit and certain sensors that are configured to provide novel functionality within a disinfection framework.

The foregoing and other embodiments can each optionally include one or more of the following features, alone or in combination. In particular, one embodiment includes all the following features in combination.

In some embodiments, the disinfection device includes a gyroscope. At installation, a UV-C meter can verify suitable UV-C measurement output in proximity to the disinfection device, including a uniform intensity of UV-C light cast on the target disinfection area and in response gyroscope attitude measurements can be taken and saved in memory. In operation, the control circuit can monitor the gyroscope sensor output and in response to detecting a change in attitude measurements beyond a guard-band deactivate the UV source and prevent further re-activation of the UV source, for example until the disinfection device can be recalibrated for its new attitude and pass a safety verification test.

In some embodiments, the disinfection device includes an accelerometer configured with sufficient sensitivity to detect touch at a surface in proximity to the disinfection device. The disinfection device being indirectly physically coupled to the touch detection surface. The disinfection device can be indirectly coupled to multiple touch surfaces in proximity and the control circuit can be configured to detect which touch surface was touched based on the accelerometer sensor output. The control circuit can be configured to detect events based on the accelerometer sensor output or a combination of accelerometer sensor output and other sensor output front other sensors.

In some embodiments, the disinfection device includes dual passive infrared sensors. The dual passive infrared sensors may be installed within the housing of a disinfection device and configured to receive infrared energy through openings in the housing through IR transmissive or transparent covers that are configured to block environmental noise, such as wind, from negatively impacting the dual PIR sensor output. The dual passive infrared sensors may be positioned on opposite sides of the disinfection device such that passive IR energy is received at one PIR sensor before the other and the control circuit can detect lateral human movements, or gestures, or other events based on patterns in the dual PIR sensor output, or a combination of the dual PIR sensor output and other sensor output from other sensors.

In some embodiments, the disinfection device includes a time of flight sensor. The time of flight sensor can transmit an active infrared signal and provide sensor output indicative of the time for the active infrared signal to strike an object and return. The time of flight sensor can be configured to detect human presence in proximity of the disinfection device, such as at a computer workstation or medical cart. The time of flight sensor can be configured for detecting a lack of human presence.

The various aspects and embodiments of the UV disinfection platform provide an intelligent, automated UV-C light disinfection system that can continuously monitor surfaces to detect when disinfection is warranted and automatically disinfects hundreds of times per day without any assistance from staff. Bacteria levels can be reduced by more than 99 percent on surfaces equipped with the disinfection platform.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

FIGS. 18A-B illustrate representative top and side views of a time of flight sensor of a disinfection apparatus detecting human presence.

FIG. 19 illustrates an exemplary graph of microphone output data including a pattern indicative of keyboard key presses.

FIGS. 27A-B illustrate exemplary side and front views of one embodiment of a disinfection apparatus including a support base with a ledge for disposing a mobile device.

FIGS. 28A-B illustrate exemplary side and front views of the disinfection apparatus of FIGS. 27A-B with a mobile device disposed on the ledge.

DESCRIPTION OF THE CURRENT EMBODIMENT

Figure 1:
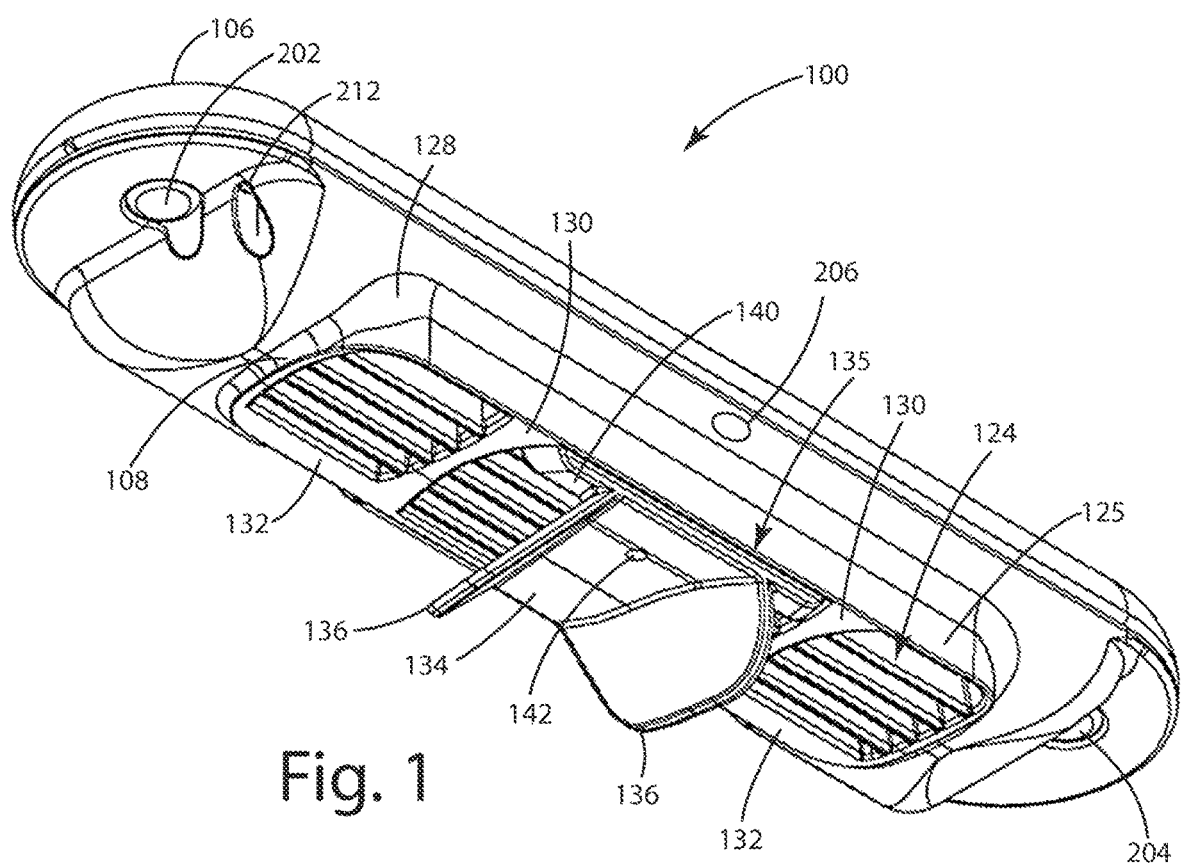
FIG. 1 illustrates a perspective view of a disinfection apparatus of the present disclosure.
Figure 2:
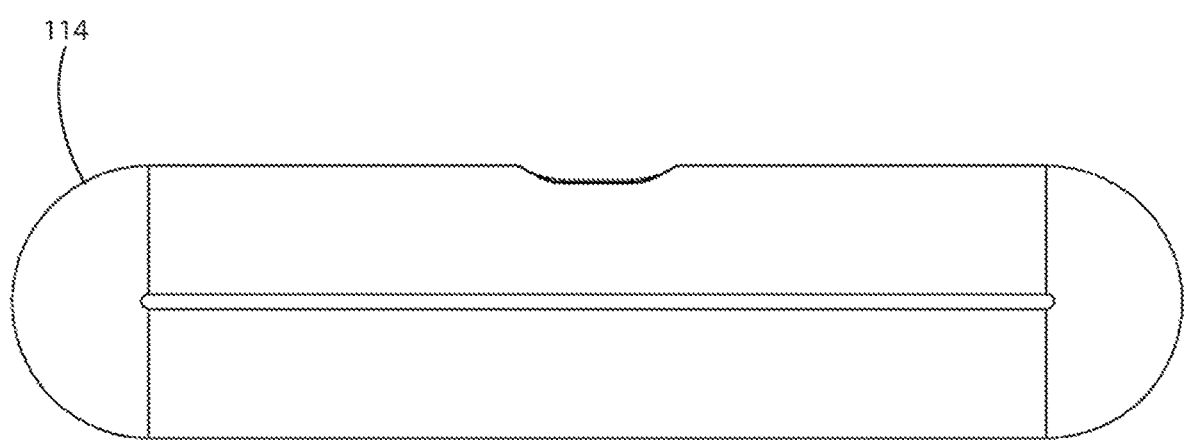
FIG. 2 illustrates a top view of the disinfection apparatus.
Figure 3:
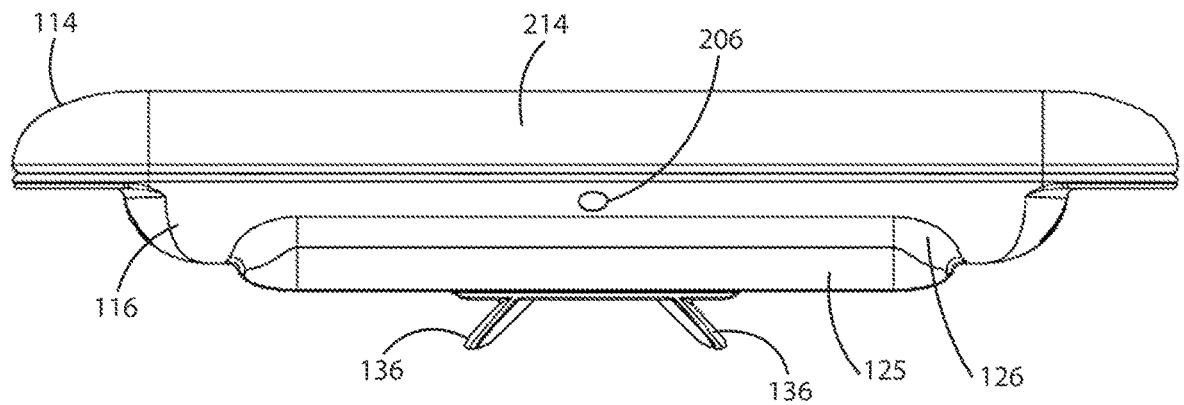
FIG. 3 illustrates a front view of the disinfection apparatus.
Figure 4:
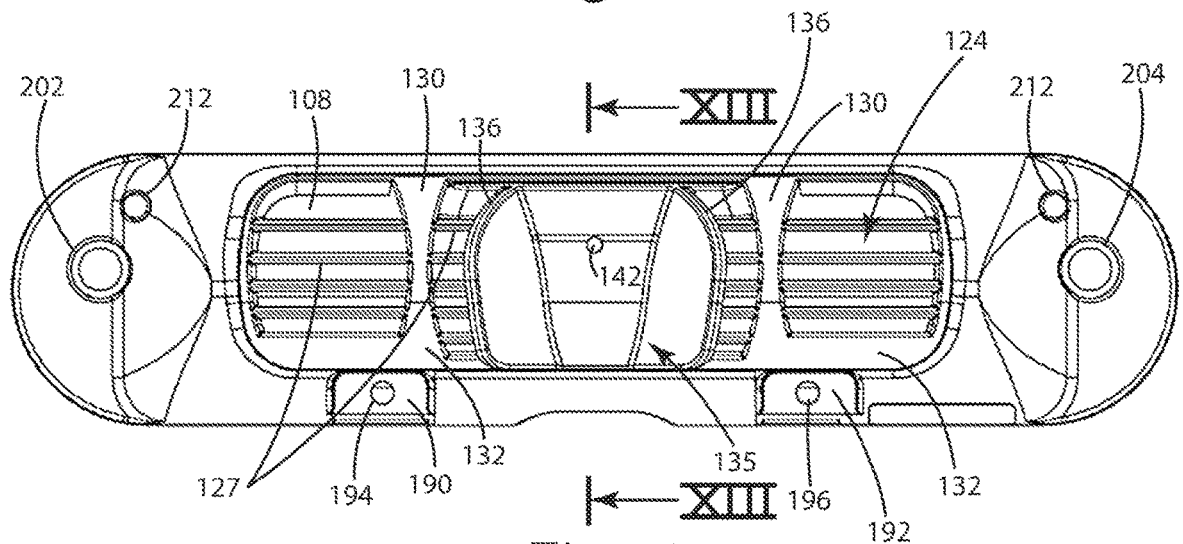
FIG. 4 illustrates a bottom view of the disinfection apparatus.
Figure 5:
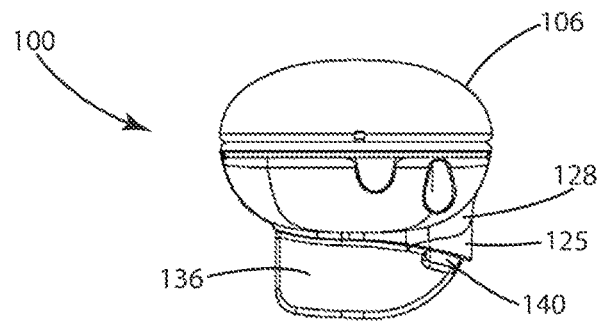
FIG. 5 illustrates a side view of the disinfection apparatus.

With respect to exemplary embodiments illustrated in FIGS. 1-14, a disinfection apparatus is generally shown at reference identifier 100. Typically, the disinfection apparatus 100 is configured for at least partially disinfecting a target disinfection area such as a surface. For example, the apparatus 100 can be configured to disinfect a human interface surface of a device or other piece of equipment, which can include a human touch surface. The disinfection apparatus 100 can include a housing 106 that defines an aperture 108. The housing 106 can include a first, top, portion 114 and a second, bottom, portion 116 that are configured to be joined together to form the housing 106.

Figure 6:
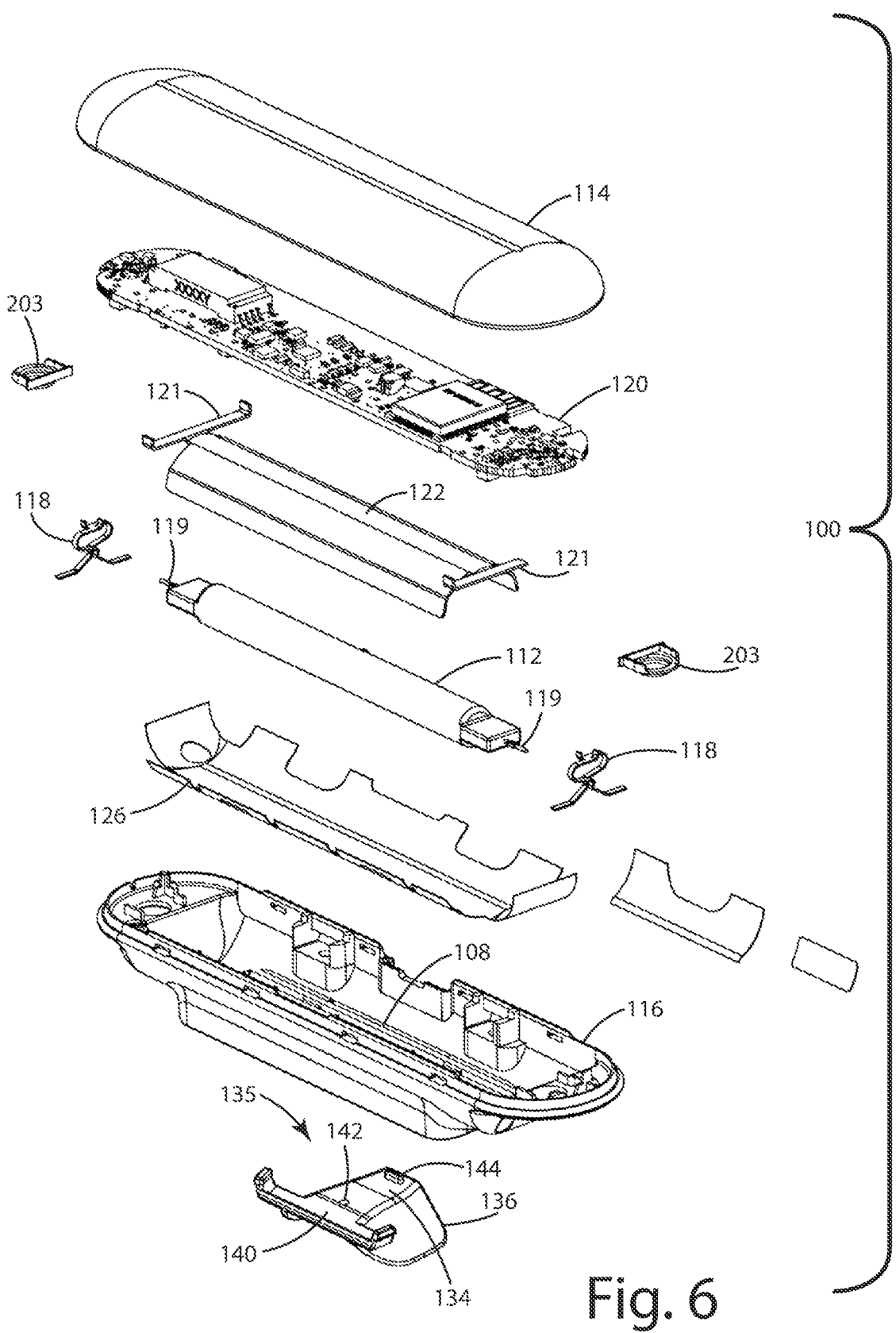
FIG. 6 illustrates a perspective exploded view of the disinfection apparatus.

Perhaps as best shown in the exploded perspective view of FIG. 6, the disinfection apparatus 100 can further include an ultra-violet (UV) light source 112 that can be at least partially enclosed in the housing 106. The UV light source 112 can be retained in place within the housing by two retaining clips 118 that physically fix the UV light 112 in place within the housing and also electrically couple the terminals 119 of the UV light source to the circuit board 120. A reflector 122 can also be disposed within the housing 106.

Figure 10:
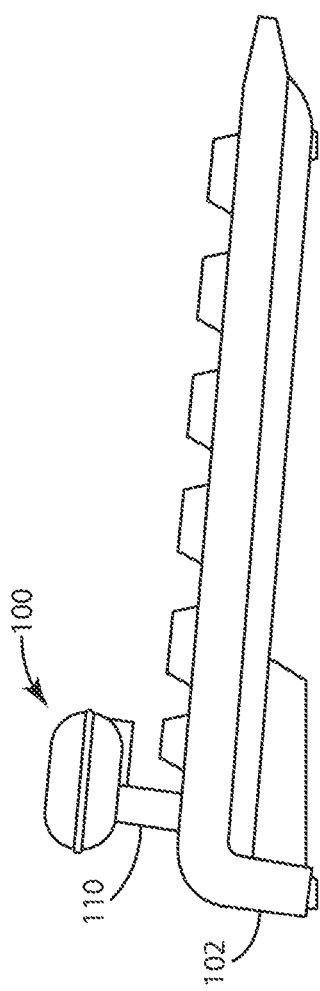
FIG. 10 illustrates a side perspective view of a disinfection apparatus including an attachment device attached to a keyboard.
Figure 11:
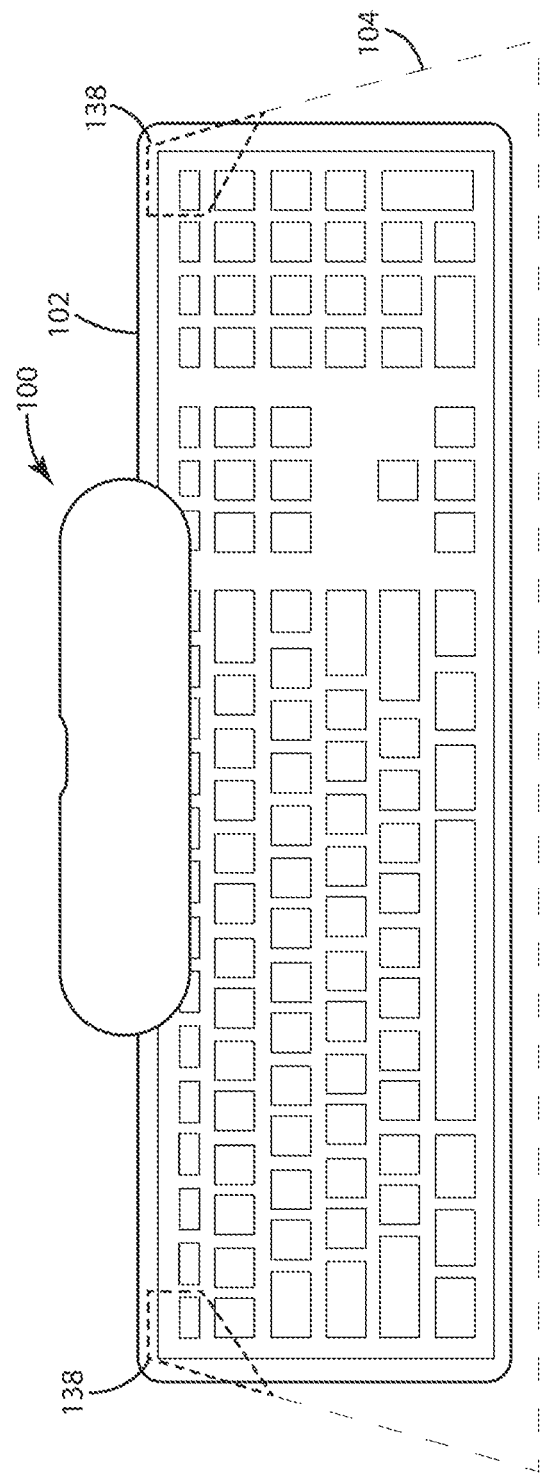
FIG. 11 illustrates a top view of the disinfection apparatus and UV illumination pattern cast on a target disinfection area substantially covering a keyboard.
Figure 12:
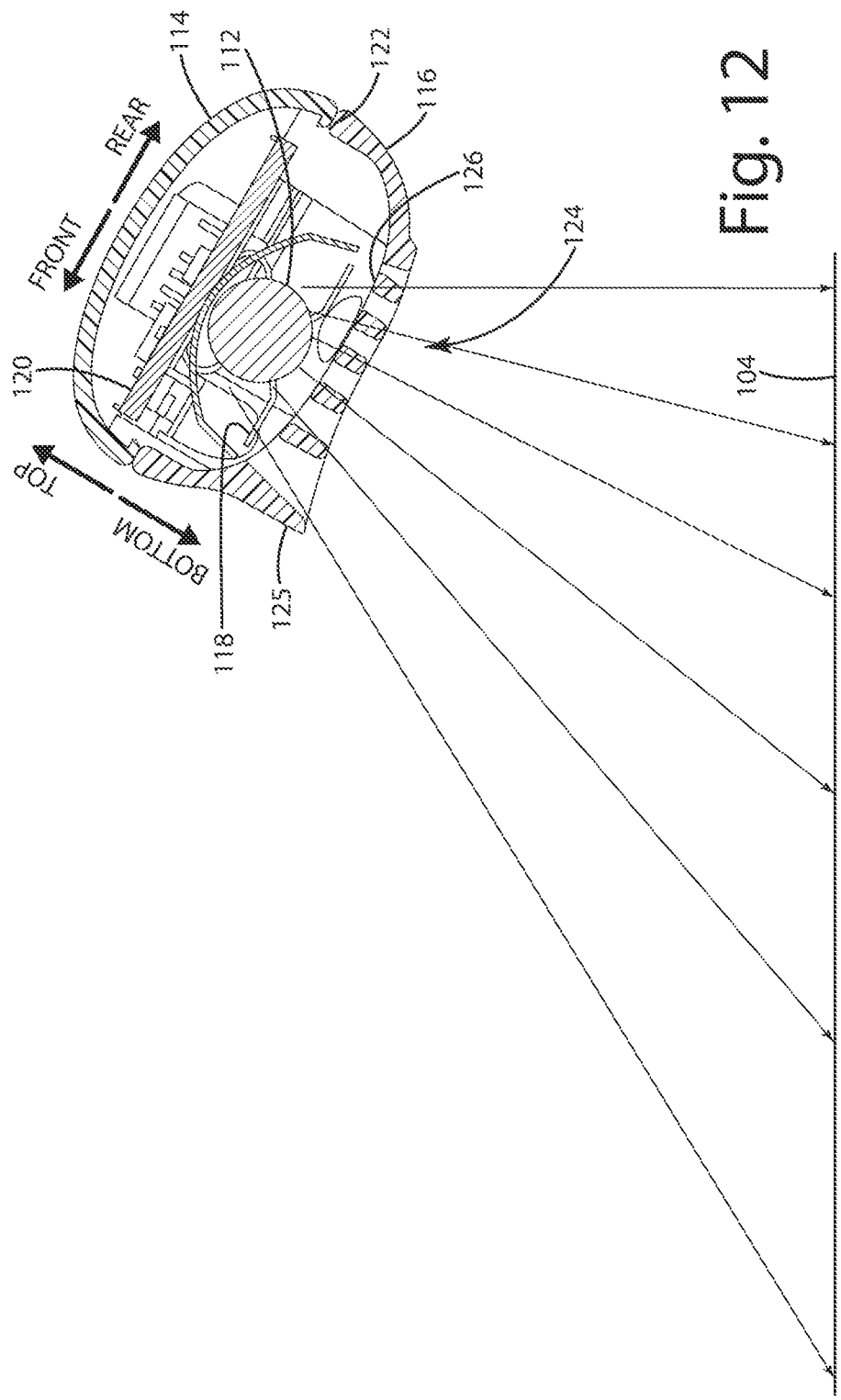
FIG. 12 illustrates a representative side view of a disinfection apparatus without an occlusion nose casting a UV illumination pattern toward a target disinfection surface.
Figure 13:
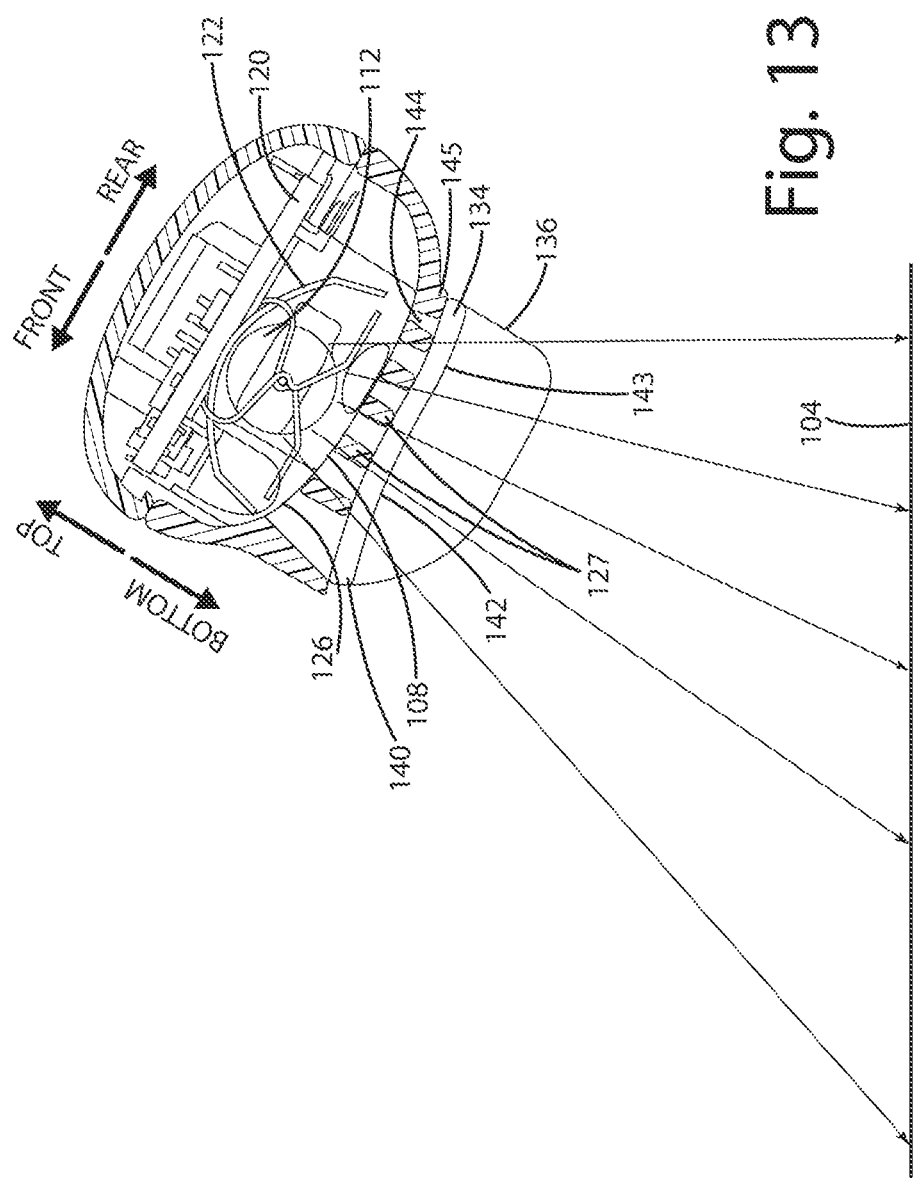
FIG. 13 illustrates a representative side view of a disinfection apparatus with one embodiment of an occlusion nose casting a UV illumination pattern toward a target disinfection surface.

The UV light source 112 can project an illumination pattern toward a target disinfection area 104. The disinfection device 100 can be configured such that the UV light source 112 projects an illumination pattern that substantially corresponds to an expected target disinfection area 104, such as the touch surface of a human interface device, for example keyboard 102 as shown in FIG. 11. The UV illumination pattern can be influenced and defined, at least partially, by the aperture 108. For example, the aperture 108 of the depicted embodiments is generally stadium shaped and the elongated UV light source 112 is generally aligned both longitudinally and laterally with the opening of the aperture 108 such that the illumination pattern is generally restricted to the general shape of the aperture. However, because the disinfection device 108 is typically offset and raised relative to the target disinfection area, for example as shown in the embodiments of FIGS. 10-14, the disinfection device casts a UV illumination pattern at an angle relative to the expected target disinfection surface. As such, while the UV illumination pattern through the aperture 108 (without considering the other UV pattern influences) is a generally stadium shape that is elongated at the target disinfection area due to the orientation of the disinfection device relative to the surface the pattern is being cast upon. In addition, the intensity distribution of the UV illumination pattern generally forms an elliptical shape where the intensity of the UV illumination pattern maps to the elongated shape of the UV source and fades laterally and longitudinally, falling off a bit quicker toward the longitudinal edges because the elongated shape of the UV source provides an increased intensity along the lateral axis.

The UV illumination pattern can also be influenced and defined, at least partially, by any optics in the path of the UV light projection, such as reflector 122, lens 126, louvers 124, louver frame 128, eyebrow 125, nose 135, or any combination thereof. The optics, either alone or together in various combinations, can perform a variety of different functions including UV pattern control, UV pattern shaping, UV pattern extension, UV pattern redirection, UV pattern exclusion, UV intensity limiting, UV intensity smoothing, UV line of sight limiting, and UV dosage control. These functions can be achieved by forming the various components from UV transmissive, UV transparent, UV reflective, UV opaque materials, or combinations thereof, such as various polymer, metal, composites, or other materials. The optics can be designed for a more homogenous pattern. The optics can perform these various functions in a variety of different ways, for example by obstructing UV light, reflecting UV light, refracting UV light, absorbing UV light, redirecting UV light, occluding UV light, or any combination thereof. The UV illumination pattern received at the opening 108 can be occluded by a portion of the UV illumination pattern caused by one or a combination of multiple different optical occlusions positioned within the opening 108 including the louvers 127, louver frame 128, eyebrow 125, occlusion plate 134, and reflective fins 136. Further, the UV illumination pattern output by the disinfection device can be shaped by a UV-C illumination pattern shaping system that extends from the opening 108. The UV-C illumination pattern shaping system can include one or more of louvers 127, louver frame 128, eyebrow 125, occlusion plate 134, and reflective fins 136. Specifically, the UV-C illumination pattern shaping system can receive UV-C light from the opening 108 and shape the UV-C illumination pattern into a shaped UV-C illumination pattern for casting on to an expected target disinfection area or surface. The shaped UV-C illumination pattern can be shaped to have characteristics such that when cast onto the expected target disinfection surface or area the resultant UV-C illumination pattern on the area or surface has a generally uniform intensity. That is, the shaped UV-C illumination pattern characteristics account for the orientation and position of the disinfection device relative to the expected target disinfection area and the disinfection device includes optic features, such as the UV0C illumination pattern shaping system extending from the housing to adapt the UV light to provide the shaped UV-C illumination pattern such that when cast on the expected target disinfection surface at the expected distance and position relative to the disinfection device, the UV illumination pattern is relatively uniform.

The uniformity of the intensity of a UV light pattern cast by a disinfection device can vary depending on a number of different factors. Two such factors are the characteristics of the UV light pattern output from the disinfection device and the distance to the target disinfection area. It is worth noting that the contour of the target disinfection surface can affect the distance and therefore the ultimate intensity at the target disinfection area. Distance is a factor because of the inverse square law, which states that illumination intensity changes in inverse proportion to the square of the distance from the source. In simple terms, for a given illumination pattern, as the distance from the source doubles, the light intensity falls off by four times. This means that for a plane adjacent to an omnidirectional light source, the light pattern on the plane will tend to have highest intensity where the light source is closest and then quickly fall off in all directions away from that point because as distance between the light source and the plane increases, the intensity of the light will drop.

In practice, the intensity of a UV illumination pattern is more complex. The UV source may not be omnidirectional and the target disinfection area likely is not a plane adjacent to the source. The UV source may include multiple discrete sources, the shape of the source may be elongated, the UV light may interact with a reflector, a lens, an occlusion, directional louvers, or a combination thereof. For example, where the UV lamp is elongated, the UV light pattern tends to have highest intensity in the middle, with the intensity fading quicker in the longitudinal directions than in the latitudinal directions due to the elongated shape of the lamp. Further, the UV source may be offset and cast its pattern at a downward angle toward a target disinfection area. The target disinfection area may itself have a varied contour, such as a keyboard, mouse, or other type of irregular surface. Accordingly, to provide a relatively uniform intensity at a target disinfection area, the UV illumination pattern output from the disinfection device likely will have a non-uniform intensity pattern—and more particularly, a UV illumination pattern with a non-uniform intensity selected such that the UV illumination pattern once it reaches an expected target disinfection area will have a generally uniform intensity given the expected target disinfection area being within a certain distance with respect to the disinfection device and certain orientation with respect to the disinfection device.

For example, the disinfection device can be configured to provide a UV illumination pattern that produces a relatively uniform intensity pattern at an expected disinfection area where the disinfection device is disposed a few centimeters above the edge of the expected target disinfection area and the opening is angled downward at about 30-45 degrees toward the expected target disinfection area. Of course, the disinfection device can be configured to output a different UV illumination pattern that produces a relatively uniform intensity pattern where the disinfection device is disposed at a different height and different orientation relative to a different expected target disinfection area. That is, for a range of heights and orientations relative to an expected target disinfection area (e.g., a flat surface, an inclined surface, a keyboard and mouse, a keyboard alone, a desk surface with various accessories, a chair, a cabinet, a handle, a cart, a phone, a sink, a countertop, or essentially any other area or surface where the disinfection device may be installed to provide repeatable automated disinfection) the optical occlusion (e.g., louvers, eyebrow, and occlusion plate, occlusion plate with or without apertures, and occlusion plate with fins reflector or not, and any combination thereof) occludes a portion of the UV light such that the UV illumination pattern cast on the expected target disinfection area has uniform intensity. It should be understood that uniform intensity does not require all intensity values to be precisely equal, but rather that the intensity at the expected target disinfection area is substantially more uniform than without the optical occlusion. In one example, the expected target disinfection area is a keyboard and the UV disinfection device is mounted a few centimeters above the top of the keyboard (for example, as shown in FIGS. 10-11). In this embodiment, the UV disinfection device is configured to output a UV illumination pattern such that minor variances in the contour of the keyboard, for example due to the incline and shape of the keyboard (or due to keyboard kickstands being extended or not) relative to the position and orientation of the UV disinfection device 100 maintain a relatively uniform intensity over the entire expected target UV disinfection area 104 covering the keyboard. In one embodiment, a uniform intensity is provided in a range between 40 $\mu W/cm^2$-80 $\mu W/cm^2$ across the entire target disinfection area. In some other embodiments, a UV illumination pattern is deemed to have a generally uniform intensity where the radiant power values across the area are within 5%-10% of each other. It should be understood that providing a uniform UV pattern at a target disinfection area may involve configuring the disinfection device to provide a non-uniform UV illumination patter at its output.

A reflector 122 can be interposed between the circuit board 120 and the UV light source 112 to protect the circuit board 120 from exposure to UV light and reflect UV light toward the opening 108 in the housing. The reflector 122 can include retaining members 121 that pinch the edges of the circuit board 120 fixing the reflector in place within the housing 106. The shape, size, reflectivity, and other characteristics of the reflector can vary depending on the application and depending on the characteristics of the other components. In the current embodiments, the reflector 122 forms an arc around the length of the UV source such that a majority of the UV light emitted by the UV source 112 is directed toward aperture 108.

A UV lens 126 having a defined set of optical properties that influence the UV illumination pattern can be disposed on the disinfection apparatus 100 between the UV light source 112 and the target disinfection area 104. In the current disclosure, the UV lens 126 is a flexible UV film 126 that covers the opening 108 and is adhesively coupled to the internal surface of the lower portion of the housing 116 to seal the internal cavity of the housing 106. The UV lens 126 can be configured to direct UV light from the UV light source 112 through the opening 108 generally, and more specifically through the spacing between the louvers 124.

The seal provided by the UV lens 126 provides protection. For example, should a component break within the housing 106, the UV film 126 can prevent broken component pieces from falling out as well as gas or liquid from leaking out of the cavity of the housing through the opening 108. The UV film 126 can also prevent unwanted foreign objects or fluids from reaching the components in the internal cavity of the housing 106.

The properties of the UV lens 126 can be selected and enhanced by loading the lens with additives, applying a UV blocking pattern, varying the UV lens material, thickness, shape, layering, surface texture, or any combination thereof. The optical properties for the UV lens can assist in distributing the UV light in a generally uniform UV light pattern across the target disinfection area 104. A more uniform UV light pattern can reduce or prevent UV hot spots, which can cause discoloration or other damage from forming on the UV lens or at the target disinfection area. Some embodiments provide a UV lens with diffusal properties that cause the UV light to diffuse or disperse across the surface of the target disinfection area, such as a user interface surface. Examples of some of the UV lenses capable of incorporation into various embodiments of the disinfection device 100 of the present disclosure are described in U.S. provisional patent application 62/924,324, filed on Oct. 22, 2019, to Baarman, entitled "OPTICAL PROPERTIES AND METHODS FOR UV TREATMENT", which is incorporated by reference in its entirety.

A louver system 124 including a louver frame 128 and directional louvers 127 can be disposed within the opening 108 in the housing 106 to influence the UV illumination pattern output by the disinfection apparatus 100. Referring to the sectional view of FIG. 12, the disinfection device when oriented toward a target disinfection area 104 below and in front of the disinfection device, a user with their eye level at or above the disinfection device does not have a direct line of sight to the UV light source. Further, the dynamic progression of the louvers 127 further limits the direct line of sight such that even where a user's eye level is below the disinfection device, there is no direct line of sight to the UV light source. In addition, the dynamic spacing between the louvers 127 increases the uniformity of the UV illumination pattern by providing more spacing between the louvers toward the front of the disinfection device where the illumination pattern is configured to travel farthest to reach the target disinfection area 104 and less spacing between the louvers 127 toward the rear of the disinfection device where the illumination pattern is configured to travel closest to reach the target disinfection area 104.

The louver system 124 can cover, at least in part, the opening 108. Specifically, the opening 108 can be outlined by a louver frame 128 that can limit the direct line of sight from the UV light source 112 to the user and influence the UV illumination pattern output by the disinfection apparatus 100. The louver frame 128 can include an eyebrow 125 that projects from the front portion of the louver frame 128 in a direction away from the opening 108. Further, the louver frame 128 can support the louvers 127. The louver frame 128 of the illustrated embodiment separates the louvers 127 into three sets with two latitudinal frame sections 130 that span from the rear of the louver frame 128 to the front of the louver frame 128 where the eyebrow 125 is located. The thickness of the latitudinal louver frame sections 130 can vary from the rear to the front such that the thickness frame sections 130 create a flush surface with the bottom of the eyebrow 125. The two latitudinal frame sections 130 split the louvers 124 into three sets, two side sets of four louvers and a middle set of five louvers. The profile of the latitudinal frame sections 130 walls can be curved to influence the UV illumination pattern through the opening 108 and contribute to providing an increase in uniformity of the UV illumination pattern at the target disinfection area. For example, the profile of the latitudinal frame sections 130 in the depicted embodiment are generally concave. The louver frame 128 of the illustrated embodiment also includes longitudinal louver frame sections 132. These longitudinal louver frame sections 132 block UV light from exiting toward the rear of the opening 108, and specifically from the side-rear sections of the opening 108. The two longitudinal frame sections 132 span from one side of the louver frame 128 toward the middle of the louver frame to meet the latitudinal frame sections 130, respectively. The profile of the longitudinal frame sections 130 influence the UV illumination pattern through the opening 108 and contribute to providing an increase in uniformity of the UV illumination pattern at the target disinfection area. For example, the profile of the longitudinal frame sections 130 in the depicted embodiment are generally planar and block UV light closest to the target disinfection area that is apt to receive the highest intensity UV light from the source on account of being closer. Accordingly, the louver frame 128 covers portions of the opening 108 and influences the UV illumination pattern therethrough from the UV light 112. Alternative embodiments can have a different louver frame configuration and different configuration of louvers including additional, fewer, or no louvers and louver frame at all.

A UV opaque nose 135 can occlude a portion of the UV illumination pattern from opening 108. Blocking, reflecting, or absorbing a portion of the UV illumination pattern can increase the uniformity of the intensity of the UV illumination pattern at a target disinfection area. The UV opaque nose 135 is an application specific optic for controlling uniform dose. The nose is removable and replaceable element. Further, it can include a reflective surface for casting design specific patterns.

By positioning the nose 135 near the center of the opening 108, the highest intensity portion of the UV illumination pattern can be occluded. The resultant UV light pattern having two higher intensity side sections with a middle section that has no or low intensity in the middle. This intensity non-uniformity at the output of the disinfection device generally translates to an increase in uniformity at the target disinfection area. While such a UV light pattern may be an improvement over some UV light patterns, the nose 135 can include a variety of different features tailored to increase the overall intensity uniformity of the UV light pattern at the target disinfection area.

The shape of the nose can be tailored to limit UV intensity in the latitudinal direction as well as the longitudinal direction. In the depicted embodiment, it includes a generally isosceles trapezoid UV opaque plastic plate 134 with two UV opaque plastic fins 136 that extend from the trapezoid legs at about a 45 degree angle in a direction away from the midpoint of the disinfection device. Together with the louver frame sections 130, the UV opaque plate 134 occludes much of the middle portion of the UV illumination pattern output from the opening 108.

Figure 23:
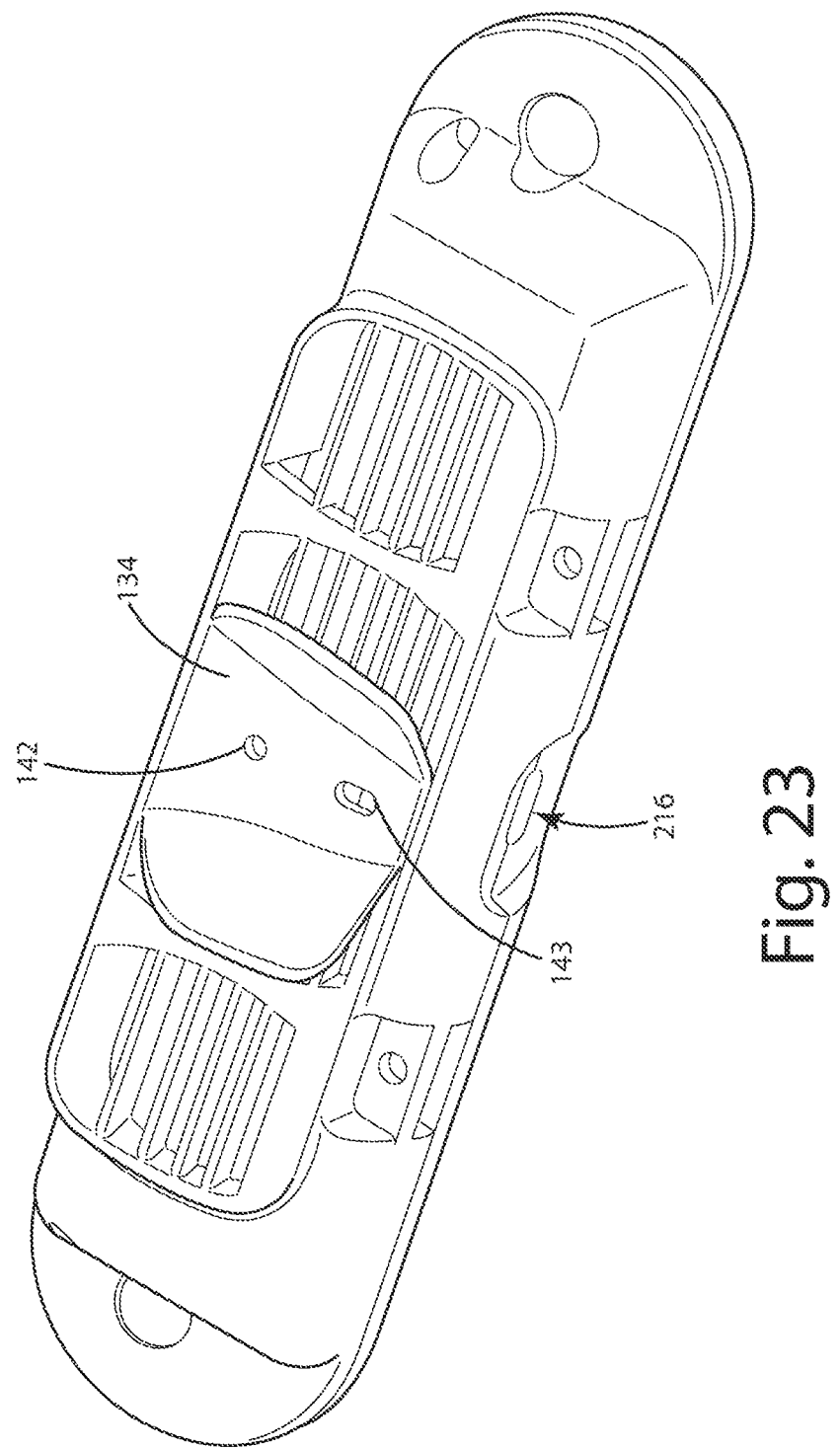
FIG. 23 illustrates a perspective bottom view of a disinfection device having one embodiment of a occlusion nose.

The plate 134 can include an aperture 142 to limit UV dosage over the occluded area. The aperture 142 can be configured to increase uniformity of intensity of the UV illumination pattern at an expected target disinfection area, for example an expected target disinfection area within a particular distance range away from the disinfection device where the disinfection device is oriented within a particular angle with respect to the target disinfection area. The aperture 142 can be configured by adjusting at least its size, shape, and positioning in the plate 134. For example, the aperture 142 can be latitudinally positioned toward the top third of the trapezoidal plate 134, and be a circular shape having a diameter of about 0.25 millimeters. In alternative embodiments, depending on the application including, for example, the expected position and orientation of the disinfection device, the aperture 142 can have a different size, shape, position, or any combination thereof. In one alternative embodiment illustrated in FIG. 13 and FIG. 23, an additional aperture 143 is included in an plate 134. The additional aperture 143 is latitudinally positioned toward the bottom third of the plate 134 and has a stadium shape with about double the area of the other aperture 142. This additional aperture can assist in ensuring the target disinfection area receives sufficient UV light to provide disinfection according to any one of a number of UV standards. The angle of an aperture through a surface having a thickness can also affect the UV light, which affects the overall UV illumination pattern from the disinfection device. For example, the occlusion nose 134 while having a generally trapezoid outline, may not be flat, but instead include convex and concave portions formed either by varying the thickness of the structure or the structure including a contour. This can perhaps most easily be seen in the sectional view of FIG. 13, which shows the apertures 143, 142 and the wavy face of the occlusion nose 135. The contouring can also be seen in FIG. 23, as well as in FIG. 1 depicting the embodiment with one aperture 142. The various characteristics of the aperture(s) can be selected to increase uniform intensity of the UV illumination pattern at an expected target disinfection area for an expected position and orientation of the disinfection device with respect to an expected target disinfection area. In one exemplary embodiment, the aperture 142 characteristics and other disinfection device characteristics provide a 2 microwatt intensity level baseline in the middle region of the target disinfection area.

The fins 136 can be formed from a UV reflective material, include a layer of UV reflective material, or have a UV reflective coating on a base substrate that may or may not be UV transmissive such that the inwardly facing side of each fin that faces the opening 108 can reflect UV light incident thereto. The portion of UV light output from the opening 108 incident with the reflective fins influences the UV illumination pattern output from the disinfection device. to shape the UV pattern. For example, as shown in FIG. 11, with the disinfection device disposed and oriented as shown, the UV illumination pattern 104 covers the entire keyboard including the lateral corners 138 near the top of the keyboard 102 that without the reflective fins would not receive UV light. The orientation, shape, and size of the fins can vary depending on the application and the desired UV illumination pattern shape. While the illustrated embodiment includes reflective fins, it should be noted that alternative embodiments of the occlusion nose may not include fins, or may forgo the reflective coating and merely provide occluding fins that do not reflect UV light.

Figure 14:
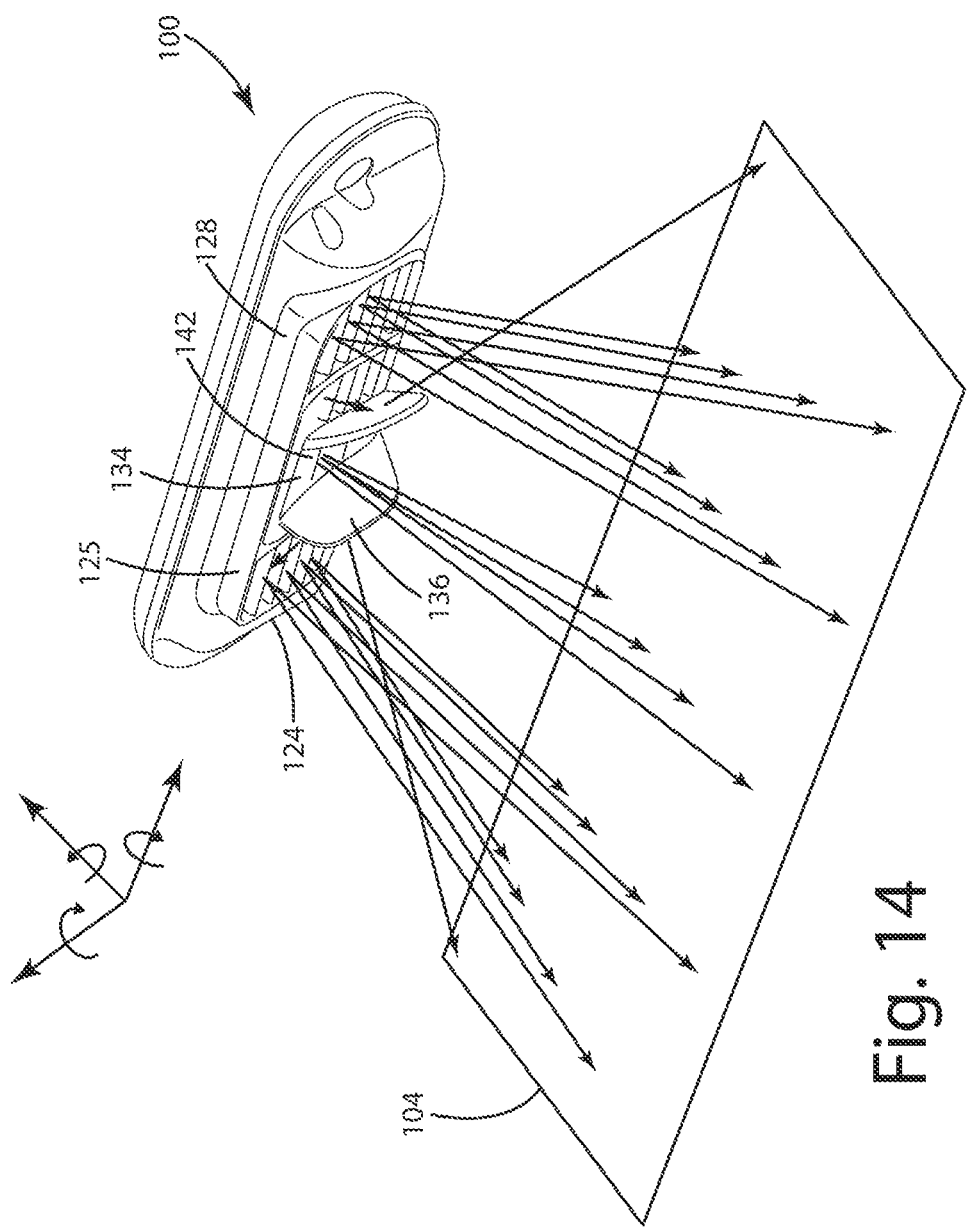
FIG. 14 illustrates a representative perspective view of a disinfection apparatus casting a UV illumination pattern shaped by reflective fins.

Another example of the UV illumination pattern of the disinfection device 100 is shown in FIG. 14. In order to illustrate the UV illumination pattern a few representative rays of light are illustrated with arrows showing the path of light traveling from the disinfection device to the target disinfection area 104. The perspective view of FIG. 14 in particular illustrates one ray of light bouncing off of each reflective fin 136 and hitting the rear corner areas of the target disinfection area/surface. Without the reflective fins 136, the UV illumination pattern does not effectively reach these corners. FIG. 14 also illustrates the UV light through aperture 142, which provides a baseline UV intensity in the middle region of the target disinfection area. In total, after accounting for the inverse square losses and other UV illumination pattern modifiers, the overall UV intensity at the target disinfection surface is more uniform than other UV disinfection apparatuses. Further, it should be understood that the UV illumination pattern can be configured to provide a uniform intensity at the particular contour expected at the target disinfection surface. For example, where the target includes a keyboard and mouse, the UV illumination pattern can be adapted by configuring the various components of the disinfection device to provide an intensity level that is uniform over that particular contour and expected surface within a particular range of intensity values, for example provided by a lux meter.

The occlusion nose 135 can be removably joined to the disinfection device. In the illustrated embodiments, the occlusion nose 135 includes a lateral member 140 that snap-fits with the lateral louver frame sections 130. Each end of the lateral member 140 includes a cantilever beam with a hook on the end that snap-fits to a respective receptacle formed by the edge of each of the louver frame sections 130. The hooks can be contoured to match the contour of the receptacle of the respective louver frame section 130. In operation, the cantilevers undergo displacement as they traverse the receptacle and once the hook is fit in place, the cantilevers relax to provide a snap-fit. Although the illustrated embodiment is joined by snap-fit, other embodiments can removably join the occlusion nose 135 with a different fastening system. Further, in some embodiments, the occlusion nose may be integrally formed with the disinfection device or a portion thereof, or may be omitted. Different occlusion noses can be joined to the disinfection device depending on the position and orientation of the disinfection device relative to the target disinfection area. For example, different occlusion noses may be utilized if the disinfection device is to be mounted near a keyboard, on a monitor, or on a cabinet, to name a few examples. In the embodiment depicted in FIGS. 1-12, the occlusion plate 134 can include a member 144 that extends out of its back that interfaces with the louvers 124. Specifically, the member 144 can be configured for reception by a suitable receptacle 145 formed by the louvers 24 and assist in locating the occlusion nose 135 in its proper place. In addition, the member 144 may assist in removably joining the nose 134 to the disinfection device. In some embodiments, the occlusion nose does not include such a friction member and the louvers 124 do not include a receptacle for receiving same.

The disinfection apparatus 100 housing 106 can include a coupling mechanism for attaching the disinfection apparatus to an attachment device. In the depicted embodiments, the housing 106 includes a pair of mounting surfaces 190, 192, each having a mounting hole 194, 196 for fastening the attachment device 110 thereto, for example utilizing bolts and nuts, or essentially any other type of fastener. One example of an attachment device 110 for use in connection with the disinfection apparatus is illustrated in FIGS. 10-11. One end of the attachment device 110 couples to and extends from the housing 106, as depicted in FIG. 10. The other end of the attachment device 110 can be configured to removably attach to a human interface device, a stand, cabinet, or other support structure. For example, in FIG. 10, the other end of the attachment device 110 is coupled to the keyboard 102. The position (including lateral position and height relative to the keyboard) as well as the orientation of the disinfection device can vary depending on the application and particular configuration of the disinfection device. The particular position and orientation depicted in FIGS. 10-11 represents one embodiment. In other embodiments, the positioning and orientation of the disinfection device can be installed in a different position and orientation. Such position and orientation can be fixed or selectively adjustable.

The attachment device can be adjustable, for example to adjust the orientation and positioning of the disinfection apparatus relative to the target disinfection area. For example, the adjustable attachment device can be an adjustable attachment device as described in U.S. Pub. 2015/0297766, filed on Oct. 2, 2013, to Theodore John Cole, entitled PORTABLE LIGHT FASTENING ASSEMBLY, which was previously incorporated by reference in its entirety. Alternatively, the attachment device can be non-adjustable after installation such that the orientation, height, and 7positioning of the disinfection apparatus is fixed at installation relative to the target disinfection area. The attachment device 110 may only attach at one end to the disinfection apparatus 110 and may be configured not to attach at the other end to a support structure, but instead form a self-supporting structure. For example, the attachment device can attach at one end to the disinfection device 100 and be configured as a table stand at the other end for placement near a target disinfection area, such as keyboard 102. In some self-supporting, structure embodiments, although the attachment device 110 may not attach to a separate support structure, such as keyboard 102, the support base of the attachment device 110 may be sized, shaped, and configured to slide under a structure, such as a keyboard. Should the disinfection device be bumped, knocked, or otherwise physically moved in such a way that it would tip backwards, the disinfection device can be prevented from tipping backwards by virtue of the top surface of the support base engaging the bottom surface of the keyboard. Although the structure in the described embodiment refers to a keyboard, essentially any physical structure with sufficient weight that has a crevice, slot, or area in which a portion of the support base of the attachment device can slide under or otherwise inter-fit with, can be operable to prevent tippage.

Various embodiment of UV disinfection devices can be configured for disinfecting both a mobile device and a workstation area, including a keyboard. These embodiments can share a majority of the features of the other embodiments including a housing, a UV-C light source disposed within the housing that is configured to emit UV-C light, a lens configured to direct UV-C light from the UV light source through a major opening in the housing toward a target disinfection area, and a control system configured to control operation of the UV-C light source including activation of the UV-C light source. These embodiments can also include a sensor system that controls operation in a similar manner to the other embodiments. The attachment devices of these embodiments can be joined at one end to the housing. The attachment device can include a support member and a ledge extending therefrom for receiving the mobile device. The other end can terminate in a support base or an attachment mechanism for attaching to a workstation device. Further, the lens can be configured to direct the UV-C light toward a mobile device disinfection zone in proximity to the ledge of the attachment device and toward a workstation disinfection zone in front of the UV disinfection device. Like other embodiments, the disinfection device can include a sensor system and the control system can be configured to receive sensor output from the sensor system and control operation of the UV-C light source according to the sensor output. In these embodiments, the control system can be configured to direct UV-C illumination toward at least one of the mobile device disinfection zone, the workstation disinfection zone, and a combination thereof. The control system may also be configured to control operation of the UV-C light source according to the sensor output to prevent direction of UV-C illumination toward at least one of the mobile device disinfection zone, the workstation disinfection zone, and a combination thereof. The UV-C source includes a plurality of UV LEDs, wherein the lens is configured to direct UV-C light from a portion of the plurality of UV LEDs toward the mobile device disinfection zone and UV-C light from a different portion of the plurality of UV LEDs toward the workstation disinfection zone. The sensor system can be configured to detect human proximity to the mobile device disinfection zone and the control system can respond by deactivating or preventing activation of the portion of UV-C LEDs that direct UV-C light toward the mobile device disinfection zone. Likewise, the same is true of detecting human proximity to the workstation disinfection zone, except that the control system can be configured to deactivate or prevent activation of the portion of UV-C LEDs that direct UV-C light toward the workstation disinfection zone while directing the portion of UV-C LEDs that direct UV-C light toward the mobile disinfection zone to remain active or be activated.

Certain embodiments of the attachment device support structure (e.g. the support base or support arm(s) that joins the support base to the disinfection device) may include a channel that can interface with the back edge of a keyboard or other structure. While interfaced, the channel can help to prevent the disinfection device 100 from tipping over. The channel can be sized and shaped in a variety of different ways. The channel may be specifically configured to interface with a matching protrusion on the keyboard expressly included for anti-tipping purposes or the channel may be configured to interface with an edge or protrusion of the keyboard (or other structure) that is not intended to aid in anti-tipping. For example, the channel may be sized and shaped to accept the rear top edge of a keyboard. The channel can be sized to accommodate a vast majority of typical keyboards, which generally fall within a relatively small range of sizes and shapes. The depth of the channel can be selected to provide suitable anti-tip range.

In other embodiments, the attachment device 110 may include one or more clips, clamps, or other attachment connectors to removably attach to a structure, such as a keyboard. The connectors can be adjustable in order to allow the orientation and height of the disinfection device to be adjusted relative to the structure to which the disinfection device is attached.

The attachment device may include a ledge that supports a personal device. FIGS. 27A-B and 28A-B illustrate one such embodiment. FIGS. 27A-B illustrate a side view and front view, respectively, of an attachment device or support structure 910. The structure includes a base 918, a support 914, and a ledge 916 extending from the support for holding a mobile device. The support 914 can include attachment members 912 that mount to the disinfection device 100, for example via the pair of mounting surfaces 190, 192 and mounting holes 194, 196. In some embodiments, the attachment device 910 can attach to the disinfection device 100 using screws or essentially any other type of fastener.

In the depicted embodiment, the ledge 916 is formed by two tabs that extend away from the support surface 914 to form an "L" shape capable of receiving a mobile device. The ledge can be configured to accept the mobile device in a landscape orientation, portrait orientation, or both. In certain embodiments, the ledge 916 may be formed by a continuous ridge or lip that extends away from the inclined support surface 914 to form an "L" shape instead of multiple tabs. The orientation of the "L" shape can be selected to provide a suitable pitch of a device disposed on the ledge 916. For example, the support 914 can extend from the base 918 at an incline and the ledge can extend approximately perpendicularly away from the inclined support 914. The ledge may have a fixed or variable position relative to the support 914. While disposed on the ledge, the mobile device positioning can be suitable for both 1) a user to view the display of the smart phone while seated at a table or desk upon which the disinfection device 100 is disposed; and 2) the disinfection device 100 to disinfect the touch surface of the smart phone 920. Further, in some embodiments, the ledge may be sized, shaped, and oriented such that a keyboard or other workstation device can slide or otherwise fit under a channel formed between the ledge 916 and the top surface of the base 918. The channel can function as described above as an anti-tipping feature. Further, the disinfection device may be configured to disinfect both the mobile device on the ledge as well as the area in front of the ledge where the keyboard or other workstation device is disposed.

The disinfection device can effectively disinfect the mobile device while disposed on the ledge 916. For example, the disinfection device 100 can activate the UV source 112 to generate a UV illumination pattern on a portion of the exposed touch surface of the mobile device 920. Due to the positioning and pitch of the mobile device on the ledge, the exposed touch surface can include an edge of the mobile device 920 closest to the UV source of the disinfection device 100 as well as the front surface of the mobile device 920 including its display touch screen. The disinfection device may include a reminder system to remind a user to orient their mobile device with a different edge facing the disinfection device 100 to accommodate disinfection of the various surfaces. For example, a visible work light or other signal can provide an indication to the user.

In some embodiments, the support structure 910 may include a UV transmissive coating (or be made from a UV transmissive material) that aids in routing the UV light to more distant surfaces of the mobile device 920 such as the rear and bottom of the device. In some embodiments, the mobile device 920 may include a UV transmissive case that aids in routing the UV light to more distant surfaces of the mobile device 920. For example, various different embodiments of UV transmissive cases are disclosed in WO 2019/241112 to Baarman, filed on Jun. 10, 2019, entitled MOBILE DEVICE DISINFECTION, which is hereby incorporated by reference in its entirety.

The disinfection device can utilize its sensor system to sense presence and absence of the mobile device 920. The presence information can be used by a processor of the disinfection device to alter operation in a variety of different ways. For example, in response to presence of the mobile device on the ledger, the processor can be configured to alter the disinfection protocol of the disinfection apparatus. In one exemplary embodiment the UV source includes a plurality of UV LEDs and disinfection protocol alternation can include activation of a subset of UV LEDs that project an illumination pattern toward the position of the mobile device 920. The subset of UV LEDs can project UV illumination toward the mobile device 920 while a user is present at the workstation without directing UV illumination toward the other workstation devices.

The disinfection device sensor system may sense presence within multiple workstation zones. For example, the sensor system may sense presence at the workstation generally, as well as specific real-time presence in particular sub-zones at the workstation. The sub-zones can correspond to separate selectable UV illumination patterns or sets of patterns. For example, one sub-zone can correspond to the path of UV light from the source to the mobile device 920 and another sub-zone can correspond to the path of UV light from the source to the keyboard or other workstation device positioned for disinfection at the disinfection device 100. In response to presence detection, the UV disinfection device can take a variety of different actions including deactivating or reducing intensity of the UV light source to reduce or prevent human exposure to UV illumination.

The UV illumination can be cast on the mobile device 920 while the mobile device actively displays content viewable by the user allowing the user to simultaneously view and disinfect the mobile device. That is, while the user is present at the workstation, the disinfection device 100 UV source may be deactivated, but the ledge and inclined surface of the support 914 can provide a suitable viewing angle for the display of the mobile device 920. While the user is not present at the workstation, the processor of the disinfection device 100 may be configured to disinfect the mobile device 920 according to essentially any disinfection protocol, such as periodic, low dosage, or presence based disinfection protocols, to name a few examples.

The mobile device 920 may couple to a supplementary device for control without a user having to physically manipulate the mobile device and interrupting disinfection. For example, the mobile device may couple to a workstation personal computer, watch, or other supplementary device that can instruct the mobile device to change operation.

The disinfection device 100 including the attachment device 910 may simultaneously present the mobile device 920 touch surface at an angle to the UV light source for disinfection while also presenting the display surface at an angle viewable by a user sitting at a desk in front of the disinfection device 100. While the user is present at the workstation, the disinfection device 100 UV source may be deactivated, but the ledge and inclined surface of the support 914 can provide a suitable viewing angle for the display of the mobile device 920. While the user is not present at the workstation, the processor of the disinfection device 100 may be configured to disinfect the mobile device 920 according to essentially any disinfection protocol, such as periodic, low dosage, or presence based disinfection protocols, to name a few examples.

The disinfection device 100 including the attachment device 910 may be configured to disinfect both the mobile device 920 and an area in front of the disinfection device 100. The disinfection device 100 can be configured to disinfect both simultaneously, sequentially, or according to some other timing, for example determined by a set of criteria or disinfection protocol. For example, at a workstation table or desk, a keyboard may be placed in the path of the UV illumination pattern cast in front of the disinfection device 100. The UV source, for example a plurality of UV LEDs, may be activated such that they work in concert with a reflector, eyebrow, support, and shade (e.g. size and shape of aperture, louvers, shade orientation, and shade position) to allow the UV light to be cast simultaneously on the mobile device positioned on the ledge as well as a surface or device positioned at the front of the disinfection device, such as a keyboard. The relative sizes and shapes of the disinfection device 100, attachment devices 910, 1010, and mobile device 920 depicted in FIGS. 27A-B, 28A-B, and 29 are representative for illustration purposes. In other embodiments, the relative size of the components may vary drastically from those illustrated. For example, in FIGS. 28A-B the mobile device 920 is depicted in a landscape configuration held by ledges 916 where the device 920 has a longer length than the UV disinfection device 100, in alternative embodiments, the UV disinfection device may have a greater length than the mobile device 920. Further, the UV source, such as the plurality of UV LEDs, can be selected and configured in the housing according to the desired position of the illumination patterns to be cast on the mobile device 920 and the disinfection zone in front of the device 100.

In one embodiment, instead of generating one, single, UV illumination pattern that reaches both the mobile device 920 and the disinfection zone in front of the device 100, the UV source may be configured to generate at least two separate UV illumination patterns, one that corresponds to a ledge UV illumination zone and one that corresponds to a workstation disinfection zone in front of the device 100. The sensing system may include one or more proximity sensors that can distinguish movement, activity, or presence within the distinct zones. For example, the sensing system may include a passive infrared sensor system that can detect motion, action, or proximity within multiple distinct zones. The passive infrared sensor system may include a pair of infrared sensors installed at opposite lateral sides of the disinfection device 100. In an alternative embodiment, one proximity sensor may be specifically configured for proximity detection in a particular zone and another proximity sensor may be specifically configured for proximity detection in another zone. A sensor system capable of detecting presence in discrete sub-zones in combination with a UV disinfection device 100 having a UV source capable of selective activation can enable UV illumination in one sub-zone without enabling UV illumination in another sub-zone. In that way, a mobile device, such as a mobile phone, can be disinfected or cleaned with UV energy while the user is actively using the workstation (e.g. typing on the keyboard of a computer terminal). This can be accomplished because while the user is actively using the workstation, the sensor system is configured to be capable of distinguishing between presence at the workstation generally and presence or proximity to the UV illumination path from the source to the ledge.

Multiple UV illumination patterns can be generated in a variety of different ways. In one embodiment, the UV source includes two or more rows of selectively activatable UV LEDs. The UV LEDs can be positioned and oriented to cast UV light in the two or more desired UV illumination patterns, accounting for any reflectors, an eyebrow, support surfaces, and shade (e.g. size and shape of aperture, louvers, shade orientation, and shade position).

FIGS. 27A-B and FIGS. 28A-B illustrate one embodiment of an attachment device 910 that includes an inclined support 914 extending from a flat base 918 capable of disposition on a generally flat table or desk. The support extension terminates with a pair of vertical arms 912 that are configured for connection to the mounting points of the disinfection device 100, as discussed above. Another configuration of an attachment device 1014 is illustrated in connection with FIG. 29. In the FIG. 29 embodiment, the support 1014 has a steeper incline when extending from the support base 1018. The ledge 1016 extends away from the support 1014 surface to provide a viewing angle of the mobile device 920 for a user sitting at a workstation where the disinfection device 100 is disposed on the workstation surface. In the FIG. 29 embodiment, the mobile device 920 is disposed on the ledge 1016 in the portrait configuration. A portion of the support 1014 provides support for the mobile device 920 to rest against while disposed on the ledge 920. The portion of the support 1014 that provides support for the mobile device 920 back may be a portion of the flat planar surface of the support 1014. Alternatively, the support may include a fixed inset portion upon which the mobile device 920 rests while disposed on the ledge 1016. The fixed inset portion can be joined to or integral with the support 1014. In one alternative embodiment, the inset portion upon which the back of the mobile device 920 rests may be movable relative to support 1014. In such an embodiment, the relative position of the mobile device 920 can be manually adjustable to adjust the viewing angle, viewing distance, or other viewing characteristics for a user sitting at a work station having a workstation surface upon which the disinfection device 100 is disposed. Further, in such an embodiment, the adjustable portion of support 1014 may be movable relative to the UV source. That is, the adjustable portion of support 1014 may be movable to adjust the relative depth, angle, or other position characteristic of the adjustable portion of the support 1014 relative to the unadjustable portion of the support 1014. Because the mobile 920 is or can be disposed on the ledge 1016, movement of the adjustable portion relative to the unadjustable portion of the support 1014 results in adjustment of the mobile device 920. For example, the location of the UV illumination pattern cast by the UV source toward the support 1014 can effectively be adjusted by adjusting the relative position of the adjustable portion relative to the unadjustable portion of the support 1014 because, in such embodiments, the unadjustable portion 1014 shares a fixed position relative to the UV source. Accordingly, the position of the mobile device 920 is or can be adjusted by adjusting the depth or orientation of the support 1014. The movement can be accomplished by essentially any suitable method for relative adjustment of two members. The movable portion may be completely flat or may be shaped to provide selected desirable positions in response to adjustment. Although a portion of the support may move in a single axis generally perpendicular to the other portion of the support, in some embodiments, one portion of the support may tilt relative to the other portion of the support instead of or in addition to the perpendicular movement. Further, the ledge 1016 is illustrated as being joined to the support 1014. In embodiments where the support 1014 includes two portions movable relative to one another, the ledge 1016 may be joined to either portion. The mounting arms 1012 of the FIG. 29 embodiment form an H configuration with arms terminating in bent portions 1013 that provide a horizontal mounting surface for the disinfection device 100. In alternative embodiments, the disinfection device 100 support 1014 and mounting arms 1012 can be configured in a different manner to attach the base 1018 of the disinfection device to the housing of the disinfection device 100.

The FIGS. 10-11, FIGS. 27A-B, 28A-B, and FIG. 29 embodiments depict an assortment of disinfection devices that include an attachment device for supporting the disinfection device housing. As discussed above, one end of the attachment device can removably mount to the UV disinfection device housing and the other end can either terminate in a base for disposal on a surface as a standalone unit or in a separate mounting system for attaching to another device, such as a keyboard, monitor, cabinet, desk, or other workstation device.

Figure 8:
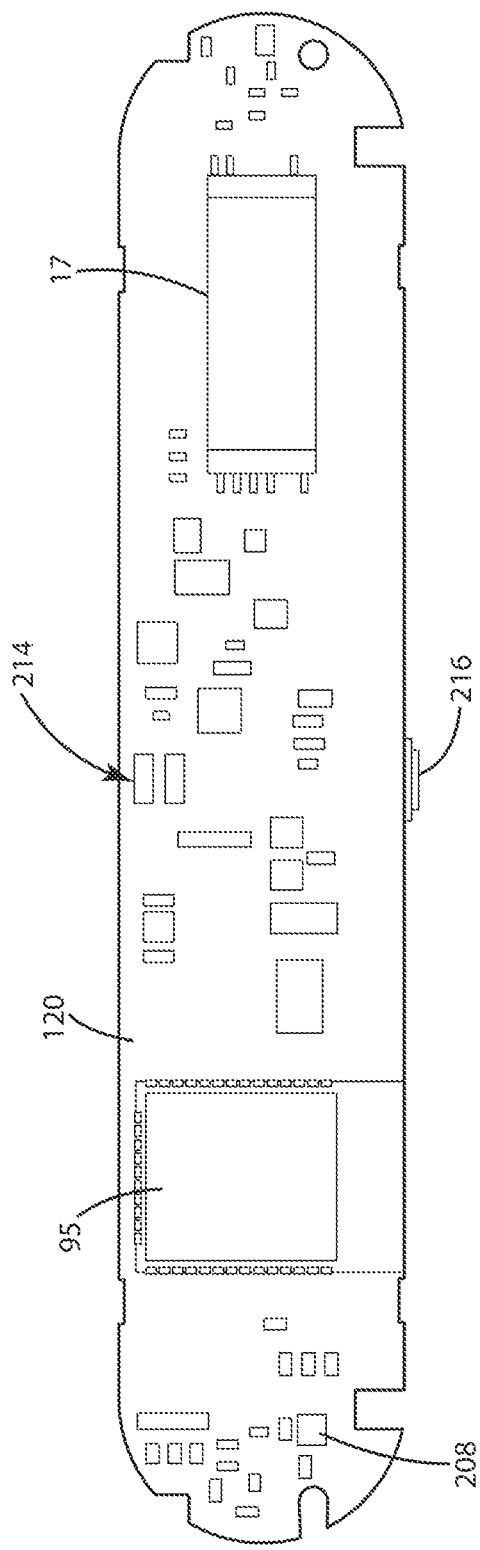
FIG. 8 illustrates a top view of a printed circuit board of the present disclosure.
Figure 9:
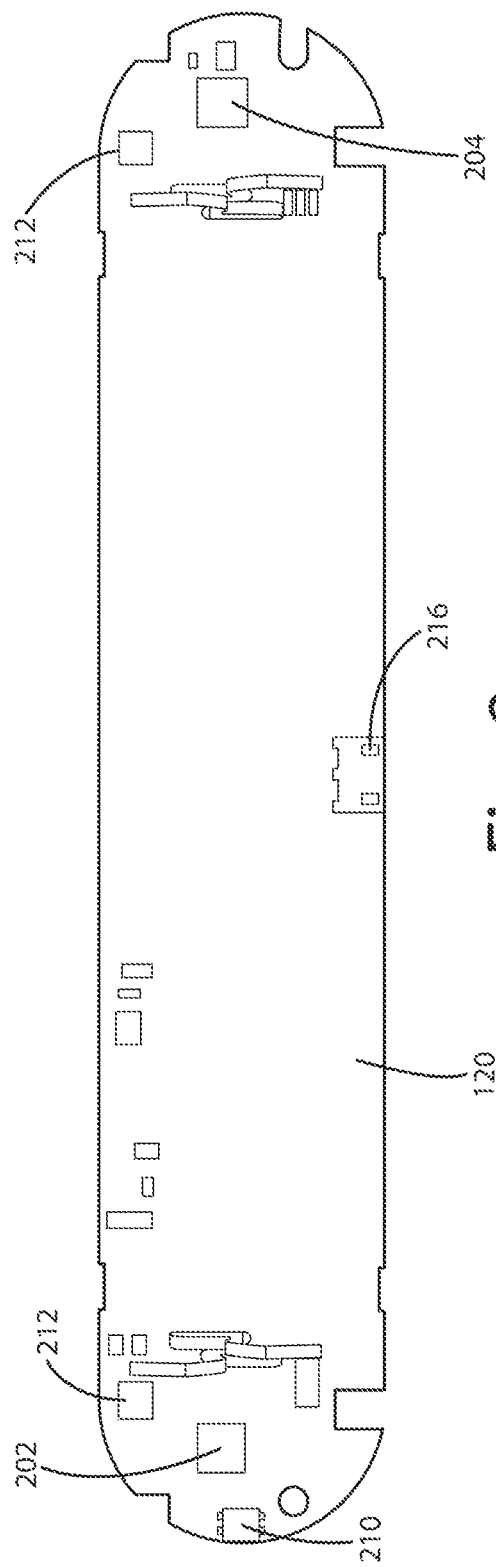
FIG. 9 illustrates a bottom of the printed circuit board.

Exemplary electronics of some embodiments of the disinfection device 100 will now be described. In some embodiments, the disinfection device 100 include a circuit board that includes a number of different electronic components. For example, FIGS. 8-9 depict top and bottom views, respectively, of one embodiment of a circuit board 120 that includes an RGB LED 214 for indicating errors and status to a user, an accelerometer and gyroscope unit 208, a pair of RGB LED work lights 212 that can be configured as indicators and error lights for surface lighting, dual left and right passive infrared motion sensors 202, 204, a pushbutton for mode selection and manual presence indication 210, and a USB port 216 for providing communication and power to the disinfection device.

Figure 7:
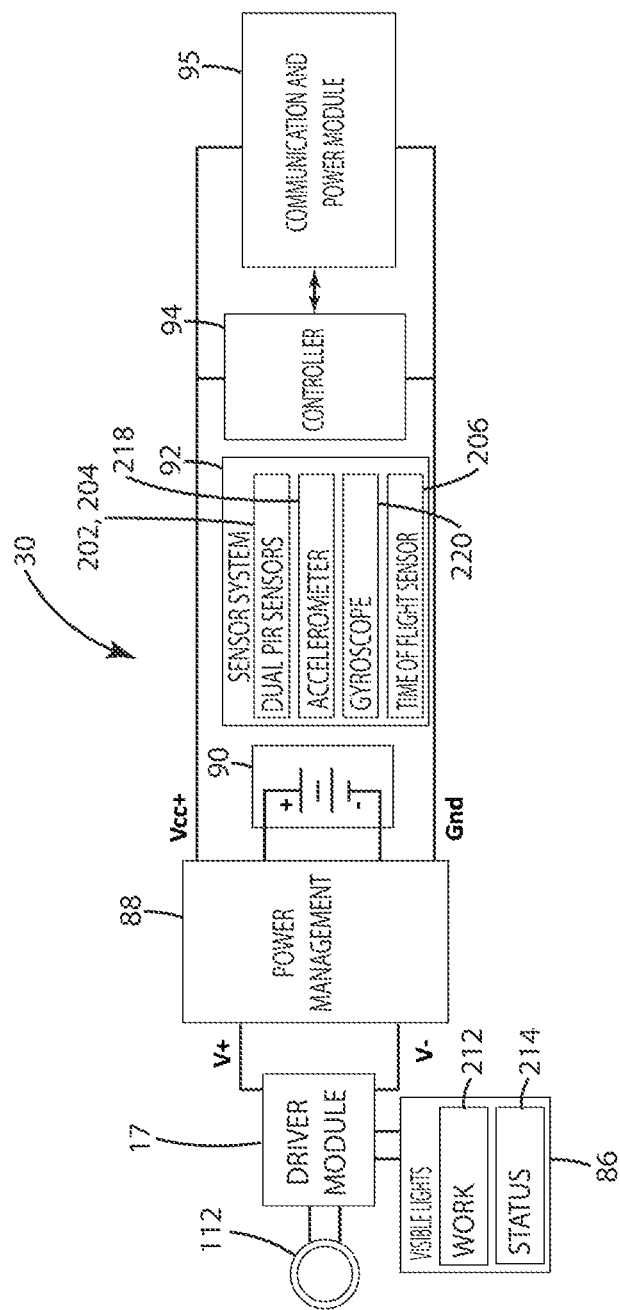
FIG. 7 illustrates a representative block diagram of a control system of the present disclosure.

FIG. 7 illustrates a representative block diagram of some embodiments that shows functional electrical components of the disinfection device 100. In the depicted embodiment, the functional block diagram includes a UV light source 112, a driver module 17 capable of driving UV and visible lights, visible lights 86 including work or task lights 212 and status lighting 214, a power management system 88, a battery 90, a sensor system 92 a control circuit 94, and a communication and power module 95 with a USB port 216.

Exemplary electronics of some embodiments of the disinfection device 100 will now be described. In some embodiments, the disinfection device 100 include a circuit board that includes a number of different electronic components. For example, FIGS. 8-9 depict top and bottom views, respectively, of one embodiment of a circuit board 120 that includes an RGB LED 214 for indicating errors and status to a user, an accelerometer and gyroscope unit 208, a pair of RGB LED work lights 212 that can be configured as indicators and error lights for surface lighting, dual left and right passive infrared motion sensors 202, 204, a pushbutton for mode selection and manual presence indication 210, and a USB port 216 for providing communication and power to the disinfection device.

The exemplary control system 30 will now be described in detail in connection with the representative block diagram of FIG. 7. The control system can include a disinfection device circuit that includes a controller 94 or processor that controls operation of the various components. The disinfection device circuit in the depicted embodiment includes a plurality of components installed on a printed circuit board assembly 120. The exemplary disinfection control system 30 can be configured as an Internet-of Things ("IOT") hub or node within the network, for example as described in WO 2019/190967 to Baarman, filed on Mar. 25, 2019, entitled DISINFECTION BEHAVIOR TRACKING AND RANKING, which is hereby incorporated by reference in its entirety. The UV disinfection control system 30 of this embodiment has a UV-C power source 17 that enables UV-C intensity control and contact time control. For example, the UV-C power source can be a ballast or driver. The UV-C source 112 may be essentially any UV-C source capable of generating UV-C light at the desired intensities. For example, the UV-C source may be a cold cathode lamp, a low pressure mercury lamp or UV-C light emitting diodes. The control system 30 of this embodiment also includes a controller 94 that performs various functions. In this embodiment, the controller 94 is coupled to a sensor system 92 that provides the system 30 with various sensor output, such as dual passive infrared sensors 202, 204, accelerometer 218, gyroscope 220, and time of flight sensor 206. The sensor system 92 can include additional, different or fewer sensors in other embodiments, such as other types of motion sensors, capacitive touch sensors, and temperature sensors. The data collected by the sensors may assist in controlling operation of the system 30 and in collecting data that may be relevant to tracking infection-related events as well as non-infection-related events. The various sensing aspect of this design provides desirable functionality because different events can be used to trigger UV source activation, to interrupt disinfection cycles, and to provide valuable data in making dynamic adjustments to the UV parameters, such as cycle time and source intensity.

The sensor system 92 can include one or more motion sensors, such as the accelerometer 218. In other embodiments, the controller 94 itself can also include an accelerometer that can measure acceleration of the device. An accelerometer can be utilized to track acceleration forces on not only the disinfection device itself, but also on the surrounding structure. For example, touches on the target disinfection area can be detected by an appropriately configured accelerometer with suitable sensitivity. A sensitive 3-axis accelerometer can track touches, movements, and gestures that occur in proximity to the disinfection device in which the accelerometer is installed. Different touch events, movement events, and gesture events can be detected based on the sensor output data patterns of the accelerometer. Some events may only be recognizable by overlaying or combining accelerometer data with other sensor data (available either from the disinfection device itself, networked other disinfection devices, or other data sources). For example, a combination of accelerometer data and time of flight data can enable tracking of certain user habits. Examples of such user habits or events that may be identified can include a user eating food at a desk, a user touching their face, eyes, ears, or nose and immediately interacting with a user interface (mouse, kb, etc.), sneezing including particular type of sneeze such as a sneeze into tissue, clothing, hands, elbow, or nearby equipment, sneeze frequency, time or average time before hand washing after sneeze, user posture, user breaks, number of workstation visitors, chair height adjustments, yawning, keyboard movement, slamming or jostling events, keyboard tray adjustments on a cart or desk, just to name a few. The controller can also include capacitive and voltage sensors, in addition to sensors included elsewhere in the disinfection device sensor systems 92.

The controller 94 of this embodiment can also monitor the current and voltage within preset ranges for proper operation and lamp diagnostics. Sources can be open, shorted, and impedance can change causing different operating voltages that the controller 94 identifies and sends to a remote network component (such as a network server on the cloud) as a service request. In this embodiment, the UV-C power source 17 monitors the current and voltage to the UV source 112 and feeds that information back to the controller 94. The controller 94 may also include volatile and and/or non-volatile storage memory. For example, the controller may include flash memory.

The UV power source 17 of this embodiment is a driver module including a UV driver that includes an amplifier where the amplifier gain can be changed to increase or decrease intensity of the UV source 112. This is essentially changing the lamp voltage within allowed thresholds, and higher thresholds will most likely impact source life. These intensity thresholds may also be contained for each lamp. The hours at each intensity level can be tracked by the controller 94 to accumulate the time at each intensity to enable total end of life calculations. Adjusting and applying the power to the UV lamp at controlled intervals allows the controller 94 to control the UV-C power output. This allows high speed touch iterations or other pattern events to be treated and compensated dynamically. It is not typically ideal to run at the highest intensity as it impacts the source with shorter life. With lower intensity lamp settings, longer duration "on" cycle times (or dose times) may be desired to obtain adequate disinfection. This is a dynamic control that can increases dose momentarily during busy times. A running average of busy times and expected dose changes can be preprogrammed and the algorithm can modify these dynamically based on a pattern of sensor output. The USB interface 216 (or other wired communication interface, such as Ethernet or RS-232) or a BTLE interface (or other wireless communication interface) can be used to allow external electronic devices, such as a smartphone, tablet computer, or other mobile electronic device, to automatically write UV parameters and other relevant values into the control system 30.

In some applications, the UV source is fixed at the specific distance from the target disinfection surface and a UV-C intensity meter is used to assure dose for that interval. This can be used to assure that every device has been calibrated to preset standards. Some lamps are manufactured in glass rather than quartz and will not emit UV-C. This type of quality and output calibration can be used in the field and in the production facility. The OEMs manufacturing the device can assure proper installation configurations over many mounting options and distances with a go-no-go answer for limits of performance. The expected lamp life also changes dynamically as these minimum intensity expectations are set. An aging percentage may be added to these numbers to account for source degradation over the expected source life. Starting calibration values for the control system can account for the span of intensity over the life of the UV lamp. This sets the range of time allowed and may be limited by UV exposure limits, such as eye contact thresholds. For example, the thresholds can be set by OSHA standards for UV-C contact and exposure.

In some applications, it may be desirable to include additional security-related components in the control system 30. For example, a crypto chip can be included to provide each disinfection device 100 with a unique ID, but other mechanisms for identifying each unit may be provided. The security may also be augmented with a token and SSID for security purposes stored in non-volatile memory set up by installation staff through a BTLE, USB, or WiFi interface.

The disinfection control system 30 can have BTLE and mesh capability; the mesh network can be Zigbee or BACNet to meet specific regulatory requirements or hospital specifications. In some embodiments, a cellular module may be used to communicate the data to the cloud as an alternative source of information gathering. The communication and power module 95 may include transceivers and antenna matching circuitry and a cellular module that are coupled to corresponding antennas. The system 30 may also have ports to allow direct wired connections, for example, using USB, Ethernet, and RS-232 protocols.

In some applications, the disinfection control system 30 may have the ability to operate on battery power. The battery version may be provided with a battery 90. The optional battery 90 can be used for portable applications such as remote inventory areas or procedure augmentation and support. Crash carts and infrequently used tools are reasonable applications for these types of systems. In the current embodiment, the battery 90 can be rechargeable via the USB port 216 that provides power and communication via the communication and power module 95. The battery 90 can also provide power to the components while external power is unavailable. In alternative embodiments, a battery may not be included in the disinfection device. Further, the system 30 may include additional power sources, such as a wireless power receiver system.

In typical applications, it is beneficial for the control to be versatile to allow embedding into the various applications mentioned in the disclosure. Because disinfection effectiveness is a product of intensity and time at a given distance, the calibrated numbers set the starting point or dose at a given distance. This control system 30 may, however, be dynamic to allow many different distance and mounting options on various devices like vitals monitors, glove boxes, IV pumps, medical carts, keyboards, above or below computer monitors, cabinets, etc.

The control system 30 may also have USB and Power over Ethernet ("POE") circuitry included in the communication and power module 95 to enable simple usage without additional power cord requirements for this equipment. The power management circuit 88 of this embodiment is designed as an energy harvesting power supply as to allow inputs from power generating sources and various voltages enabling flexible power adaptation. The circuit is designed to allow AC power to pass through so that the host piece of equipment is undisturbed. This can be helpful in many applications as these environments have stringent electrical drainage requirements for safety. For example, when the UV disinfection system 30 is integrated into another electronic device, the power management circuit 88 allows the UV disinfection system 30 to draw power from the power supply for the host electronic device. This allows only one outlet to be used and minimizes the confusion when plugging in the device(s). The internal power management circuit 88 may be designed to use wireless, USB, DC, and battery sources. The harvesting circuit enables the disinfection device to be powered from the current in the power cord of the host device. The battery can be charged if even a small current can be harvested charging the battery over time enabling a good use profile. The UV disinfection control system 30 can be implemented without a harvesting circuit and may instead be powered separately from the host device. For example, the UV disinfection control system 30 may use a dedicated source of power when it is not integrated into a host device, as shown in the illustrated embodiments of FIGS. 1-14 that are powered via USB port 216.

The control system 30 can include feedback outputs visible lighting 86, such as work lights 212 and the status light 214. These lights can be RGB LEDs allowing software configurable surface and indication lighting. This lighting option allows light patterns and colors to be configurable. This visible lighting may be used in connection with the disinfection user interface for feedback or may be used to provide supplemental lighting, such as a work light, with all configurable options. The visible lighting 88 can be driven by a visible light driver or other circuit that is part of the driver module 17. The driver module 17 can include separate drivers for the UV source 112 and the visible light sources 86. The drivers in the driver module 17 can control the amount of power delivered to the different light sources. In particular, the drivers can regulate the current to the UV source and the visible light sources. Further, where appropriate, the driver circuitry can provide sufficient voltage to start the lamps. In embodiments with a UV tube light, such as UV source 112, the driver can be a ballast that ensures the amount of current provided to the lamp meets its specification.

Controller 94 can configure the UV lamp driver or UV power source 17 to provide a particular intensity that can deliver a UV dose under the ISO standard for a predetermined period of time. The controller 94 can monitor the UV dosage levels, for example, over an eight hour period or other time period, using a real time clock, for example onboard the controller. Data can be accumulated in a non-volatile accumulator and reported over time via the communication module 95.

Different embodiments of the control system 30 and sensor system 92 will now be described in more detail. The sensor system 92 can include a plurality of different sensors that vary by embodiment. The sensors can be in communication with a control circuit 94 that operates the UV light source 112 via the driver circuit 17. The sensors can be configured to provide sensor output for detecting events proximate to the disinfection device 100. For example, the sensors can provide output for detecting events related to human presence, lack of human presence, physical cleaning, mouse interaction, keyboard interaction, walking by, occupancy, surface touches, and other events discernible from sensor output patterns of one or a combination of more than one sensor. Further, the sensor system and control system can cooperate to detect these and other events in advantageous ways, for example in ways that do not rely on configuring a sensor in a conventional manner, sensor output data from a particular isolated sensor, use of sensor output data in a conventional manner, or any combination thereof. Instead, the sensor system 92 and controller 94 of some embodiments can cooperate to sense interesting events from a different sensor configuration, layering sensor output data from a combination of sensors to provide redundancy, validation, or interesting insights, use sensor output data in an interesting manner, or any combination thereof.

In some embodiments, the sensor module 92 includes dual passive infrared sensors 202, 204, an accelerometer 218 and gyroscope 220 (combined as unit 208 on circuit board 120), and a time of flight sensor 205. The various sensors are referred to as being part of sensor system 92 in the representative block diagram of FIG. 7 not because of their relative position, but to simplify discussion of functional aspects of the collection of sensors throughout the application. That is, throughout the application, some of the aspects of the disclosure relate to sensor output data patterns of one or a combination of sensors, it should be understood that any of the sensors included in the sensor system 92 can be involved in such aspects.

As discussed above, the disinfection system 100 can include a processor 94 in communication between the UV light source 112 and the sensor system 92. The processor 94 can be configured to activate the UV light source 112 according to a control scheme based on sensor output from the sensor system 92. For example, the processor 94 can activate and deactivate the UV light source 112 in response to counters, flags, triggers, or other disinfection logic constructs maintained in memory via sensor output monitoring, as described in greater detail herein.

Figure 15:
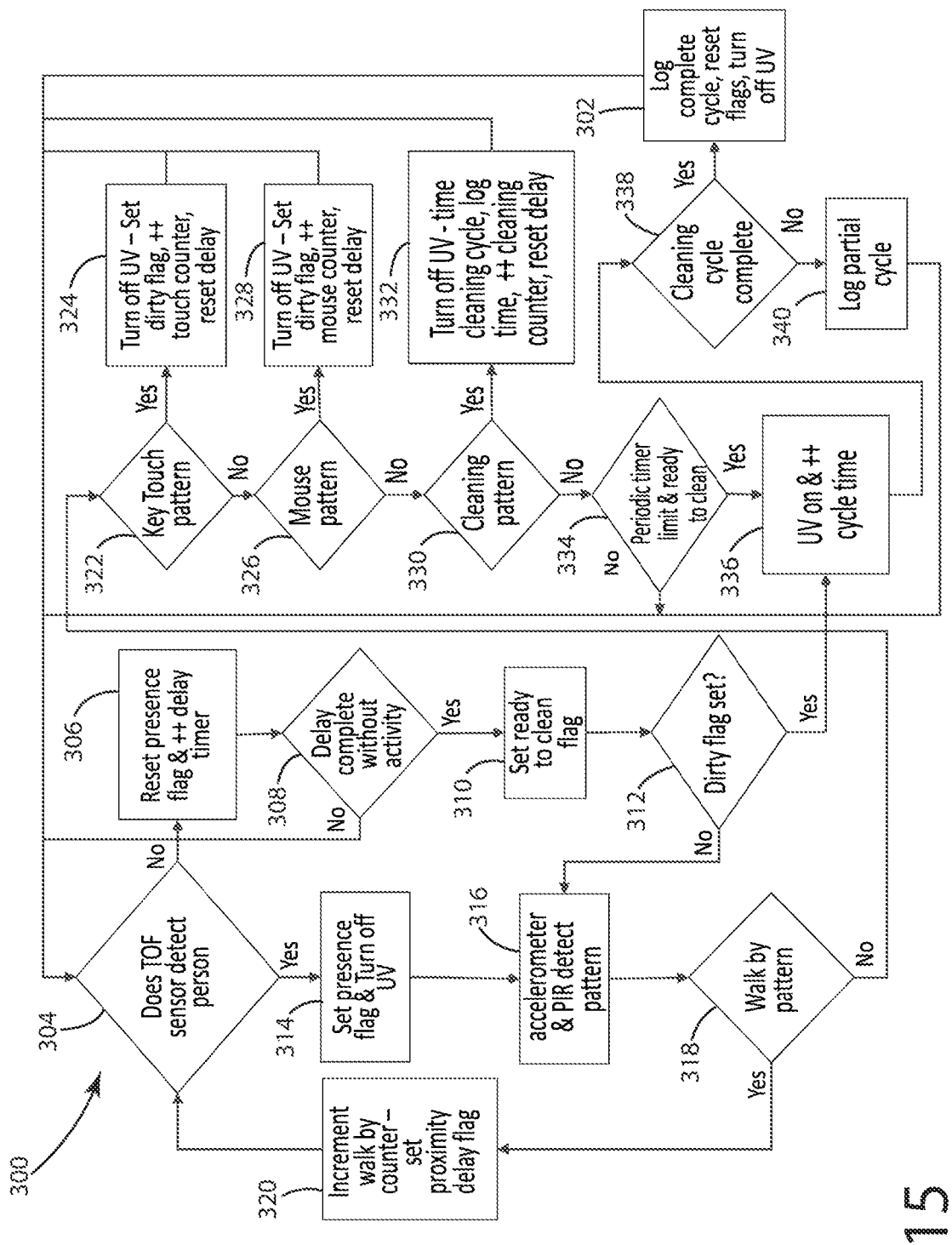
FIG. 15 illustrates a representative flow chart of a disinfection scheme in accordance with one embodiment.

One exemplary method of disinfecting a target disinfection area 300 is illustrated in connection with the flowchart of FIG. 15. The method includes steps for flagging a target disinfection area as ready for disinfection and steps for flagging a target disinfection area as dirty. In response to those two flags, the method initiates a UV disinfection cycle. The method can also include initiating a periodic disinfection cycle in response to a periodic time limit being reached and then the ready for disinfection flag being set. For ease of explanation, the explanation will begin with logging a complete disinfection cycle, resetting all flags, and deactivating the UV source 302. From this point, the control circuit 94 can be configured to wait for a predetermined period of time in accordance with a periodic disinfection schedule or can proceed directly to flagging another disinfection cycle.

When ready, the method proceeds to detecting, with a time of flight sensor, whether there is human presence in the vicinity of the disinfection device 304. A time of flight sensor, sometimes referred to as a time of flight camera, is a sensor that measures the time taken by an object, particle, or wave to travel a distance. There are a variety of different types of time of flight sensors, some of which utilize light detection and ranging ("LIDAR") to measure the depth of various points in an image by illuminating the target area with infrared light. Data captured with time of flight sensors can be particularly useful for detecting human presence—even when there is low or no motion. Time of flight sensor data can also be useful in connection with simultaneous localization and mapping ("SLAM") technology. For example, where a plurality of disinfection devices are installed across a hospital environment, the time of flight data can be aggregated and utilized to provide additional information, such as occupancy, human movement, and mapping data that can be useful in connection with disinfection spread analysis or other non-disinfection based analysis. In the current disclosure, the time of flight sensor is a VL53L3CX time-of-flight ranging sensor with multi target detection available from STMicroelecronics. The TOF sensor is able to detect different objects within the field of view with depth understanding, which when combined with other sensor output, such as the dual PIR sensor output, accelerometer sensor output, accelerometer sensor output, other sensor output, or any combination thereof, can provide event detection for a wide range of different events. Alternatives or additional sensors to a time of flight sensor can be utilized in other embodiments such as ultrasonic, capacitive, inductive, or other types of active infrared sensors.

With reference to FIGS. 18A-B, time of flight sensors work by transmitting an infrared light 402 that bounces off any object 406 and returns to the sensor 404. Based on the time difference between the emission of the light and its return to the sensor after being reflected, the sensor is able to measure the distance between the object 406 and the sensor 100. Two common ways time of flight sensors operate are timed pulses and phase shift of an amplitude modulated wave. Time of flight sensors can compose a three dimensional image of the target area quickly because its measurements are based on the speed of light. Some especially efficient and cost effective time of flight sensors can provide a single-point short-range distance measurement in real-time, which is particularly suitable for certain embodiments of the present disclosure. That is, the time of flight sensor 206 can be configured to accurately, in real-time, detect human presence and perhaps more notably, lack of human presence in a cost effective and efficient manner. Specifically, because the disinfection device 100 is placed at a relatively fixed position and orientation at installation, the time of flight sensor can be calibrated to detect presence and lack of presence of a human in proximity sensor redundancy can further improve this presence and lack of presence detection for humans by providing validation.

Additional confidence and speed in making determinations about human presence and lack of human presence can enable lowering of delay time—the time between when a human leaves the target disinfection area before disinfection begins. For example, by using multiple sensors to detect lack of human presence, speed can be increased because as soon as lack of presence is detected in response to one sensor, the delay timer can be initiated. Then, before the delay time is complete, the other sensor can confirm the lack of presence. Utilizing this method, the lack of presence is independently verified before the UV-C source is activated. Accordingly, in some embodiments, the delay time can be lowered to an amount of time sufficient for each sensor to complete its lack of presence detection. If lack of presence cannot be confirmed by the second sensor before the delay time completes, the UV disinfection cycle can be aborted.

For example, where the disinfection device 100 is mounted at the top edge of the middle of a keyboard, such as shown in FIGS. 10-11, the time of flight sensor 206 can be calibrated to detect a change in distance that occurs by virtue of human presence sitting in front of the keyboard. Further, the time of flight sensor can be configured to immediately detect that a patient has left the vicinity, which for disinfection models can lead to an increase in valuable disinfection time. That is, for disinfection devices 100 installed on heavily used equipment such as work stations or mobile carts, full disinfection cycles can be difficult to complete in the time when a user stops using the equipment to the time when that or another user comes back to use the equipment again. The disinfection device 100 is typically configured to utilize a delay time before activating the UV disinfection cycle in order to increase the chance that the user has actually stopped using the equipment before the disinfection begins. The delay time can be initiated once the target disinfection area is flagged as ready for cleaning, then if one of the sensors indicates the user is still present, the delay time can be reset. With conventional motion sensors or other types of sensors, determining a lack of human presence can sometimes be slower than preferred. This can lead to fewer complete UV disinfection cycles and the various issues that can arise from that. Accordingly, the use of a time of flight sensor to detect a lack of human presence can make the disinfection process, and specifically the initiation of the delay timer, more efficient.

Referring back to FIG. 15 and the exemplary method of flagging a target disinfection area ready for disinfection and monitoring certain events, if the time of flight sensor determines, in real-time, that there is no human present, then the method proceeds to reset the presence flag and activate the delay timer 306. If the delay timer is interrupted 308 by one of the sensors (or combination of sensors) detecting human presence during the delay time, then the method halts the delay timer and utilizes the time of flight sensor to confirm human presence. Otherwise, if the delay timer completes without the control system receiving sensor output data indicative of human activity or presence, then the system 30 sets a ready to clean flag 310 indicative of the system not being prohibited by human presence. If the dirty flag is also set 312, then the method initiates a disinfection cycle 336. If there is no dirty flag set 312, then the system can enter a state of checking for sensor patterns indicative of the target disinfection area being dirty 316.

If the time of flight sensor does detect human presence, then a presence flag is set and the UV light is turned off if it is on 314. The method then checks for sensor output patterns 316. For example, the current embodiment of the method checks for a walk by pattern 318 from the dual PIR sensor output, and upon seeing one increments a walk by counter and sets a proximity or presence delay flag 320.

A walk by event is one example of an event that can be identified from the sensor system output. The dual PIR sensor output can include data indicative of hand movement when typing or wiping down a keyboard as depicted in FIGS. 20A-B and FIGS. 21A-B. A walk by event is another type of event that can be discerned from dual PIR output data. The percentage of IR intensity (y-axis) and time (x-axis) of a walk by event allows distinguishing a user walking by the disinfection device from the left or from the right. Further, the intensity and timing information can give an indication as to the amount of traffic in the area and can also be utilized to drive selection of a particular control scheme for the disinfection device as well as to adjustment of certain parameters such as increasing or decreasing the delay time. Further, a walk by counter can be incremented whenever such an event is encountered and a proximity delay flag can be set. Such a flag can essentially be utilized as a presence flag, or alternatively can be used as a precursor to a presence flag to conduct other sensor measurements more often due to the increased likelihood of presence. Such a proximity flag can even act as a wake-up signal or as a trigger for boosting power to an active IR or other signal to increase resolution or speed of response.

From there, the time of flight sensor is checked for human presence 304. A proximity delay flag can be used to delay the presence detection from the time of flight sensor momentarily to ensure the human presence, due to the walk by event, does not trigger the time of flight sensor. Alternatively, if a presence delay flag is set, the time of flight sensor may be configured such that walk by presence is insufficient to trigger the time of flight presence detection.

If no walk by pattern is detected 318, the system can identify whether a key touch pattern is recognized 322. A key touch can be identified from a variety of different sensors. For example, to the extent the disinfection device 100 is in communication with a keyboard or other input device within the target disinfection area, it may be possible to intercept or otherwise receive an indication of a keypress from the input device or another device. However, often times direct receiving or intercepting such a direct indication of a keypress is impractical or not preferred, for example due to potential security or privacy concerns. In one embodiment, the sensor system 92 includes a sound sensor or microphone capable of detecting key presses. For example, a high sensitivity sound microphone sensor can be configured and calibrated to detect the sound of keys being pressed on a keyboard (or another type of sound indicative of human presence). The microphone can be configured to determine human presence after sensing a pattern of multiple sounds within a window of time that are indicative of a series of key presses consistent with a human typing at a keyboard (or again consistent with another activity indicative of human presence).

FIG. 19 illustrates a graph of time on the x-axis and amplitude in decibels on the y-axis. The depicted graph shows a moving window of about 9 seconds along the x-axis where each of the spikes in amplitude represents the sound level created by a keyboard character being pressed. The controller can be configured to detect human presence in response to a particular pattern of keypresses within a particular unit of time. For example, the average person types between 190 and 200 characters per minute. Accordingly, a pattern indicative of a range of characters per minute within a range corresponding to realistic character per minute typing can be utilized as an indicator of human presence, such as about 100-500 characters per minute. Monitoring the microphone for a particular pattern of keypresses provides a more accurate indicator of human presence than monitoring for a single keypress, which might be triggered by activity unrelated to the keyboard. The disinfection apparatus (or another system that collects data from multiple disinfection devices) can flag errant events. For example, if the sensor indicates 900+ characters per minute, the event can be flagged for further review, potentially being considered with other sensor data based on time and date stamp information collected from the disinfection device, or from other sensors, not associated with the disinfection device.

Figure 20A:
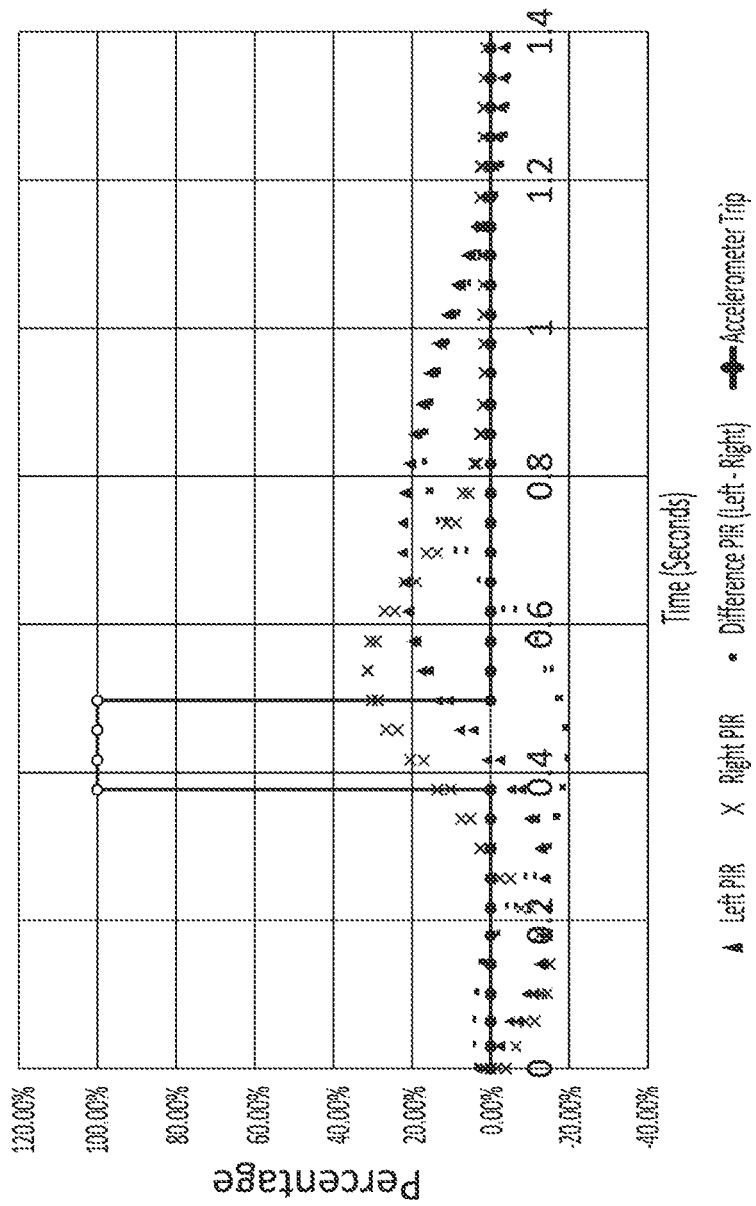
FIGS. 20A-B illustrate exemplary graphs of acceleration and dual PIR sensor output data including patterns indicative of keyboard key presses.
Figure 20B:
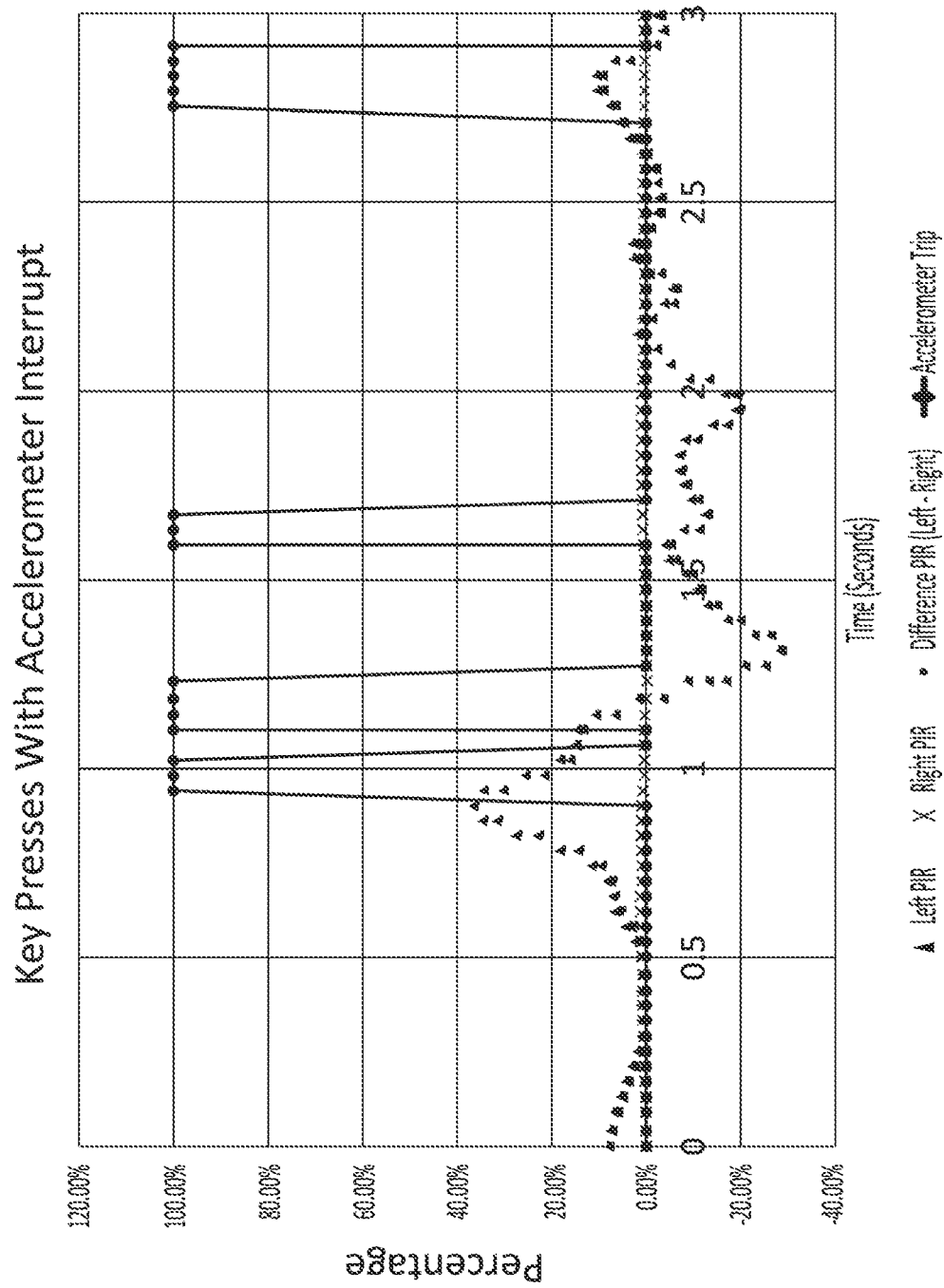

A key touch pattern can be identified from sensor output from the accelerometer 218. FIGS. 20A and 20B illustrate graphs that include accelerometer output data in connection with key press events. Both graphs show time in seconds on the x-axis and percentage on the y-axis. Further, both graphs also show dual passive infrared values during the same time period overlaid on top of the accelerometer output.

The sensor system 92 of the current embodiment includes an accelerometer and gyroscope combined on a single chip, specifically the LSM6DS3 chip, which is a system-in-package available from STMicroelectronics featuring a 3D digital accelerometer and a 3D digital gyroscope performing at 1.25 mA in high performance mode and enabling always-on low-power features for an optical motion experience. Alternative embodiments can include a different accelerometer and gyroscope.

FIG. 20A illustrates a graph showing the accelerometer during movement of a user's right hand into the target disinfection area to press a single key. This graph shows a simple example of the type of sensor output that the disinfection device can collect. The accelerometer can provide linear acceleration measurements in 3 axes. The measurements can be output and provided to the control system 30 in g-force units. The disinfection device 100 includes the accelerometer and the disinfection device 100 is disposed at or near the target disinfection area. By virtue of this arrangement, touches at or near the target disinfection area result in acceleration changes measurable by the accelerometer. For example, the g-forces resultant from touching the area within the vicinity of the disinfection device, even indirectly, can be sensed by the accelerometer. In the current embodiment, the control system is configured to identify accelerometer forces above a predetermined threshold as touches. Further, the shape, duration, and direction of such acceleration g-force measurements can allow differentiation between key presses and other touches in the vicinity of the disinfection device. The accelerometer can be configured such that it is sufficiently sensitive to register g-forces even where touches at the target disinfection area or devices within the target disinfection area can be identified despite limited and indirect coupling between the disinfection device accelerometer and the surface and devices in the target disinfection area. For example, a tap on the target disinfection surface can register on the accelerometer. The graph in FIG. 20A shows the Y-axis in terms of percentage and in this embodiment the control circuit is configured to register any 45+g-force as a touch (in other embodiments it can be a different amount), shown here as a 100% value. In alternative embodiments a different g-force threshold can be set or a graduated force threshold may be utilized to distinguish between the force of touch. Further, the g-force threshold can be for a measurement in a particular linear axis of the accelerometer or in terms of acceleration in the direction of the key press, which due to the orientation of the accelerometer due to the orientation of the disinfection device, may involve multiple accelerometer axes g-force measurements.

In addition to the accelerometer sensor output depicted on the graph of FIG. 20A, the graph also includes sensor output data of the left passive infrared sensor and the right passive infrared sensor, and the difference between them. The left and right passive infrared sensors can absorb infrared rays emitted from the human body to detect the natural infrared signature produced by humans. Further the dual passive infrared sensors provide a disinfection apparatus and method for detecting lateral human movement. The dual PIR sensors are bi-optic, which provides a range of benefits over a single PIR sensor. The infrared sensors of the current embodiment are the Pyroelectric Infrared Sensors available from KEMET. These infrared sensors do not include a lens. High density polyethylene covers 203 are configured to cover the PIR sensor, which block environmental wind that can negatively impact the PIR sensor readings in the disinfection device. The dual PIR sensor data is useful in its own right, for example to detect hand movement of human in proximity of the disinfection device. By positioning the two PIR sensors at the lateral sides of the opening 108 and taking the difference between the two sensor outputs, meaningful data about the position of the human activity in the target disinfection area can be discerned. For example, as shown in FIG. 20A, the right passive infrared detector values start to rise just before the accelerometer trips. Taken alone, it may not be possible to distinguish whether the accelerometer activity is a key press or a tap on the table, however, when the accelerometer and dual PIR data is used in tandem, the event prediction accuracy increases greatly. Further, the particular area of the target disinfection area that is undergoing more heavy use, which can be useful in making decisions about any adjustments to the disinfection devices (for example, if the orientation, height, or lateral positioning of the device should be adjusted). Further, some embodiments of the disinfection device can include dynamic and variable control. For example, where a UV LED array is utilized instead of a UV tube bulb, the UV LED array can control intensity across the array at different levels, and can adapt the intensity of UV light depending on the particular use case sensed by the sensors. One simple example is a workstation where the mouse is used on the right side versus the left. That can lead to making configuration changes to better suit effective disinfection.

FIG. 20B shows another graph that includes additional data for an accelerometer and dual PIR sensors. Again, the reach in motion can be easily seen using the dual PIR sensor data followed by several key presses and hand movement. Further, this particular data output illustrates that the activity is on the left side of the target disinfection area. Accordingly, the user is reaching in to the keyboard with one hand on the left side of the keyboard and operating the keyboard with that one hand because there is no right PIR detection at all. Were similar data to be collected at length, it may indicate a problem with the installation where the disinfection device has an improper orientation or position, or a faulty sensor. The validation and redundancy provided by having multiple PIR sensors and an accelerometer allows for the sensor output to be analyzed and either errant configurations to be identified or particular use patterns to be identified.

Returning to FIG. 15, if the controller identifies a key touch pattern 322 (for example by detecting an acceleration pattern or sound pattern, as discussed above), then the dirty flag can be set indicating human activity in the target disinfection area that warrants initiation of a UV cycle 324. Further, the method can specifically identify that a touch event triggered the setting of the dirty flag, for example by incrementing a touch counter or other tracker. From there, the method can return to monitor for a lack of human presence 304.

The method can also include identifying whether a particular mouse pattern is recognized 326 in the sensor output. A mouse pattern may include movement of the mouse, clicking of a mouse button, or a combination of both. Mouse patterns can be identified from a variety of different sensor output. For example, to the extent the disinfection device 100 is in communication with a mouse or other input device within the target disinfection area (for example via wireless or wired connection—directly or indirectly), it may be possible to intercept or otherwise receive an indication of mouse activity from the mouse itself or another device. However, as discussed in connection with keyboards, often times directly receiving or intercepting mouse activity is impractical or not preferred, for example due to potential security or privacy concerns.

In one embodiment of the present disclosure, the sensor system 92 includes a sound sensor or microphone capable of detecting mouse clicks. For example, a high sensitivity sound microphone sensor can be configured and calibrated to detect the sound of a mouse button being pressed. The microphone can be configured to determine human presence after sensing a pattern of multiple sounds within a window of time that are indicative of a series of mouse clicks consistent with human mouse activity. Monitoring the microphone for a particular pattern of mouse clicks (e.g., a certain number of clicks per unit of time) can provide a more accurate indicator of human presence than monitoring for a single mouse press, which might be triggered by activity unrelated to the mouse. Alternatively, mouse activity may be monitored and understood according to patterns of other sensors, such as the accelerometer or dual passive infrared sensors. For example, the dual passive infrared sensors can detect a pattern of mouse movement as a user's hand moves the mouse backward and forward. In response to detecting the particular mouse pattern the system is configured to identify, the disinfection apparatus can be configured to turn off the UV source (if active), set a dirty flag, increase a mouse counter, and reset the delay timer 328.

It is worth noting that the mouse and keyboard patterns are merely two examples of the types of events that have recognizable patterns in the sensor output data that are distinguishable. Other touch events can be identified from different patterns. Further, there are numerous sub-events that can be identified from certain patterns, e.g., certain types and quantities of keyboard touching or mouse usage. The touch events can be categorized and recognized even more accurately when utilizing multiple sensor data sources in concert. For example, the dual PIR sensor data can be analyzed in concert with acceleration or sound data to increase pattern recognition as a particular event. As a simple example, keyboard use and mouse use are typically performed asynchronously as users switch between using a mouse to navigate a computer interface and a keyboard to input keystrokes. Accordingly, the mouse and keyboard touch detection can work in conjunction (as well as in conjunction with other touch detection schemes) to provide a more accurate account of the status of the touch surface.

While detailed event recognition may not be necessary for human presence detection and turning off an active UV source, it can provide additional redundancy as a backup to any human presence detection, such as a time of flight sensor. Another way the pattern recognition can be utilized is in dynamic control of delay time—a particular keyboard may be used in a particular manner that allows the system to know when use will continue or when use is over and a delay timer should be started. Further, where patterns are predictable and lower delay times are desired, for example in situations where a disinfection device has difficulty completing a sufficient number of disinfection cycles, the delay times may be lowered dynamically based on the detected patterns. As an example, a particular sequence of active keyboard use interspersed with a particular sequence of mouse use can be utilized to recognize when a particular event is being performed, and in particular when that event is concluded and the user is vacated such that the system can institute a lower delay time confident that the target disinfection area is likely to lack human presence for a particular period of time.

In addition, the disinfection status flags can be set more judiciously based on the various events detected by the different touch patterns. For example, the dirty flag may not be a binary value, but instead be indicative of a touch level that can be utilized to change operation of the UV disinfection device—such as by increasing or decreasing intensity levels, and increasing or decreasing delay times. Even where the dirty flag is a binary value, the threshold for setting the dirty flag may be based on a particular amount of touch activity and other data available to administrators. For example, the amount of touch necessary to trigger a dirty flag may be changed depending on external factors, such as a risk score, traffic level near that disinfection device, or other factors associated with that particular location, room, or building. Such change can be implemented automatically or manually, for example via the communication system, at a periodic maintenance session where one or a group of disinfection devices can be adjusted based on collected data and other factors. Even in a system where any detected touch event sets a dirty flag, a touch counter identifying the action that set the dirty flag can be incremented, such that over a period of time, data can be collected about the number and types of events that triggered disinfection cycles. That information can be utilized to make adjustments, such as trigger values, to disinfection procedures, either related to the disinfection device or to general disinfection procedures. The information can also be utilized for other purposes such as byproduct data for influencing non-disinfection related systems and decisions.

Even more types of touches and other events can also be detected based on the sensor output patterns. For example, the dual PIR sensor output data can include patterns indicative of medications being prepared on a surface within a target disinfection area or of a user changing the positioning of a user input device, such as a keyboard or mouse. For example, a user may use the mouse or keyboard on a different surface, which can be identified by a correlated pattern of data, such as dual PIR pattern data, sound data, or acceleration data. These pattern recognition techniques can be useful for setting or adjusting various triggers within a disinfection system, for identifying errant occurrences that can be flagged for investigation, or as byproduct data useful for non-disinfection related systems.

Figure 21A:
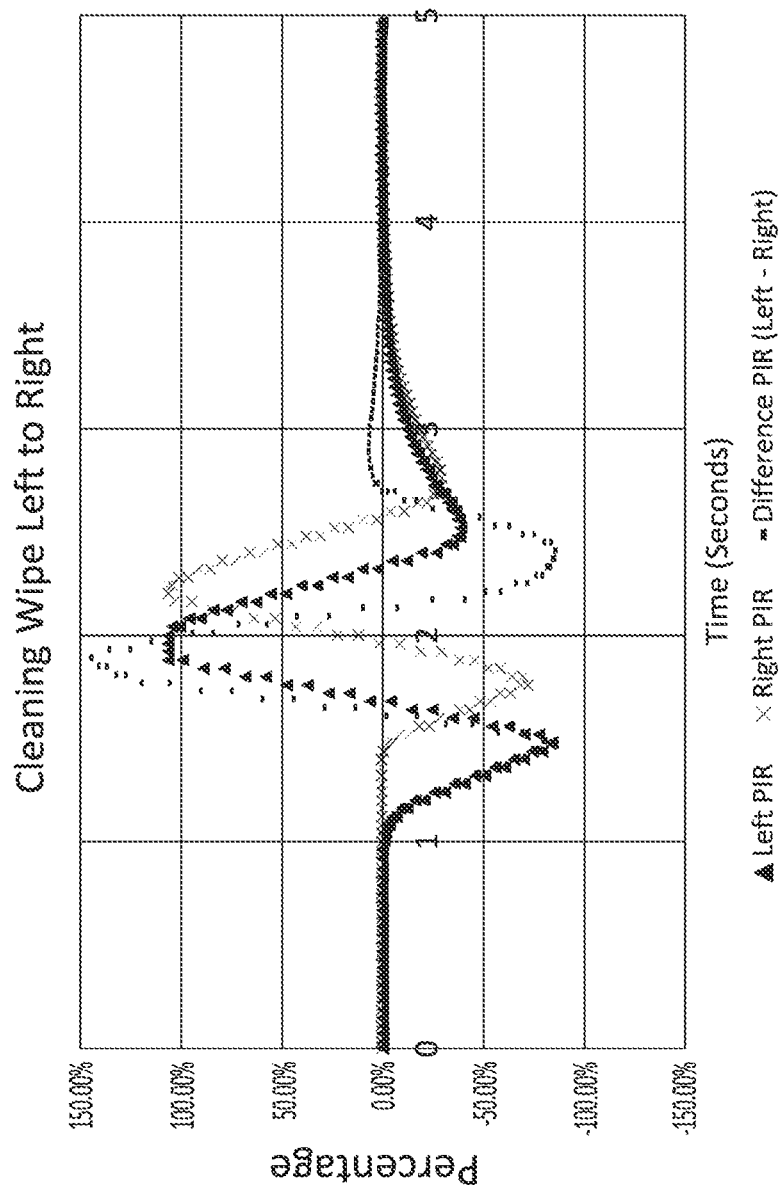
FIG. 21A illustrates an exemplary graphs of dual PIR sensor output data including a pattern indicative of a cleaning wipe motion from left to right of a human.
Figure 21B:
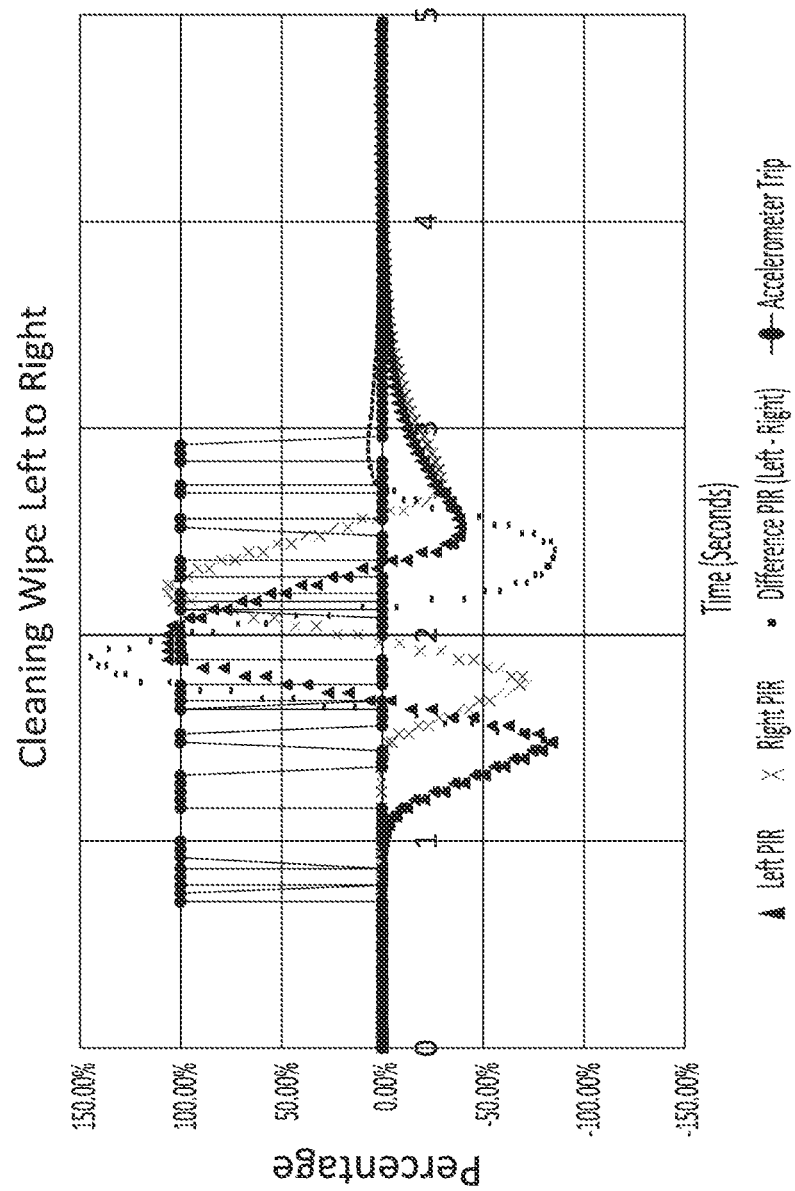
FIG. 21B illustrates an exemplary graph of acceleration output data and dual PIR sensor output data including a pattern indicative of a cleaning wipe motion from left to right of a human.

The method 300 can also include detecting a cleaning pattern in sensor output data 330. For example, as shown in FIGS. 21A-B. FIG. 21A shows dual PIR sensor data indicative of cleaning a keyboard by wiping from the left to the right. The dual PIR sensor data is helpful in providing information regarding the lateral position of human activity. As the user starts from the left, the left PIR and difference PIR spike low, then the right PIR sensor follows as the infrared energy from the human's hand takes longer to reach the right sensor from the left side of the disinfection area. Then as the user wipes the keyboard moving their hand to the other side, the PIR sensor data flips showing a higher percentage of intensity on the right side. The sensor output data can be useful in not only identifying particular events, but also in measuring the quality of those events. In this case, the amount of time (about 3 seconds) spent wiping is apparent. Further, many sanitizers or disinfectants that are used during standard and terminal cleaning at hospitals require a specific dwell time where the disinfectant must be in contact with the surface and remain wet in order to achieve the desired effect. If this disinfectant was wiped again within a few seconds, it may trigger an opportunity for training or to identify a potential flaw in the cleaning procedures.

Furthermore, the lack of seeing a wiping event such as that depicted in FIG. 21A may similarly act as a trigger. It should be understood that a wiping event and the associated information is just one type of event that can be tracked and identified. FIG. 21B shows the same type of left to right cleaning action, but the accelerometer data is included. This type of data can be useful as well because it can indicate as to whether the keyboard is being wiped or not—if a surface were being wiped the accelerometer would not trigger successively as depicted. By combining this data, the accuracy and the underlying quality is improved. Additional sensor data could be layered on top of the dual PIR and accelerometer data to provide additional insights. For example, time of flight sensor data could be utilized to track cleaning cycle times more accurately.

Returning to FIG. 15, in response to detecting a cleaning pattern 330, the UV light can be deactivated if on, the cleaning time can be tracked and logged, a counter can be incremented, and the delay timer can be reset 332.

If none of the patterns are detected, a check is made to see if the periodic time limit is up and the device is ready to clean. If so, the disinfection device 100 initiates a UV disinfection cycle 336, which includes turning the UV lamp on and incrementing a cycle time counter, which tracks the amounts the UV exposure. The process can include monitoring whether the cleaning cycle completes or not 338. If the cycle is not able to complete in full, then the details of the partial cycle can be logged 340 and the process can return to presence detection 304 without clearing the dirty flag. The reason for the partial cycle clears the ready to clean flag. If the disinfection cycle completes in full, the process can log the complete cycle, reset all the flags and turn the UV source off 302 and then begin monitoring for presence again 304. After a compete disinfection cycle, a delay period or delay flag may be inserted to avoid running another disinfection cycle too soon. However, in practice, even if there is no presence detected and the ready to clean flag is set shortly after completion of a full disinfection cycle, another cycle will not be run because the dirty flag will not have been set yet. The process can be adjusted depending on how the disinfection apparatus is configured. For example, if the pattern detection is particularly sensitive with regard to setting the dirty flag, then a periodic delay period may make sense. However, if the pattern detection is not particularly sensitive with regard to the dirty flag, it may be appropriate to disinfect, even close in time—assuming the dirty flag is set again.

Figure 24:
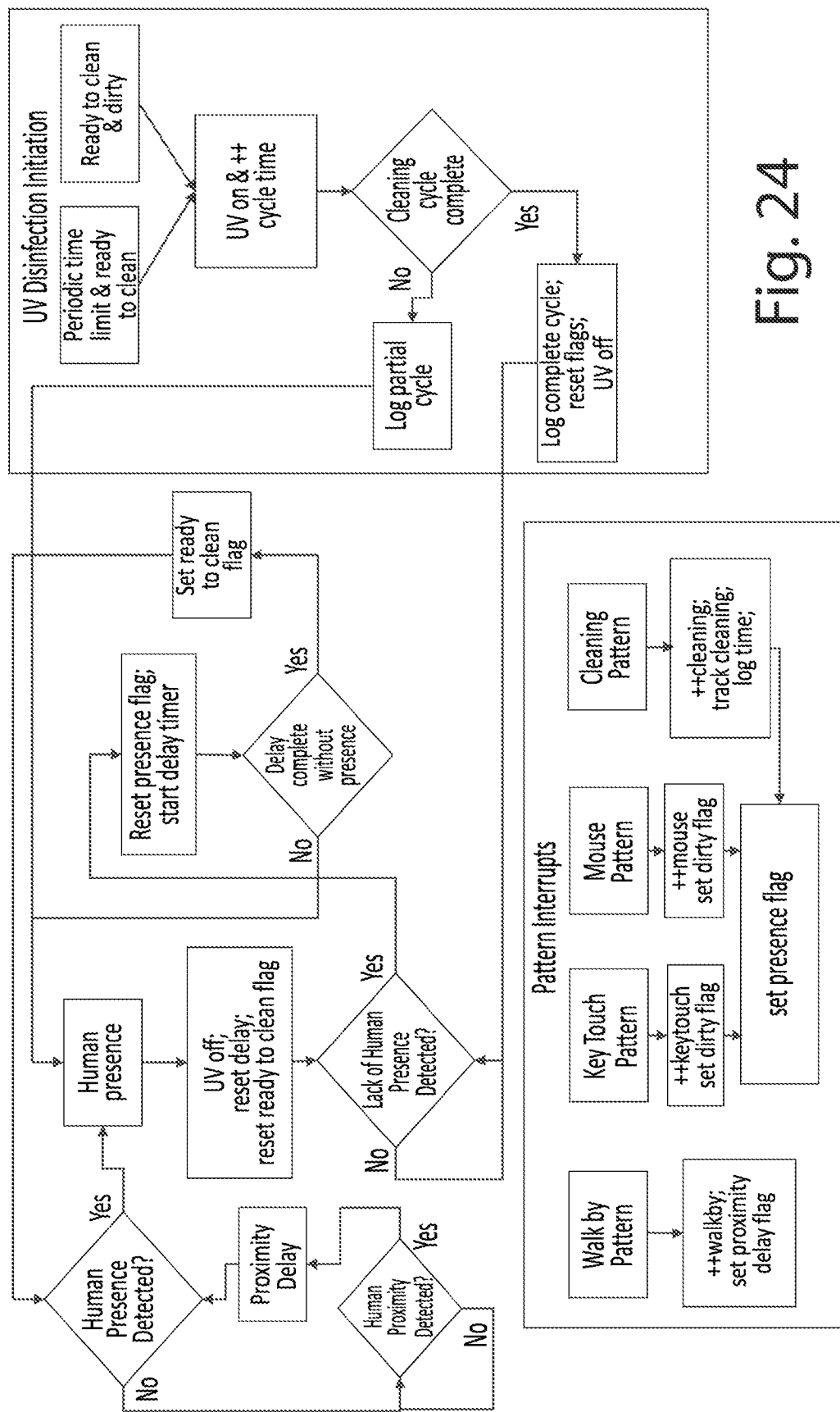
FIG. 24 illustrates a representative diagram of an alternative disinfection scheme in accordance with another embodiment.

FIG. 24 illustrates an alternative embodiment of a disinfection control scheme. FIG. 24 is organized into pattern interrupts, such as walk by pattern, key touch pattern, mouse pattern, and cleaning pattern. When any of these patterns (or other patterns added via an update in the field or a version update) are identified by the controller, they interrupt the disinfection device once it is at a safe time to do so and execute flow paths, increasing counters to track different events and setting various flags associated with those events. Then, the process can return to its previous position where the flow path of the control logic may be altered due to the different flags being set. Similar to FIG. 15, a ready to clean flag and a dirty flag can trigger a UV disinfection cycle as well as aperiodic time limit being reached in conjunction with a ready to clean flag. The disinfection device can include the ability to detect human presence, detect human proximity, and to detect a lack of human presence at different spots in the flowchart. The proximity delay can be a delay period introduced after detecting user proximity such that efforts to detect human presence can be managed so as not to be a constant drain of resources for the disinfection device.

In some embodiments, where the periodic timer has lapsed, but the disinfection device is not yet ready to clean for a substantial period of time, the event can be recorded. Further, the threshold for being ready to clean may be progressively lowered by lowering the delay timer length the longer the periodic timer has been lapsed. In addition or alternatively, the disinfection device may provide feedback to let the user know that the disinfection device would like to initiate a cleaning cycle, e.g., by blinking or changing the color of a visible light LED.

With regard to the delay time, it can be varied dynamically. For example, the amount of delay time before authorizing a ready to clean flag can vary based on tracked patterns. For example, the walk by counter or another indication of human activity in the vicinity may be utilized to adjust the delay time. Alternatively, the amount of human activity during a predetermined period of time or the amount of time since the last disinfection cycle can be utilized to adjust the delay time before disinfection begins, either increasing or decreasing the amount.

Figure 16:
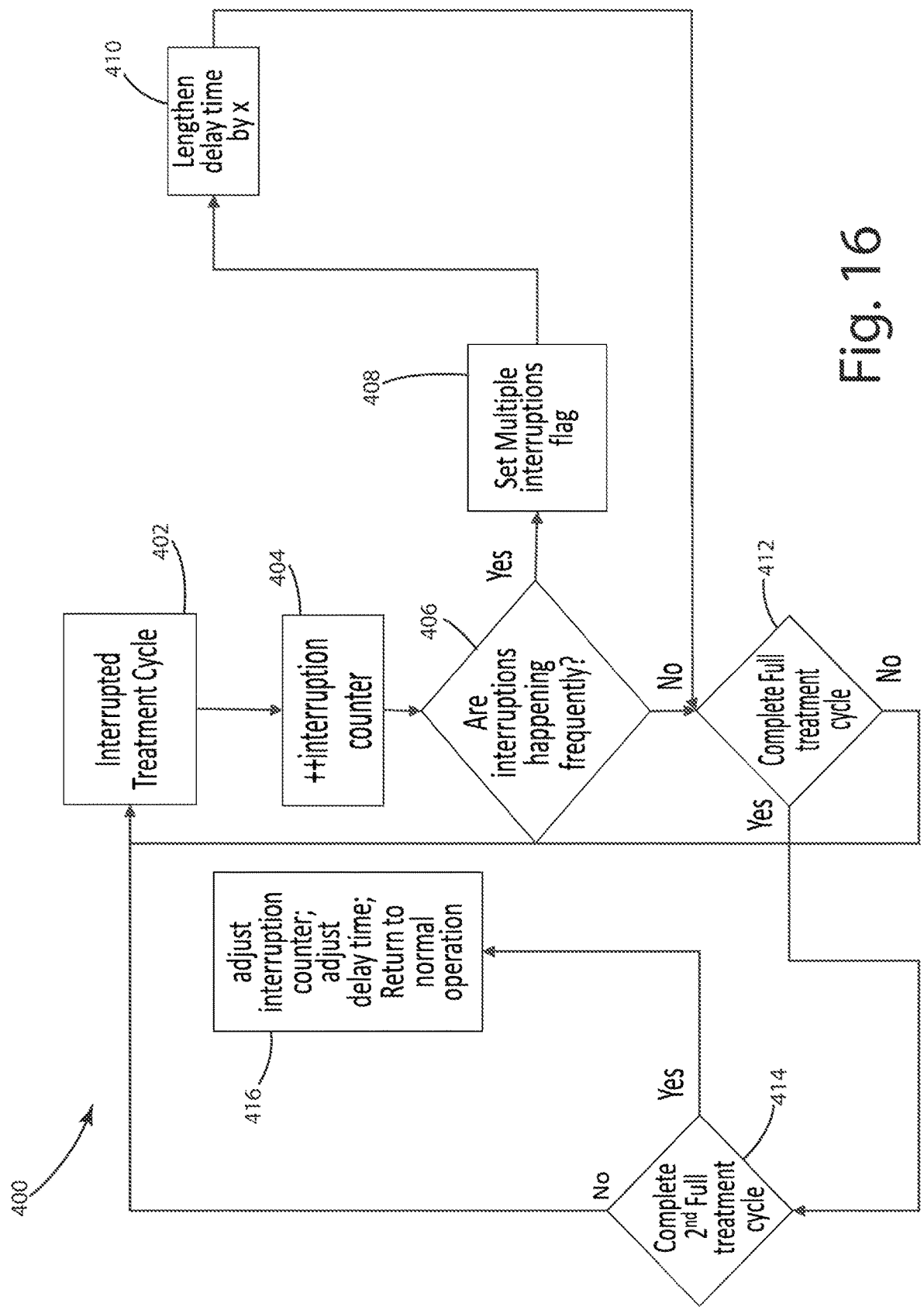
FIG. 16 illustrates a representative flow chart of one embodiment of a progressive delay mode.

FIG. 16 illustrates one embodiment of a progressive delay mode 400 flowchart. In response to the disinfection cycle being interrupted 402, the progressive delay mode 400 can be enacted, which includes incrementing an interruption counter 404 and logging any other suitable information (e.g., cause of interruption, time, and date), determining whether interruptions are happening frequently by a predefined criteria 406, for example, the value of the interruption counter or number of interruptions over a particular unit of time. If the interruptions are occurring frequently 406, for example the interruption counter is equal to or greater than 2, then the multiple interruptions flag can be set 408 and the length of delay before initiating a disinfection cycle can be increased 410. The amount of the increase can be a static amount or can vary depending on the interruption counter. For example, in one embodiment, the delay time increases at an exponential rate based on the interruption counter, to a maximum length.

If the interruptions are not occurring frequently or after the delay time has been adjusted, the progressive delay mode 400 can include determining whether the next full treatment cycle completes 412. If it is interrupted, then the progressive delay mode loops again, beginning with incrementing the interruption counter again 404. However, if the next full treatment cycle is successful, then the process will wait for another full treatment cycle to be initiated to see if back-to-back disinfection cycles can be completed 414. If the second back-to-back treatment cycle does not complete, the process starts over, with incrementing the interruption counter. However, if it does complete, then the interruption counter is adjusted, the delay time is adjusted, and operation returns to normal 416. In some embodiments, the interruption counter is reset and the delay time is reset such that the disinfection device has no record of the progressive delay mode being activated. In other embodiments, the counter and delay time are reset, but before that the information is logged for review and analysis. In other embodiments, instead of completely resetting the interruption counter and delay time, the values may be reduced or decremented. For example, each time a treatment cycle completes without interruption, the interruption counter can be decremented and the delay time reduced. The amount of the reduction can mirror the increases, or may be set to decrease at a slower or faster rate than the increases.

Figures 17A, 17B:
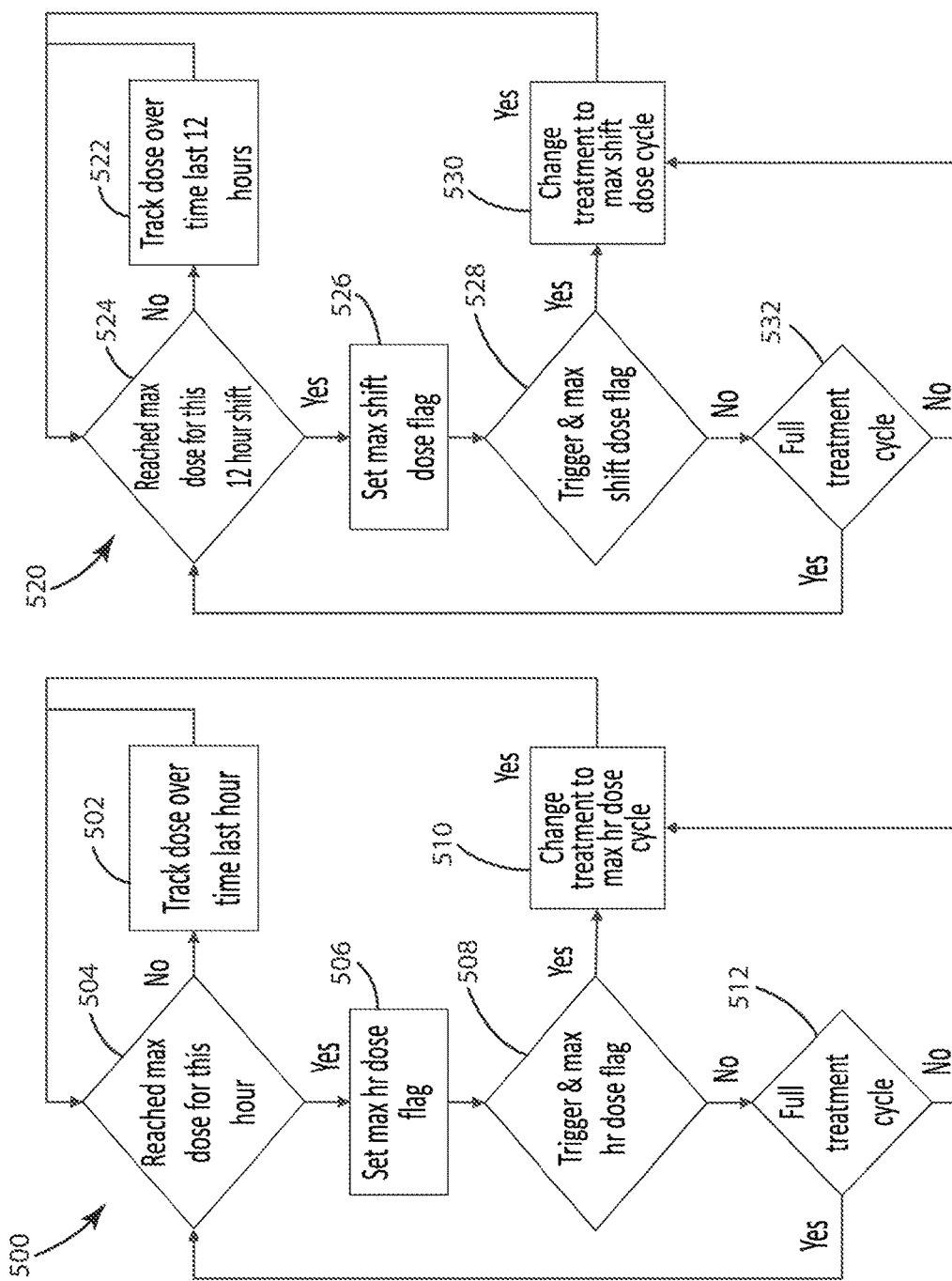
FIGS. 17A-B illustrate two embodiments of dose limitation methods in accordance with the present disclosure.

The disinfection device 100 can track dosage over time and control operation to change the UV treatment accordingly. For example, FIGS. 17A-B show methods for tracking dosage maximums per hour 500 (FIG. 17A) and per 12 hour shift 520 (FIG. 17B). The methods can each include tracking dosage over a period of time, for example over the last hour 502 or over the last twelve hours 522. If a maximum dosage for that time period is reached 504, 524, the method can include setting an appropriate maximum dosage flag 506, 526 indicating the maximum dosage has been accumulated at the target disinfection area for that time period. From there, the methods can include checking to see whether the trigger for changing UV operation is set 508, 528. If it is, then the control methodology for the UV light is altered to account for the dosage level reaching its maximum for that period of time 510, 530. For example, the alteration may include reducing the UV light intensity by a predetermined static or scaling percentage. The percentage can scale based on the difference between the recommended dosage level and the current dosage. If there is no trigger or the maximum dosage isn't set, then the UV treatment system attempts to complete a full treatment cycle 512, 532. If the full treatment cycle is completed, the process returns to monitoring the total dosage against a maximum dosage per unit time 504, 524 and tracking 502, 522. If the full treatment cycle is interrupted, the treatment is changed to a different UV cycle 510, 530.

Throughout this disclosure, a variety of different sensor outputs are discussed including different events that can be detected either by considering the sensor output in isolation or in view of various assumptions about the disinfection device. It should also be appreciated that the sensor output from one sensor can provide meaningful triggers for other sensor output. That is, valuable insights can be learned by overlaying the sensor output in time, not only by virtue of the different sensor output providing meaningful data at the same time stamp, but also by the lack of such meaningful data at the same time stamp—for example, switching between keyboard and mouse usage. Further, sequence patterns of the sensor output data can provide valuable and powerful predictions that can inform not only disinfection decisions, but non-disinfection decisions as well.

Meaningful occupancy information and movement data can be collected by combining sensor data from one or more disinfection devices installed within a building, such as a hospital. Each of the disinfection devices can be provisioned to a particular building location and have a particular serial number, position, orientation, and installation configuration in order to provide reliable and meaningful occupancy data. For example, time of flight sensors on multiple disinfection devices can cooperate to provide a full occupancy dataset and track movement between hospital rooms, which can be combined with other data to provide meaningful and helpful insights.

As another example of how the combination of sensor data can interact and intermingle, seemingly errant data can lead to interesting insights. For example, by aligning HAI data with sensor output data, especially in large quantities, patterns can emerge. For example, in one example, where a substantial uptick in HAI occurs, the data surrounding those events can be scrutinized more closely to look for patterns. For example, an accelerometer may detect an HVAC system turning on and that could align with an uptick in infections with the patients in those rooms at the time where the HVAC turned on after a long period of being off. This is just one example. Other patterns can also emerge as data is collected and compared to other data in other hospital environments that have similarities and differences.

With the amount of data available to be collected, there is a risk that too much data is collected and that it becomes difficult to map the data to an interesting and meaningful disinfection model or to make accurate predictions. Accordingly, it is worth noting that the different sensor output can be utilized not only in the underlying analysis and detection of events but in the triggering of the data collection itself. For example, the time of flight data can be utilized to narrow data to times when presence is detected. Further, as many pieces of data will be routine, normal, and correspond to expected norms, that data can be categorized at the device level. However, when a particular set of data is not recognized, that data can be flagged as a packet with other sensor output from that same general time frame. To the extent that multiple disinfection devices or other data sources with time stamp information are available, those data sources can be combined to better understand the underlying data and to uncover new events that can then be categorized and tagged in the future.

Figure 22:
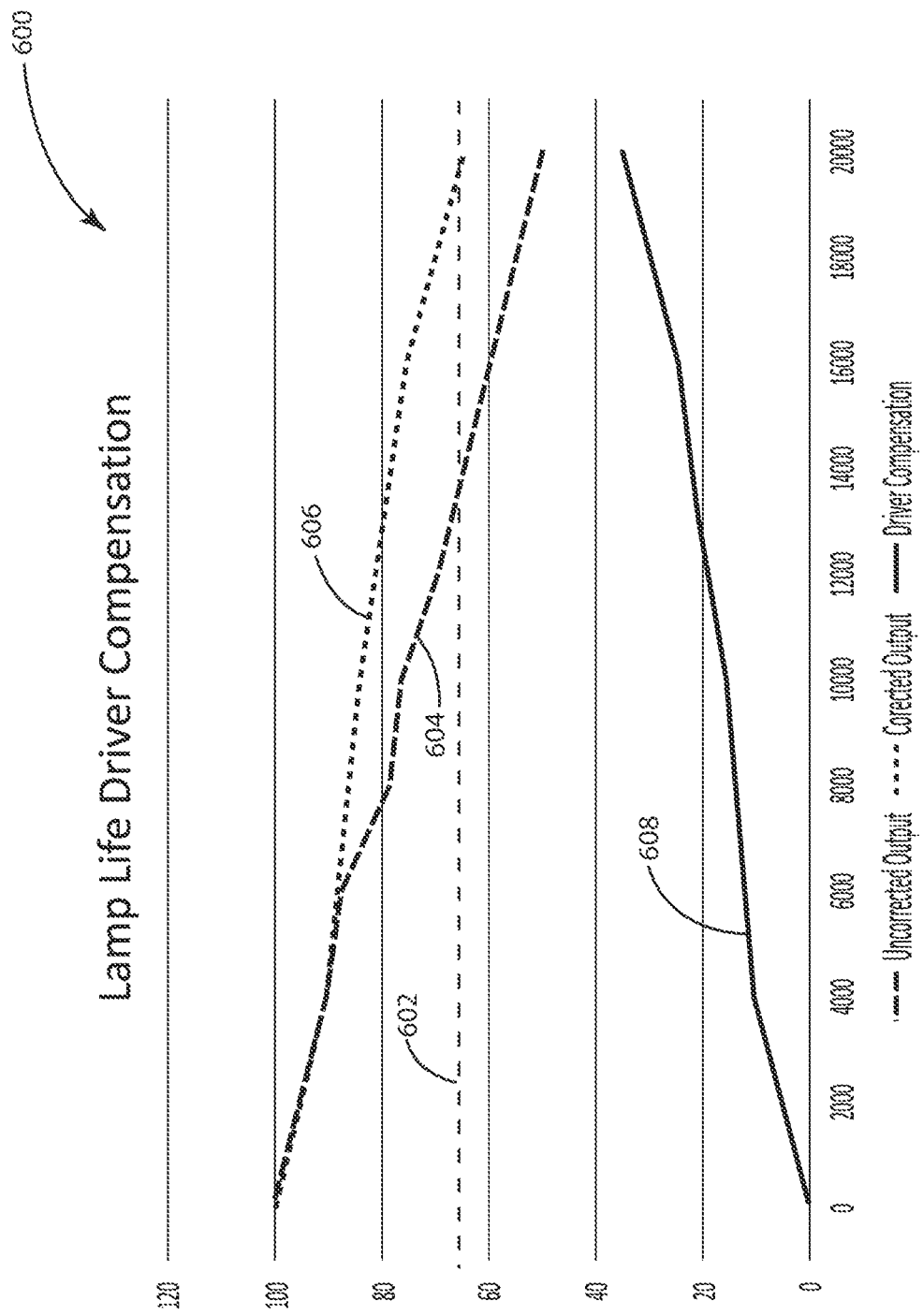
FIG. 22 illustrates an exemplary graph of uncorrected lamp output, lamp life driver compensation, and corrected lamp output.

The UV driver in the driver module 17 can be configured to provide lamp life driver compensation. For example, FIG. 22 illustrates a graph 600 that shows a lamp life driver compensation configuration for the UV driver. The x-axis of the graph shows the number of hours the UV lamp has been operational while the y-axis shows the percentage of power output from the uncorrected bulb 604, the power output from the corrected bulb 606, or the UV driver voltage compensation percentage 608 applied by the UV driver to the voltage for the UV source. The dashed line 602 represents the level at which the UV source output is deemed to have reached its end of life and should be replaced. As shown by the graph, by applying an additional amount of voltage to the driver using the driver voltage compensation percentage, the life of the UV lamp can be extended by about 6000 hours.

The gyroscope 220 can be utilized for attitude settings and the accelerometer 218 for touch sensing. These sensors can be utilized not only in the pattern detection and control aspects of the disinfection device, but also as part of the configuration at setup. The gyroscope attitude parameters, e.g., a particular yaw, pitch, and roll, can be calibrated and sensed at installation. Then, if the parameters of the attitude of the disinfection device change past a guard band limit, the disinfection apparatus can be flagged as being disturbed by the user or damaged. In addition, the disinfection device can indicate with its visible lighting system an error status and deactivate the unit to reduce potential UV exposure risk. Put simply, the gyroscope can be configured to provide sensor output indicative of the attitude of an installation of the disinfection device or change in position of the disinfection device and a control circuit can be configured to detect alteration of an installation of the disinfection device or change in position of the disinfection device in response to sensor output from the gyroscope.

Figures 25, 26:
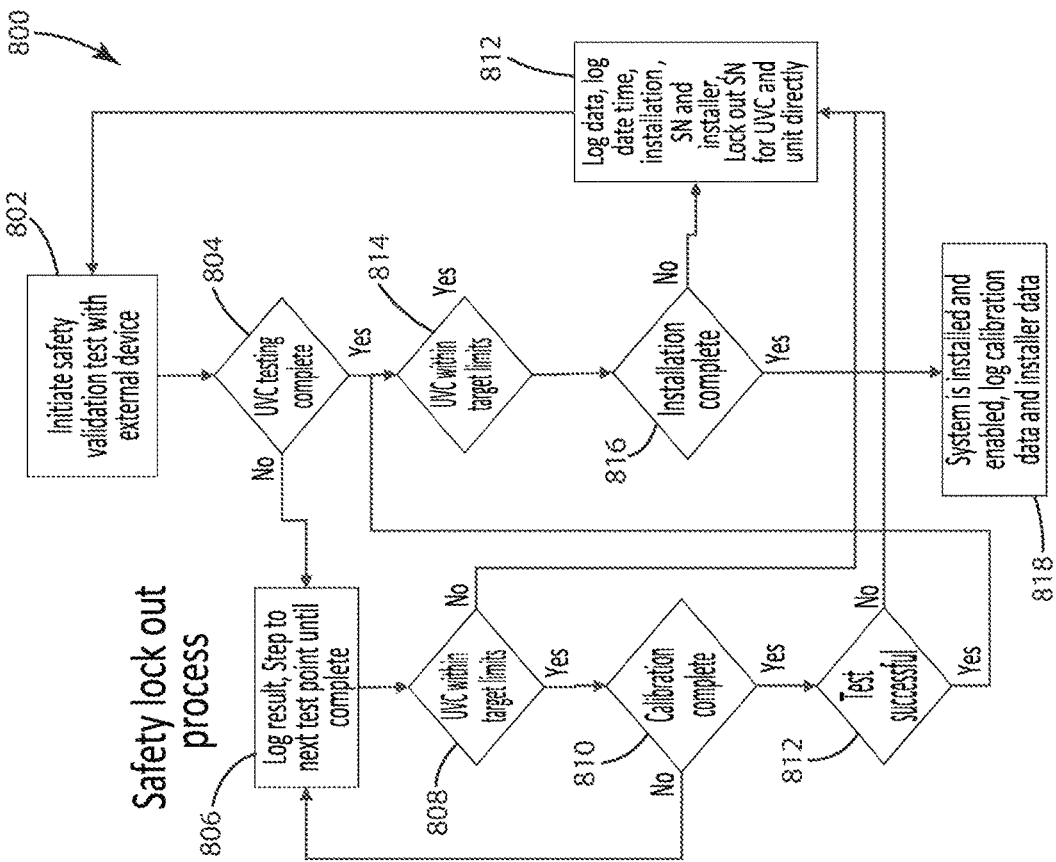
FIG. 25 illustrates a representative system diagram of installation of a disinfection device.
FIG. 26 illustrates a representative flow diagram of installation of a disinfection device.
Figure 29:
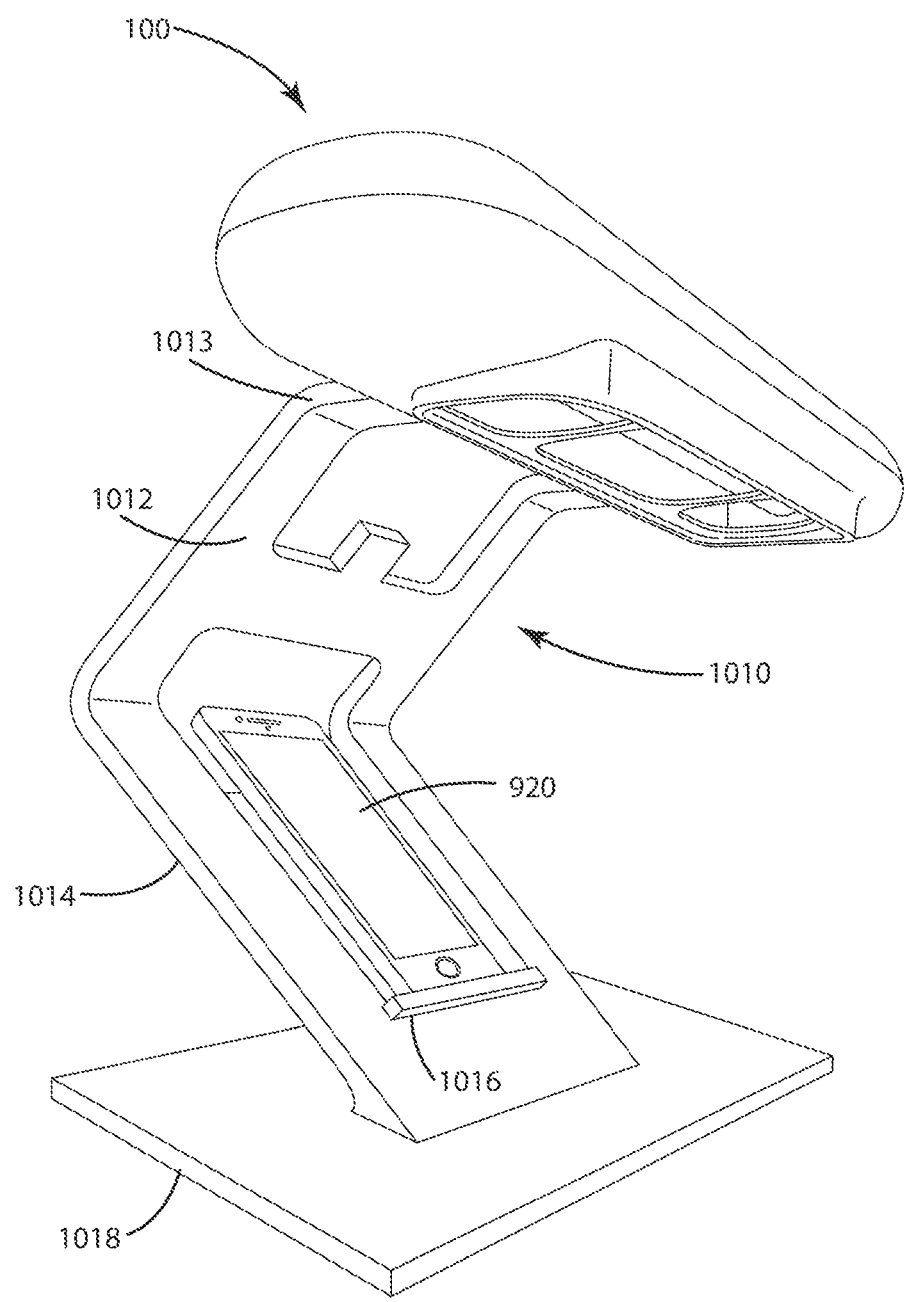
FIG. 29 illustrates an exemplary perspective view of another embodiment of a disinfection apparatus including a support base with a ledge for disposing a mobile device.

The disinfection device can be installed and configured in accordance with a safety validation testing. One embodiment of such installation and configuration is discussed in connection with FIGS. 25-26. FIG. 25 illustrates a representative diagram of a disinfection apparatus installation system 700 showing an embodiment of a disinfection device 100 of the present disclosure being installed using a validation test with a UV-C light meter 702 and installation device 704, such as a smart phone. One embodiment of an installation process 800 in accordance with the present disclosure will now be described in connection with FIG. 26. If UVC testing is not complete 804, the user is directed to point the UVC meter (or the UVC meter is automatically configured to point at a specific area of the target disinfection area) and UVC meter reports a UVC value 806 associated with that area. The UV-C measurement from the meter can take a variety of different forms, such as radiant power, average of several UV intensity value measured in watts or micro watts, an average value of UV intensity/unit area, or another value associated with characterizing the UV-C energy/light received (or output) by the disinfection device. The UV-C measurement is received by the installation device 704 and a check is made as to whether the UV-C measurement is within target limits 808. If it is and the calibration is not yet complete 810, then the result is logged and the user can be directed to move the UV-C meter to another test point (or the meter can automatically adjust for the next test point) until the process is complete 806. If the UVC is not within target limits, then the calibration can be stopped and a record taken 812. Specifically, the process can include logging the date and time, installation identification information such as serial number and installer. Further, the process can lock out the serial number of the disinfection device such that the disinfection device cannot activate the UV-C source. For example, the control circuit of the disinfection device 100 can be locally configured such that the UV-C cannot be activated. In addition, the installation system can flag the serial number such that it cannot be provisioned until the underlying issue causing the calibration issue is addressed. After calibration, a safety validation test can be initiated. If the test fails, the logging and lockout 812 can be conducted and either further safety validating testing can be performed or recalibration, or both 802. If the testing is complete and the UVC is within the limits 814 during the test then the installation can be deemed complete, enabled, and the calibration data can be logged along with installer data 818. At this point the gyroscope attitude measurements can be taken and stored for anti-tampering features where disturbance of the disinfection device causing the gyroscope values to change past a guard band (e.g. 20% change of yaw, pitch, roll, or some combination thereof), can flag the device as being tampered with or otherwise moved. Such trigger can also deactivate the UV light.

By utilizing the gyroscope attitude settings for anti-tampering feedback and control, the accelerometer can be freed up to be used as the primary touch detection, as discussed in the disclosure. The accelerometer, for example where the disinfection device is installed on a medical cart, can be used as a touch detector that can easily see typing segments. In some embodiments, the motion sensors, such as the time of flight sensor can be configured exclusively for presence detection allowing the other sensors to be configured for sensing other measurements, which may not be conducive to presence detection. The various sensors cooperate to provide, a holistic view of the disinfection apparatus, the target disinfection area, and human activity with that area. For example, in the case where the disinfection apparatus is installed on a medical cart, the sensors enable understanding the movement of the cart, typing on the keyboard of the workstation on the cart, adjusting the cart and keyboard, transferring the cart from room to room and tracking the cleaning processes associated with the cart. All of these steps and different events can be recognized and stored or pushed up to the cloud for analysis and metric tracking. Further, having multiple safety sensors enhances the design and functionality to provide a safer and more accurate disinfection device.

The detailed embodiments have been described in accordance with the various aspects of the present disclosure, it should be observed that the embodiments include combinations of method steps and apparatus components related to a disinfection apparatus and method thereof. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like reference characters in the description and drawings represent like elements.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Such components can be physically configured in any suitable manner, such as by mounting them to one or more circuit boards, or arranging them in other manners, whether combined into a single unit or distributed across multiple units. Similarly, steps of a method or process described herein may be embodied directly in hardware, in a software module executed by a processor, or in a combination thereof. A software module may reside in random access memory (RAM), flash memory, read-only memory (ROM), erasable programmable read-only memory (EPROM), electrically erasable programmable read-only memory (EEPROM), registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although particular embodiments have been described of the present invention, it is not intended that such references be construed as limitations upon the scope of this invention except as set forth in the following claims.

The embodiments of the invention in which an exclusive property or privilege is claimed are defined as follows:

1. A UV disinfection device comprising:
    a housing having two, opposite lateral ends and a midpoint;
    a UVC light source disposed within the housing;
    a dual passive infrared sensor system including two passive infrared sensors, one passive infrared sensor being disposed on one side of the housing midpoint and the other passive infrared sensor being disposed on the other side of the housing midpoint;
    a control system configured to:
    receive sensor output from the two passive infrared sensors of the dual passive infrared sensor system,
    take a difference between the sensor output from the two passive infrared sensors of the dual passive infrared sensor system,
    detect an event pattern based on the difference between the sensor output from the two passive infrared sensors of the dual passive infrared sensor system, wherein the event pattern is indicative of position of human activity in a target disinfection area of the UV disinfection device, and
    control operation of the UV-C light source based on the detected event pattern.

2. The UV disinfection device of claim 1 wherein detection of an event pattern based on the sensor output includes detection of at least one of a plurality of redundant event patterns, and wherein the control system is configured to control operation of the UV-C light source in a particular manner in response to detection of at least one of the plurality of redundant event patterns, whereby the dual passive infrared sensor system provides sensor output indicative of lateral position of human activity.

3. The UV disinfection device of claim 2 wherein one of the plurality of redundant event patterns includes detection of a first threshold amount of infrared energy at one of the two passive infrared sensors before detection of a second threshold amount of infrared energy at the other of the two passive infrared sensors, whereby the dual passive infrared sensor system provides sensor output indicative of lateral position of human activity, and wherein another one of the plurality of redundant event pattern includes detection of a passive infrared difference based on comparison of the sensor output from the two passive infrared sensors.

4. The UV disinfection device of claim 1 wherein detection of the event pattern includes detection of an initial lack of human presence based on sensor output from one of the two passive infrared sensors and wherein in response to the initial lack of human presence, the control system is configured to control operation of the UV-C light source by initiating a delay timer to track an amount of delay time before initiation of a disinfection cycle of the UV-C light source, wherein before the delay time completes, the control system is configured to confirm the initial lack of human presence based at least on sensor output from the other of the two passive infrared sensors.

5. The UV disinfection device of claim 1 wherein the event pattern is a presence event pattern.

6. The UV disinfection device of claim 5 wherein the presence event pattern is at least one of a mouse interaction event pattern, a walk by event pattern, a keyboard interaction event pattern, a proximity event pattern, and an occupancy event pattern.

7. The UV disinfection device of claim 1 wherein the event pattern is indicative of a cleaning event, wherein the control system is configured to determine a length of the cleaning event, and wherein the control system is configured to control operation of the UV-C light source based on the detected event pattern being indicative of a cleaning event and the determined length of the cleaning event.

8. The UV disinfection device of claim 7 wherein the cleaning event includes a dwell event and a wiping event, and wherein the control system is configured to determine the length of the cleaning event based on at least one of a length of the dwell event prior to the wiping event and a length of the wiping event.

9. The UV disinfection device of claim 7, wherein the event pattern indicative of the cleaning event includes a plurality of wiping event patterns, wherein the plurality of wiping event patterns includes a wipe left event pattern and a wipe right event pattern, and wherein the control system is configured to determine the length of the cleaning event based on the plurality of wiping event patterns.

10. The UV disinfection device of claim 1 wherein the control system is configured to detect a sequence of event patterns based on the sensor output.

11. The UV disinfection device of claim 1 wherein the control system is configured to control operation of the UV-C light source according to a disinfection cycle, wherein the control system is configured to detect a presence event pattern, and wherein the control system is configured to interrupt the disinfection cycle in response to detection of the presence event pattern by deactivating the UV-C light source.

12. The UV disinfection device of claim 1 wherein the control system is configured to control operation of the UV-C light source according to a disinfection control loop, wherein the control system is configured with a progressive delay mode that adjusts a delay time before initiating a disinfection cycle after the control system detects a lack of human presence event pattern, wherein during progressive delay mode the control system adjusts the delay time based on frequency of disinfection cycle interruptions.

13. The UV disinfection device of claim 1 wherein the control system is configured with an overdose prevention mode that tracks and adjusts dosage over time based on a threshold UV disinfection dosage.

14. The UV disinfection device of claim 1 wherein the control system includes a UV driver to control operation of the UV-C light source, wherein the control system is configured to correct UV-C light source intensity over life of the UV-C light source by increasing the voltage supplied to the UV-C light source to compensate for loss of intensity over life of the UV-C light source.

15. The UV disinfection device of claim 1 wherein the two passive infrared sensors are disposed toward the opposite lateral ends of the housing and wherein the two passive infrared sensors are oriented toward the target disinfection area.

16. The UV disinfection device of claim 1 wherein the two passive infrared sensors are disposed toward the opposite lateral ends of the housing and the dual passive infrared sensor system is configured to detect lateral human movement proximate to the UV disinfection device.

17. A UV disinfection method comprising:
providing a UV disinfection device having a housing, a UV-C light source, a control system, and two passive infrared sensors;
sensing passive infrared sensor output from the two passive infrared sensors;
taking a difference between the sensor output from the two passive infrared sensors,
detecting an event pattern based on the difference between the passive infrared sensor output from the two passive infrared sensors, wherein the event pattern is indicative of position of human activity in a target disinfection area of the UV disinfection device; and
controlling operation of the UV-C light source based on the detected event pattern.

18. The UV disinfection method of claim 17 wherein the event pattern is a presence event pattern.

19. The UV disinfection method of claim 18 wherein the presence event pattern is at least one of a mouse interaction event pattern, a walk by event pattern, a keyboard interaction event pattern, a proximity event pattern, and an occupancy event pattern.

20. The UV disinfection method of claim 17 wherein the event pattern is indicative of a cleaning event, the method including determining a length of the cleaning event, and wherein the controlling includes controlling operation of the UV-C light source based on the detected event pattern indicative of the cleaning event and the determined length of the cleaning event.

21. The UV disinfection method of claim 20 wherein the cleaning event includes a dwell event and a wiping event, and the determining the length of the cleaning event includes determining the length of the cleaning event based on at least one of a length of the dwell event prior to the wiping event and a length of the wiping event.

22. The UV disinfection method of claim 20, wherein the event pattern indicative of the cleaning event includes a plurality of wiping event patterns, wherein the plurality of wiping event patterns includes a wipe left event pattern and a wipe right event pattern, and the determining the length of the cleaning event includes determining the length of the cleaning event based on the plurality of wiping event patterns.

23. The UV disinfection method of claim 17 including detecting a sequence of event patterns based on the sensor output.

24. The UV disinfection method of claim 17 wherein controlling operation of the UV-C light source includes controlling operation of the UV-C light source according to a disinfection cycle, wherein detecting the event pattern includes detecting a presence event pattern, and wherein controlling operation of the UV-C light source includes interrupting the disinfection cycle in response to detecting the presence event pattern by deactivating the UV-C light source.

25. The UV disinfection method of claim 17 wherein controlling operation of the UV-C light source includes:
controlling operation of the UV-C light source according to a disinfection control loop having a delay time before initiating a disinfection cycle after detecting a lack of human presence event pattern; and
adjusting the delay time based on a frequency of disinfection cycle interruptions.

26. The UV disinfection method of claim 17 including tracking and adjusting dosage of the UV-C light source over time based on a threshold UV disinfection dosage.

27. The UV disinfection method of claim 17 wherein the detecting the event pattern based on the passive infrared sensor output includes detecting lateral human movement proximate to the UV disinfection device based on the passive infrared sensor output.

28. The UV disinfection method of claim 17 wherein detecting the event pattern based on the sensor output includes detecting at least one of a plurality of redundant event patterns, and wherein controlling operation of the UV-C light source includes controlling operation of the UV-C light source in a particular manner in response to detecting at least one of the plurality of redundant event patterns.

29. The UV disinfection method of claim 28 wherein one of the plurality of redundant event patterns includes detecting a first threshold amount of infrared energy at one of the two passive infrared sensors before detecting a second threshold amount of infrared energy at the other of the two passive infrared sensors, and wherein another of the plurality of redundant event pattern includes detecting a passive infrared difference based on comparison of the sensor output from the two passive infrared sensors.

30. The UV disinfection method of claim 17 wherein detecting the event pattern includes detecting an initial lack of human presence based on sensor output from one of the two passive infrared sensors and in response to the initial lack of human presence, controlling operation of the UV-C light source by initiating a delay timer to track an amount of delay time before initiation of a disinfection cycle of the UV-C light source, and, before the delay time completes, confirming the initial lack of human presence based at least on sensor output from the other of the two passive infrared sensors.

* * * * *